US009932588B2

(12) United States Patent
Arora

(10) Patent No.: US 9,932,588 B2
(45) Date of Patent: Apr. 3, 2018

(54) INHIBITION OF OXIDATIVE STRESS IN ATRIAL FIBRILLATION

(71) Applicant: Northwestern University, Evanston, IL (US)

(72) Inventor: Rishi Arora, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/542,501

(22) Filed: Nov. 14, 2014

(65) Prior Publication Data

US 2015/0203852 A1 Jul. 23, 2015

Related U.S. Application Data

(60) Provisional application No. 61/904,925, filed on Nov. 15, 2013.

(51) Int. Cl.
| A61K 48/00 | (2006.01) |
| C07H 21/02 | (2006.01) |
| C07H 21/04 | (2006.01) |
| C12N 15/11 | (2006.01) |
| C12N 15/113 | (2010.01) |
| A61B 5/046 | (2006.01) |
| A61B 5/00 | (2006.01) |
| A61B 5/04 | (2006.01) |

(52) U.S. Cl.
CPC .......... *C12N 15/1137* (2013.01); *A61B 5/046* (2013.01); *A61B 5/04012* (2013.01); *A61B 5/4848* (2013.01); *C12Y 106/03* (2013.01); *C12N 2310/14* (2013.01); *C12N 2310/531* (2013.01)

(58) Field of Classification Search
USPC ........................................ 514/44; 536/24.5
See application file for complete search history.

(56) References Cited

U.S. PATENT DOCUMENTS

| 9,078,918 B2 * | 7/2015 | Arora ................. A61K 48/0058 |
| 2010/0035963 A1 * | 2/2010 | Chajut .................. A61K 48/00 514/44 A |
| 2011/0183990 A1 * | 7/2011 | Antzelevitch ........ A61K 31/343 514/252.12 |

(Continued)

FOREIGN PATENT DOCUMENTS

WO 2008152636 12/2008

OTHER PUBLICATIONS

Somasuntharam et al. (Biomaterials, Oct. 2013 vol. 34(31):7790-7798, epub Jul. 13, 2013).*

(Continued)

*Primary Examiner* — Terra C Gibbs
(74) *Attorney, Agent, or Firm* — Klintworth & Rozenblat IP LLP

(57) ABSTRACT

Disclosed herein are pharmaceutical compositions and methods for inhibiting oxidative stress in a subject having atrial or ventricular arrhythmias, ventricular failure or heart failure. The methods include administering an effective amount of a NOX2 inhibitor agent to the subject, wherein said administering is under conditions such that a level of oxidative stress in myocardial tissue is reduced or eliminated. The pharmaceutical compositions include a NOX2 inhibitor agent.

16 Claims, 21 Drawing Sheets

(56) References Cited

U.S. PATENT DOCUMENTS

2012/0136044 A1* 5/2012 Kalinski .............. A01K 67/027
514/44 A

OTHER PUBLICATIONS

Thomas James (Circulation, 1961 vol. 24. October, pp. 761-766).*
Hurwitz et al. (Chest, 1964 vol. 45:616-626).*
Aistrup GL, Villuendas R, Ng J, et al. Targeted G-protein inhibition as a novel approach to decrease vagal atrial fibrillation by selective parasympathetic attenuation. Cardiovasc Res 2009;83:481-92.
Aistrup GL, Cokic I, Ng J, et al. Targeted nonviral gene-based inhibition of Galpha(i/o)-mediated vagal signaling in the posterior left atrium decreases vagal-induced atrial fibrillation. Heart Rhythm 2011;8(11):1722-9.
Aistrup GL, Balke CW, Wasserstrom JA. Arrhythmia triggers in heart failure: the smoking gun of [Ca2+]i dysregulation. Heart Rhythm 2011;8:1804-8.
Aldhoon B, Melenovsky V, Peichl P, Kautzner J. New insights into mechanisms of atrial fibrillation. Phys. Res./ Academia Scientiarum Bohemoslovaca 2010;59:1-12.
Antoons G, Sipido KR. Targeting calcium handling in arrhythmias. Europace 2008;10:1364-9.
Arora R, Verheule S, Scott L, et al. Arrhythmogenic substrate of the pulmonary veins assessed by high-resolution optical mapping. Circulation 2003;107(13)1816-21.
Arora R, Ng J, Ulphani J, et al. Unique autonomic profile of the pulmonary veins and posterior left atrium. J Am Coll Cardiol 2007;49(12):1340-8.
Arora R, Ulphani JS, Villuendas R, et al. Neural substrate for atrial fibrillation: implications for targeted parasympathetic blockade in the posterior left atrium. Am J Physiol Heart Circ Physiol 2008;294:H134-44.
Arora R. Recent insights into the role of the autonomic nervous system in the creation of substrate for atrial fibrillation: implications for therapies targeting the atrial autonomic nervous system. Circ Arrhythm Electrophysiol 2012;5:850-9.
Ashpole NM, Herren AW, Ginsburg KS, et al. Ca2+/calmodulin-dependent protein kinase II (CaMKII) regulates cardiac sodium channel NaV1.5 gating by multiple phosphorylation sites. J Biol Chem 2012;287(24):19856-69.
Balasubramaniam R, Kistler PM. Atrial Fibrillation in Heart failure: the chicken or the egg?. Heart 2009;95:535-9.
Belevych AE, Terentyev D, Terentyeva R, et al. Shortened Ca2+ signaling refractoriness underlies cellular arrhythmogenesis in a postinfarction model of sudden cardiac death. Circ Res 2012;110:569-77.
Benjamin EJ, Levy D, Vaziri SM, D'Agostino RB, Belanger AJ, Wolf PA. Independent risk factors for atrial fibrillation in a population-based cohort. The Framingham Heart Study. JAMA 1994;271(11):840-4.
Bode et al., Gadolinium Decreases Stretch-Induced Vulnerability to Atrial Fibrillation Circulation 2000; 101(18):2200-05.
Bootman MD, Smymias I, Thul R, Coombes S, Roderick HL. Atrial cardiomyocyte calcium signalling. Biochim Biophys Acta 2011;1813:922-34.
Bovo E, Lipsius SL, Zima AV. Reactive oxygen species contribute to the development of arrhythmogenic Ca(2)(+) waves during beta-adrenergic receptor stimulation in rabbit cardiomyocytes. J Physiol 2012;590(14):3291-304.
Carnes CA, Chung MK, Nakayama T, et al. Ascorbate attenuates atrial pacing-induced peroxynitrite formation and electrical remodeling and decreases the incidence of postoperative atrial fibrillation. Circ Res 2001;89:E32-8.
Carnes CA, Janssen PM, Ruehr ML, et al. Atrial glutathione content, calcium current, and contractility. J Biol Chem 2007;282(38):28063-73.
Cave AC, Brewer AC, Narayanapanicker A, et al. NADPH oxidases in cardiovascular health and disease. Antioxid Redox Signal 2006;8(5&6):691-728.
Chou CC, Nihei M, Zhou S, et al. Intracellular calcium dynamics and anisotropic reentry in isolated canine pulmonary veins and left atrium. Circulation 2005;111:2889-97.
Christensen MD, Dun W, Boyden PA, Anderson ME, Mohler PJ, Hund TJ. Oxidized calmodulin kinase II regulates conduction following myocardial infarction: a computational analysis. PLoS Comput Biol 2009;5(12):e1000583.
Ciaccio EJ, Biviano AB, Whang W, Gambhir A, Garan H. Different characteristics of complex fractionated atrial electrograms in acute paroxysmal versus long-standing persistent atrial fibrillation. Heart Rhythm 2010;7:1207-15.
Ciaccio EJ, Biviano AB, Whang W, et al. Differences in repeating patterns of complex fractionated left atrial electrograms in longstanding persistent atrial fibrillation as compared with paroxysmal atrial fibrillation. Circ Arrhythm Electrophysiol 2011;4:470-7.
Cucoranu I, Clempus R, Dikalova A, et al. NAD(P)H Oxidase 4 Mediates Transforming Growth Factor—β1-Induced Differentiation of Cardiac Fibroblasts Into Myofibroblasts. Circ. Res. 2005;97:900-7.
Sutler MJ, Plummer BN, Wan X, et al. Aberrant S-nitrosylation mediates calcium-triggered ventricular arrhythmia in the intact heart Proc Natl Acad Sci U S A 2012;109(44):18186-91.
Dean DA. Nonviral gene transfer to skeletal, smooth, and cardiac muscle in living animals. Am. J. Physiol. Cell. Physiol. 2005;289:C233-45.
Dibs SR, Ng J, Arora R, Passman RS, Kadish AH, Goldberger JJ. Spatiotemporal characterization of atrial activation in persistent human atrial fibrillation: multisite electrogram analysis and surface electrocardiographic correlations—a pilot study. Heart Rhythm 2008;5:686-93.
Donoso P, Sanchez G, Bull R, Hidalgo C. Modulation of cardiac ryanodine receptor activity by ROS and RNS. Front Biosci (Landmark Ed) 2011;16:553-67.
Dworakowski R, Alom-Ruiz SP, Shah AM. NADPH oxidase-derived reactive oxygen species in the regulation of endothelial phenotype. Pharmacol Rep 2008;60:21-8.
Efimov IR, Nikolski VP, Salama G. Optical imaging of the heart. Circ Res 2004;94:21-33.
Erickson JR, Joiner ML, Guan X, et al. A dynamic pathway for calcium-independent activation of CaMKII by methionine-oxidation. Cell 2008;133:462-74.
Erickson JR, He BJ, Grumbach IM, Anderson ME. CaMKII in the cardiovascular system: sensing redox states. Physiol Rev 2011;91:889-915.
Estner HL, Hessling G, Ndrepepa G, et al. Electrogram-guided substrate ablation with or without pulmonary vein isolation in patients with persistent atrial fibrillation. Europace 2008;10:1281-7.
Everett TH 4th MJ, Kok LC, Akar JG, Haines DE. Assessment of global atrial fibrillation organization to optimize timing of atrial defibrillation. Circulation 2001;103:2857-61.
Gerstenfeld EP, Sauer W, Callans DJ, et al. Predictors of success after selective pulmonary vein isolation of arrhythmogenic pulmonary veins for treatment of atrial fibrillation. Heart Rhythm 2006;3:165-70.
Gonzalez DR, Beigi F, Treuer AV, Hare JM. Deficient ryanodine receptor S-nitrosylation increases sarcoplasmic reticulum calcium leak and arrhythmogenesis in cardiomyocytes. Proc Natl Acad Sci U S A 2007;104(51):20612-7.
Gonzalez DR, Treuer AV, Castellanos J, Dulce RA, Hare JM. Impaired S-nitrosylation of the ryanodine receptor caused by xanthine oxidase activity contributes to calcium leak in heart failure. J Biol Chem 2010;285(37):28938-45.
Hashambhoy YL, Winslow RL, Greenstein JL. CaMKII-dependent activation of late INa contributes to cellular arrhythmia in a model of the cardiac myocyte. Conf Proc IEEE Eng Med Biol Soc 2011:4665-8.
Hool LC. Reactive Oxygen Species in Cardiac Signalling: From Mitochondria to Plasma Membrane Ion Channels. Cinical and Experimental Pharmacology and Physiology 2006;33:146-51.
Hori M, Nishida K. Oxidative stress and left ventricular remodelling after myocardial infarction. Cardiovascular Research 2009;81:457-64.
Huang CX, Liu Y, Xia WF, Tang YH, Huang H. Oxidative stress: a possible pathogenesis of atrial fibrillation. Med Hypotheses 2009;72:466-7.
Hund TJ, Koval OM, Li J, et al. A beta(IV)-spectrin/CaMKII signaling complex is essential for membrane excitability in mice. J Clin Invest 2010;120(10):3508-19.

(56) References Cited

OTHER PUBLICATIONS

Leong E-M, Liu M, Sturdy M, et al. Metabolic stress, reactive oxygen species, and arrhythmia. Journal of Molecular and Cellular Cardiology 2012;52:454-63.

Kabra R, Singh JP. Catheter ablation targeting complex fractionated atrial electrograms for the control of atrial fibrillation. Curr Opin Cardiol 2012;27(11):49-54.

Katra RP, Laurita KR. Cellular mechanism of calcium-mediated triggered activity in the heart. Circ Res 2005;96:535-42.

Kim YM, Guzik TJ, Zhang YH, et al. A myocardial Nox2 containing NAD(P)H oxidase contributes to oxidative stress in human atrial fibrillation. Circ Res 2005;97:629-36.

Koduri H, Ng J, Cokic I, et al. Contribution of fibrosis and the autonomic nervous system to atrial fibrillation electrograms in heart failure. Circ Arrhythm Electrophysiol 2012;5(4):640-9.

Kohlhaas M, Maack C. Interplay of defective excitation-contraction coupling, energy starvation, and oxidative stress in heart failure. Trends Cardiovasc Med 2011;21(3):69-73.

Kong MH, Piccini JP, Bahnson TD. Efficacy of adjunctive ablation of complex fractionated atrial electrograms and pulmonary vein isolation for the treatment of atrial fibrillation: a meta-analysis of randomized controlled trials. Europace 2011;13:193-204.

Kong W, Ideker RE, Fast VG. Intramural optical mapping of V(m) and Ca(i)2+ during long-duration ventricular brillation in canine hearts. Am J Physiol Heart Circ Physiol 2012;302:H1294-305.

Volders PG, Vos MA, Szabo B, et al. Progress in the understanding of cardiac early afterdepolarizations and torsades de pointes: time to revise current concepts. Cardiovasc Res 2000;46:376-92.

Wasserstrom JA, Sharma R, Kapur S, et al. Multiple defects in intracellular calcium cycling in whole failing rat heart. Circ Heart Fail 2009;2:223-32.

Wasserstrom JA, Sharma R, O'Toole MJ, et al. Ranolazine Antagonizes the Effects of Increased Late Sodium Current on Intracellular Calcium Cycling in Rat Isolated Intact Heart. Journal of Pharmacology and Experimental Therapeutics 2009;331(2):382-91.

Wasserstrom JA, Shiferaw Y, Chen W, et al. Variability in timing of spontaneous calcium release in the intact rat heart is determined by the time course of sarcoplasmic reticulum calcium load. Circ Res 2010;107(9):1117-26.

Weerasooriya R, Khairy P, Litalien J, et al. Catheter ablation for atrial fibrillation: are results maintained at 5 years of follow-up? J Am Coll Cardiol 2011;57(2):160-6.

Yeh Y-H, Wakili R, Qi X-Y, et al. Calcium-Handling Abnormalities Underlying Atrial Arrhythmogenesis and Contractile Dysfunction in Dogs With Congestive Heart Failure. Circ Arrhythm Electrophysiol 2008;1:93-102.

Yeh YH, Kuo CT, Chan TH, et al. Transforming growth factor-β and oxidative stress mediate tachycardia-induced cellular remodelling in cultured atrial-derived myocytes. Cardiovasc Res 2011;91:62-70.

Yeh YH, Kuo CT, Chang GJ, Qi XY, Nattel S, Chen WJ. Nicotinamide adenine dinucleotide phosphate oxidase 4 mediates the differential responsiveness of atrial versus ventricular fibroblasts to transforming growth factor-β. Circ Arrhythm Electrophysiol 2013;6:790-8.

Youn J-Y, Zhang J, Zhang Y, et al. Oxidative stress in atrial fibrillation: An emerging role of NADPH oxidase. Journal of Molecular and Cellular Cardiology 2013;62:72-9.

Zhang P, Hou M, Li Y, et al. NADPH oxidase contributes to coronary endothelial dysfunction in the failing heart. Am J Physiol Heart Circ Physiol 2009;296:H840-6.

Zhang M, Brewer AC, Schroder K, et al. NADPH oxidase-4 mediates protection against chronic load-induced stress in mouse hearts by enhancing angiogenesis. Proc Natl Acad Sci U S A 2010;10(42):18121-6.

Zhang J, Youn JY, Kim A, et al. NOX4-dependent Hydrogen Peroxide Overproduction in Human Atrial Fibrillation and HL-1 Atrial Cells: Relationship to Hypertension. Frontiers in Physiology 2012;3.

Zhang M, Perino A, Ghigo A, Hirsch E, Shah AM. NADPH oxidases in heart failure: poachers or gamekeepers? Antioxid Redox Signal 2013;18(9):1024-41.

Zima AV, Blatter LA. Redox regulation of cardiac calcium channels and transporters. Cardiovascular Research 2006;71:310-21.

International Search Report and Written Opinion from PCT/US14/65834 dated Apr. 30, 2015, 22 pages.

Kuroda J, Ago T, Matsushima S, Zhai P, Schneider MD, Sadoshima J. NADPH oxidase 4 (Nox4) is a major source of oxidative stress in the failing heart. Proc Natl Acad Sci U S A 2010;107(35):15565-70.

Custer GM, Lancet S, Zhang J, et al. Redox-mediated reciprocal regulation of SERCA and Na+-Ca2+ exchanger contributes to sarcoplasmic reticulum Ca2+ depletion in cardiac myocytes. Free Radical Biology & Medicine 2010;48:1182-7.

Lakshminarayan K, Anderson DC, Herzog CA, Qureshi AL. Clinical epidemiology of atrial fibrillation and related cerebrovascular events in the United States. The Neurologist 2008;14:143-50.

Lammers WJ, Schalij MJ, Kirchhof CJ, Allessie MK Quantification of spatial inhomogeneity in conduction and initiation of reentrant atrial arrhythmias. Am J Physiol Soc. 1990;259:H1254-63.

Lau DH, Maesen B, Zeemering S, Verheule S, Crijns HJ, Schotten U. Stability of complex fractionated atrial electrograms: a systematic review. J Cardiovasc Electrophysiol 2012;23:980-7.

Laurita KR, Rosenbaum DS. Mechanisms and potential therapeutic targets for ventricular arrhythmias associated with impaired cardiac calcium cycling. J Mol Cell Cardiol 2008;44:31-43.

Laurita KR, Rosenbaum DS. Cellular mechanisms of arrhythmogenic cardiac alternans. Prog Biophys Mol Biol 2008;97:332-47.

Li D, Fareh S, Leung TK, Nattel S. Promotion of atrial fibrillation by heart failure in dogs: atrial remodeling of a different sort. Circulation 1999;100:87-95.

Li D, Melnyk P, Feng J, et al. Effects of Experimental Heart Failure on Atrial Cellular and Ionic Electrophysiology. Circulation 2000;101:2631-8.

Lijnen PJ, van Pelt JF, Fagard RH. Stimulation of reactive oxygen species and collagen synthesis by angiotensin II in cardiac fibroblasts. Cardiovascular therapeutics 2012;30:e1-8.

Lin YJ, Tai CT, Kao T, et al. Consistency of complex fractionated atrial electrograms during atrial fibrillation. Heart Rhythm 2008;5:406-12.

Lip GY, Kakar P, Watson T. Atrial fibrillation—the growing epidemic[comment]. Heart 2007;93:542-3.

Luo A, Ma J, Zhang P, Zhou H, Wang W. Sodium Channel Gating Modes During Redox Reaction. Cellular Physiology and Biochemistry 2007;19:9-20.

Maejima Y, Kuroda J, Matsushima S, Ago T, Sadoshima J. Regulation of myocardial growth and death by NADPH oxidase. J Mol Cell Cardiol 2011;50(3):408-16.

Marx SO, Marks AR Dysfunctional ryanodine receptors in the heart: new insights into complex cardiovascular diseases. J Mol Cell Cardiol 2013;58:225-31.

Maulik SK, Kumar S. Oxidative stress and cardiac hypertrophy: a review. IIOABJ 2011; 2(6):107-113.

Morrison T, Jared Bunch T, Gersh BJ. Pathophysiology of concomitant atrial fibrillation and heart failure: implications for management. Nat Clin Pract Cardiovasc Med 2009;6(1):46-56.

Murdoch CE, Zhang M, Cave AC, Shah AM. NADPH oxidase-dependent redox signalling in cardiac hypertrophy, remodelling and failure. Cardiovasc Res 2006;71:208-15.

Nabeebaccus A, Zhang M, Shah AM. NADPH oxidases and cardiac remodelling. Heart Fail Rev 2011;16:5-12.

Nademanee K, McKenzie J, Kosar E, et al. A new approach for catheter ablation of atrial fibrillation: mapping of the electrophysiologic substrate.[see comment]. Journal of the American College of Cardiology 2004;43(11):2044-53.

Nademanee K, Schwab MC, Kosar EM, et al. Clinical outcomes of catheter substrate ablation for high-risk patients with atrial fibrillation. Journal of the American College of Cardiology 2008;51(8):843-9.

(56) References Cited

OTHER PUBLICATIONS

Nattel S, Shiroshita-Takeshita A, Brundel BJ, Rivard L. Mechanisms of atrial fibrillation: lessons from animal models. Progress in Cardiovascular Diseases 2005;48(1):9-28.
Nattel S, Burstein B, Dobrev D. Atrial remodeling and atrial fibrillation: mechanisms and implications. Circ Arrhythm Electrophysiol 2008;1:62-73.
Nattel S. From guidelines to bench: implications of unresolved clinical issues for basic investigations of atrial fibrillation mechanisms. Can J Cardiol 2011;27:19-26.
Nediani C, Raimondi L, Borchi E, Cerbai E. Nitric Oxide/Reactive Oxygen Species Generation and Nitroso/Redox Imbalance in Heart Failure: From Molecular Mechanisms to Therapeutic Implications. Antioxidants & Redox Signaling 2011;14(2):289-331.
Ng J, Goldberger JJ. Understanding and interpreting dominant frequency analysis of AF electrograms. J Cardiovasc Electrophysiol 2007;18:680-5.
Ng J, Kadish AH, Goldberger JJ. Technical considerations for dominant frequency analysis. J Cardiovasc Electrophysiol 2007;18(6):757-64.
Ng J, Borodyanskiy AL, Chang ET, et al. Measuring the Complexity of Atrial Fibrillation Electrograms. J. Cardiovasc. Electrophysiol. 2010;21:649-55.
Ng J, Villuendas R, Cokic I, et al. Autonomic remodeling in the left atrium and pulmonary veins in heart failure: creation of a dynamic substrate for atrial fibrillation. Circ Arrhythm Electrophysiol 2011;4:388-96.
Niggli E, Ullrich ND, Gutierrez D, Kyrychenko S, Polakova E, Shirokova N. Posttranslational modifications of cardiac ryanodine receptors: Ca(2+) signaling and EC-coupling. Biochim Biophys Acta 2013;1833:866-75.
Pappone C, Oral H, Santinelli V, et al. Atrio-esophageal fistula as a complication of percutaneous transcatheter ablation of atrial fibrillation. Circulation 2004;109:2724-6.
Po SS, Scherlag BJ, Yamanashi WS, et al. Experimental model for paroxysmal atrial fibrillation arising at the pulmonary vein-atrial junctions.[see comment]. Heart Rhythm 2006;3:201-8.
Purohit A, Rokita AG, Guan X, et al. Oxidized Ca2+/Calmodulin-Dependent Protein Kinase II Triggers Atrial Fibrillation. Circulation 2013;128:1748-57.
Reilly SN, Jayaram R, Nahar K, et al. Atrial sources of reactive oxygen species vary with the duration and substrate of atrial fibrillation: implications for the antiarrhythmic effect of statins. Circulation 2011;124:1107-17.
Rodrigues AC, Scannavacca MI, Caldas MA, et al. Left atrial function after ablation for paroxysmal atrial fibrillation. Am. J. Cardiol. 2009;103:395-8.
Scherr D, Dalal D, Cheema A, et al. Long- and short-term temporal stability of complex fractionated atrial electrograms in human left atrium during atrial fibrillation. J Cardiovasc Electrophysiol 2009;20:13-21.
Schotten U, Verheule S, Kirchhof P, Goette A. Pathophysiological mechanisms of atrial fibrillation: a translational appraisal. Physiol Rev 2011;91:265-325.
Shinagawa K, Derakhchan K, Nattel S. Pharmacological prevention of atrial tachycardia induced atrial remodeling as a potential therapeutic strategy. Pacing Clin Electrophysiol 2003;26:752-64.
Shryock JC, Song Y, Rajamani S, Antzelevitch C, Belardinelli L. The arrhythmogenic consequences of increasing late INa in the cardiomyocyte. Cardiovasc Res 2013;99:600-11.
Somasuntharam et al., Delivery of Nox2-NADPH oxidase siRNA with polyketal nanoparticles for improving cardiac function following myocardial infarction, Biomaterials 2013;34:7790-8. Epub Jul. 13, 2013.
Song Y, Shryock JC, Belardinelli L. An increase of late sodium current induces delayed 1afterdepolarizations and sustained triggered activity in atrial myocytes. Am. J. Physiol. Heart Circ. Physiol. 2008;294:H2031-H9.

Sridhar A, Nishijima Y, Terentyev D, et al. Chronic heart failure and the substrate for atrial fibrillation. Cardiovascular Research 2009;84:227-36.
Swaminathan PD, Purohit A, Hund TJ, Anderson ME. Calmodulin-dependent protein kinase II: linking heart failure and arrhythmias. Circ Res 2012;110:1661-77.
Taylor GW, Kay GN, Zheng X, Bishop S, Ideker RE. Pathological effects of extensive radiofrequency energy applications in the pulmonary veins in dogs. Circulation 2000;101:1736-42.
Terentyev D, Gyorke I, Belevych AE, et al. Redox Modification of Ryanodine Receptors Contributes to Sarcoplasmic Reticulum Ca2+ Leak in Chronic Heart Failure. Circ. Res. 2008;103:1466-72.
Tsai KH, Wang WJ, Lin CW, et al. NADPH oxidase-derived superoxide anion-induced apoptosis is mediated via the JNK-dependent activation of NFκB in cardiomyocytes exposed to high glucose. J Cell Physiol 2012;227:1347-57.
Undrovinas N, Maltsev V, Belardinelli L, Sabbah H, Undrovinas A. Late sodium current contributes to diastolic cell Ca2+ accumulation in chronic heart failure. J. Physiol. Sci. 2010;60:245-57.
Valdivia CR, Chu WW, Pu J, et al. Increased late sodium current in myocytes from a canine heart failure model and from failing human heart. Journal of Molecular and Cellular Cardiology 2005;38:475-83.
Verma A, Patel D, Famy T, et al. Efficacy of adjuvant anterior left atrial ablation during intracardiac echocardiography-guided pulmonary vein antrum isolation for atrial fibrillation. J Cardiovasc Electrophysiol 2007;18:151-6.
Vescovo G, Ravara B, Dalla Libera L. Skeletal muscle myofibrillar protein oxidation and exercise capacity in heart failure. Basic Res Cardiol 2008;103:285-90.
Communication regarding extended European search report dated Aug. 17, 2017 for EP14861204.7, 15 pages.
Shin, et al., "Targeted Inhibition of NADPH Oxidase in the Posterior Left Atrium by Nox2 shRNA Decreases Formation of Atrial Fibrillation Substrate in Heart Failure", XP002771922, Database accession No. PREV201400366794 & *abstract* Circulation vol. 128, No. 22, Suppl. S., Nov. 2013 (Nov. 2013), p. 15234, Scientific Sessions and Resuscitation Science Symposium of the American-Heart-Association; Dallas, TX US; Nov. 16-17, 2013, 2 pages.
Reilly, Svetlana N., et al., "Atrial sources of reactive oxygen species vary with the duration and substrate of atrial fibrillation: implications for the antiarrhythmic effect of statins", Circulation Sep. 6, 2011 (Sep. 6, 2011), pp. 1107-1117, XP055389677, United States, DOI: 10.1161/Circulationaha.111.029223 Retrieved from the internet: URL: http://circ.ahajournals.org/contentcirculationaha/134/10/1107.full.pdf?download=true *abstract*.
Zhang, Yi-shuai, et al., "A novel pathway of NADPH oxidase/vascular peroxidase 1 in mediating oxidative injury following ischemia-reperfusion", Basic Research in Cardiology, vol. 107, No. 3, Apr. 3, 2012 (Apr. 3, 2012), pp. 1-19, XP035054559, Steinkopff-Verlag, DA ISSN: 1435-1803, DOI: 10.1007/S00395-012-0266-4 * page 5, right hand column*.
Patel, V.B., et al., "Cardioprotective Effects Mediated by angiotensis II Type 1 Receptor Blockade and Enhancing Angiotensin 1-7 in Experimental Heart Failure in Angiotensin-Converting Enzyme 2-Null Mice", Hypertension, vol. 59, No. 6, Jun. 1, 2012 (Jun. 1, 2012), pp. 1195-1203, XP055389674, US ISSN: 0194-911X., DOI: 10.1161/hyptertensionaha.112.191650 *abstract*.
Youn, Ji-Youn, et al., "Oxidative stress in atrial fibrillation: An emerging role of NADPH oxidase", Journal of Molecular and Cellular Cardiology., vol. 62, Sep. 1, 2013 (Sep. 1, 2013), pp. 72-79, XP05538631, GB ISSN: 0022-2828, DOI: 10.1016/j.yjmcc.2013.04.019.
Streeter., J., et al., "Opportunity Nox: The Future of NADPH Oxidases as Therapeutic Targets in Cardiovascular Disease", Cardiovascular Therapeutics, vol. 31, No. 3, Jan. 26, 2012 (Jan. 26, 2012), pp. 125-137, XP055388717, ISSN: 1755-5914, DOI: 10.1111/j.1755-5922.2011.00310.x.

\* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
tatccatttc caagtcatag g                                         21

<210> SEQ ID NO 2
<211> LENGTH: 7084
<212> TYPE: DNA
<213> ORGANISM: Artificial Sequence
<220> FEATURE:
<223> OTHER INFORMATION: Recombinant DNA Expression Vector

<400> SEQUENCE: 2
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
```

```
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac cctttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcggggagaa    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatc   1800
acgagactag cctcgagcgg ccgccccctt caccgagggc ctatttccca tgattccttc   1860
atatttgcat atacgataca aggctgttag agagataatt ggaattaatt tgactgtaaa   1920
cacaaagata ttagtacaaa atacgtacg tagaaagtaa taatttcttg ggtagtttgc    1980
agttttaaaa ttatgtttta aaatggacta tcatatgctt accgtaactt gaaagtattt   2040
cgatttcttg ctttatata tcttgtggaa aggacgaaac accggtacaa cagccacaac   2100
gtctatctcg agatagacgt tgtggctgtt gtatttttga attctcgacc tcgagacaaa   2160
tggcagtatt catccacaat tttaaaagaa aaggggggat tggggggtac agtgcagggg   2220
aaagaatagt agacataata gcaacagaca tacaaactaa agaattacaa aaacaaatta   2280
caaaaattca aaattttcgg gtttattaca gggacagcag agatccactt tggccgcggc   2340
tcgagggggt tggggttgcg ccttttccaa ggcagcctg gtttgcgca gggacgcggc     2400 tgctctgggc gtggttccgg gaaacgcagc ggcgccgacc ctgggtctcg cacattcttc   2460
```

```
acgtccgttc gcagcgtcac ccggatcttc gccgctaccc ttgtgggccc cccggcgacg    2520
cttcctgctc cgcccctaag tcgggaaggt tccttgcggt tcgcggcgtg ccggacgtga    2580
caaacggaag ccgcacgtct cactagtacc ctcgcagacg acagcgcca gggagcaatg     2640 gcagcgcgcc gaccgcgatg ggctgtggcc aatagcggct gctcagcagg gcgcgccgag    2700
agcagcggcc gggaaggggc ggtgcgggag gcggggtgtg gggcggtagt gtgggccctg    2760
ttcctgcccg cgcggtgttc cgcattctgc aagcctccgg agcgcacgtc ggcagtcggc    2820
tccctcgttg accgaatcac cgacctctct ccccaggggg atccaccgga gcttaccatg    2880
accgagtaca agcccacggt gcgcctcgcc accgcgacg acgtcccag ggccgtacgc      2940 accctcgccg ccgcgttcgc cgactacccc gccacgcgcc acaccgtcga tccggaccgc    3000
cacatcgagc gggtcaccga gctgcaagaa ctcttcctca cgcgcgtcgg gctcgacatc    3060
ggcaaggtgt gggtcgcgga cgacggcgcc gcggtggcgg tctggaccac gccggagagc    3120
gtcgaagcgg gggcggtgtt cgccgagatc ggcccgcgca tggccgagtt gagcggttcc    3180
cggctggccg cgcagcaaca gatggaaggc ctcctggcgc cgcaccggcc caaggagccc    3240
gcgtggttcc tggccaccgt cggcgtctcg cccgaccacc agggcaaggg tctgggcagc    3300
gccgtcgtgc tccccggagt ggaggcggcc gagcgcgccg gggtgccgc cttcctggag     3360 acctccgcgc cccgcaacct ccccttctac gagcggctcg gcttcaccgt caccgccgac    3420
gtcgaggtgc ccgaaggacc gcgcacctgg tgcatgaccc gcaagcccgg tgcctgacgc    3480
ccgccccacg acccgcagcg cccgaccgaa aggagcgcac gacccatgc atcggtacct     3540 ttaagaccaa tgacttacaa ggcagctgta gatcttagcc acttttaaa agaaaagggg     3600 ggactggaag ggctaattca ctcccaacga agacaagatc tgcttttgc ttgtactggg     3660 tctctctggt tagaccagat ctgagcctgg gagctctctg gctaactagg gaacccactg    3720
cttaagcctc aataaagctt gccttgagtg cttcaagtag tgtgtgcccg tctgttgtgt    3780
gactctggta actagagatc cctcagaccc ttttagtcag tgtggaaaat ctctagcagt    3840
agtagttcat gtcatcttat tattcagtat ttataacttg caaagaaatg aatatcagag    3900
agtgagagga acttgtttat tgcagcttat aatggttaca aataaagcaa tagcatcaca    3960
aatttcacaa ataaagcatt ttttcactg cattctagtt gtggtttgtc caaactcatc     4020
aatgtatctt atcatgtctg gctctagcta tcccgcccct aactccgccc atcccgcccc    4080
taactccgcc cagttccgcc cattctccgc cccatggctg actaatttt tttatttatg     4140 cagaggccga ggcgcctcg gcctctgagc tattccagaa gtagtgagga ggcttttttg     4200
gaggcctagg gacgtaccca attcgcccta tagtgagtcg tattacgcgc gctcactggc    4260
cgtcgtttta caacgtcgtg actgggaaaa ccctggcgtt acccaactta atcgccttgc    4320
agcacatccc cctttcgcca gctggcgtaa tagcgaagag gcccgcaccg atcgcccttc    4380
ccaacagttg cgcagcctga atggcgaatg ggacgcgccc tgtagcggcg cattaagcgc    4440
ggcgggtgtg gtggttacgc gcagcgtgac cgctacactt gccagcgccc tagcgcccgc    4500
tcctttcgct ttcttccctt cctttctcgc cacgttcgcc ggctttcccc gtcaagctct    4560
aaatcggggg ctccctttag ggttccgatt tagtgcttta cggcacctcg accccaaaaa    4620
acttgattag ggtgatggtt cacgtagtgg gccatcgccc tgatagacgg ttttcgccc    4680 tttgacgttg gagtccacgt tctttaatag tggactcttg ttccaaactg gaacaacact    4740
caaccctatc tcggtctatt cttttgattt ataaggatt tgccgatttc ggcctattg     4800 gttaaaaaat gagctgattt aacaaaaatt taacgcgaat tttaacaaaa tattaacgct    4860
```

```
tacaatttag gtggcacttt tcggggaaat gtgcgcggaa cccctatttg tttattttc    4920 taaatacatt caaatatgta tccgctcatg agacaataac cctgataaat gcttcaataa    4980
tattgaaaaa ggaagagtat gagtattcaa catttccgtg tcgcccttat tcccttttt    5040 gcggcatttt gccttcctgt ttttgctcac ccagaaacgc tggtgaaagt aaaagatgct    5100
gaagatcagt tgggtgcacg agtgggttac atcgaactgg atctcaacag cggtaagatc    5160
cttgagagtt ttcgccccga agaacgtttt ccaatgatga gcacttttaa agttctgcta    5220
tgtggcgcgg tattatcccg tattgacgcc gggcaagagc aactcggtcg ccgcatacac    5280
tattctcaga atgacttggt tgagtactca ccagtcacag aaaagcatct tacggatggc    5340
atgacagtaa gagaattatg cagtgctgcc ataaccatga gtgataacac tgcggccaac    5400
ttacttctga caacgatcgg aggaccgaag gagctaaccg cttttttgca acatgggg     5460 gatcatgtaa ctcgccttga tcgttgggaa ccggagctga atgaagccat accaaacgac    5520
gagcgtgaca ccacgatgcc tgtagcaatg gcaacaacgt tgcgcaaact attaactggc    5580
gaactactta ctctagcttc ccggcaacaa ttaatagact ggatggaggc ggataaagtt    5640
gcaggaccac ttctgcgctc ggcccttccg gctggctggt ttattgctga taaatctgga    5700
gccggtgagc gtgggtctcg cggtatcatt gcagcactgg ggccagatgg taagccctcc    5760
cgtatcgtag ttatctacac gacggggagt caggcaacta tggatgaacg aaatagacag    5820
atcgctgaga taggtgcctc actgattaag cattggtaac tgtcagacca agtttactca    5880
tatatacttt agattgattt aaaacttcat ttttaattta aaaggatcta ggtgaagatc    5940 cttttgata atctcatgac caaaatccct taacgtgagt tttcgttcca ctgagcgtca    6000
gaccccgtag aaaagatcaa aggatcttct tgagatcctt ttttctgcg cgtaatctgc     6060 tgcttgcaaa caaaaaaacc accgctacca gcggtggttt gtttgccgga tcaagagcta    6120
ccaactcttt ttccgaaggt aactggcttc agcagagcgc agataccaaa tactgttctt    6180
ctagtgtagc cgtagttagg ccaccacttc aagaactctg tagcaccgcc tacatacctc    6240
gctctgctaa tcctgttacc agtggctgct gccagtggcg ataagtcgtg tcttaccggg    6300
ttggactcaa gacgatagtt accggataag gcgcagcggt cgggctgaac ggggggttcg    6360
tgcacacagc ccagcttgga gcgaacgacc tacaccgaac tgagatacct acagcgtgag    6420
ctatgagaaa gcgccacgct tcccgaaggg agaaaggcgg acaggtatcc ggtaagcggc    6480
agggtcggaa caggagagcg cacgagggag cttccagggg gaaacgcctg gtatctttat    6540
agtcctgtcg ggtttcgcca cctctgactt gagcgtcgat ttttgtgatg ctcgtcaggg    6600
gggcggagcc tatggaaaaa cgccagcaac gcggccttt tacggttcct ggccttttgc    6660
tggccttttg ctcacatgtt ctttcctgcg ttatcccctg attctgtgga taaccgtatt    6720
accgcctttg agtgagctga taccgctcgc cgcagccgaa cgaccgagcg cagcgagtca    6780
gtgagcgagg aagcggaaga gcgcccaata cgcaaaccgc ctctccccgc gcgttggccg    6840
attcattaat gcagctggca cgacaggttt cccgactgga aagcgggcag tgagcgcaac    6900
gcaattaatg tgagttagct cactcattag gcaccccagg ctttacactt tatgcttccg    6960
gctcgtatgt tgtgtggaat tgtgagcgga taacaatttc acacaggaaa cagctatgac    7020
catgattacg ccaagcgcgc aattaaccct cactaaaggg aacaaaagct ggagctgcaa    7080
gctt                                                                7084
```

INHIBITION OF OXIDATIVE STRESS IN ATRIAL FIBRILLATION

CROSS-REFERENCE TO RELATED APPLICATIONS

This application claims benefit of priority under 35 U.S.C. 119 to U.S. provisional patent application Ser. No. 61/904,925, filed Nov. 15, 2013, and entitled "INHIBITION OF OXIDATIVE STRESS IN ATRIAL FIBRILLATION," the contents of which are herein incorporated by reference in its entirety.

SEQUENCE LISTING

The instant application contains a Sequence Listing that has been submitted in ASCII format via EFS-Web and is hereby incorporated by reference in its entirety. Said ASCII copy, created on Apr. 5, 2015, is named NWN01-076-US_ST25.txt, and is 9,927 bytes in size.

STATEMENT REGARDING FEDERALLY SPONSORED RESEARCH OR DEVELOPMENT

This invention was made with government support under 1R01HL093490 awarded by the National Institutes of Health. The government has certain rights in the invention.

FIELD OF INVENTION

The present disclosure relates to compositions and methods for preventing certain cardiac damage. In particular, compositions and methods of inhibiting oxidative stress in a subject suffering from atrial fibrillation is provided.

BACKGROUND

Atrial Fibrillation (AF) is the most common heart rhythm disorder (Benjamin E J, Levy D, Vaziri S M, D'Agostino R B, Belanger A J, Wolf P A. "Independent risk factors for atrial fibrillation in a population-based cohort. The Framingham Heart Study," *JAMA* 1994; 271:840-4), and is a major risk factor for stroke and HF (Balasubramaniam R, Kistler P M. AF and "Heart failure: the chicken or the egg?" *Heart* 2009; 95:535-9; Lakshminarayan K, Anderson D C, Herzog C A, Qureshi A I. "Clinical epidemiology of atrial fibrillation and related cerebrovascular events in the United States," *Neurologist* 2008; 14:143-50; Lip G Y, Kakar P, Watson T. "Atrial fibrillation—the growing epidemic" [comment], *Heart* 2007; 93:542-3). Since a majority of AF triggers arise in the pulmonary veins (PVs) and the adjoining posterior left atrium (PLA), ablation procedures that electrically isolate the PVs have emerged in recent years as a viable therapy for focal AF. Nonetheless, moderately high ablation success rates have only been achieved in selected patients (Nademanee K, McKenzie J, Kosar E et al. "A new approach for catheter ablation of atrial fibrillation: mapping of the electrophysiologic substrate" [see comment], *J. Am. Coll. Cardiol.* 2004; 43:2044-53; Nademanee K, Schwab M C, Kosar E M et al. "Clinical outcomes of catheter substrate ablation for high-risk patients with atrial fibrillation," *J. Am. Coll. Cardiol.* 2008; 51:843-9; Taylor G W, Kay G N, Zheng X, Bishop S, Ideker R E. "Pathological effects of extensive radiofrequency energy applications in the pulmonary veins in dogs," *Circulation* 2000; 101:1736-42). Indeed, in patients with structural heart disease e.g. heart failure (HF), success rates do not exceed 50-60% (Estner H L, Hessling G, Ndrepepa G et al. "Electrogram-guided substrate ablation with or without pulmonary vein isolation in patients with persistent atrial fibrillation," *Europace* 2008; 10:1281-7; Weerasooriya R, Khairy P, Litalien J et al. "Catheter ablation for atrial fibrillation: are results maintained at 5 years of follow-up?" *J. Am. Coll. Cardiol.* 2011; 57:160-6). One reason for this low efficacy is that current ablation strategies primarily employ an anatomical, 'one-size fits all' strategy (with some minor variations) that does not address the specific mechanisms underlying AF (Ben Morrison T, Jared Bunch T, Gersh B J. "Pathophysiology of concomitant atrial fibrillation and heart failure: implications for management," *Nat. Clin. Pract. Cardiovasc. Med.* 2009; 6:46-56). Recent research has therefore attempted to better define the mechanisms underlying AF, in order to improve upon the success of ablation and to develop new biological therapies for AF.

In the setting of structural heart disease—specifically HF—a variety of mechanisms e.g. stretch, oxidative stress (OS), autonomic imbalance and structural changes such as fibrosis are thought to contribute to a vulnerable AF substrate (Nattel S. "From guidelines to bench: implications of unresolved clinical issues for basic investigations of atrial fibrillation mechanisms," *Can. J. Cardiol.* 2011; 27:19-26; Nattel S, Burstein B, Dobrev D. "Atrial remodeling and atrial fibrillation: mechanisms and implications," *Circ. Arrhythm. Electrophysiol.* 2008; 1:62-73). OS is known to be elevated in the atria in AF (Youn J Y, Zhang J, Zhang Y et al. "Oxidative stress in atrial fibrillation: an emerging role of NADPH oxidase," *J. Mol. Cell. Cardiol.* 2013; 62:72-9) and reactive oxygen species (ROS) have effects on the atrial action potential and $Ca^{2+}$ cycling. However, the precise effects of ROS on atrial electrophysiology in the intact atria—and how these electrophysiological changes contribute to formation of AF substrate—are not known.

Oxygen derivatives with instabilities and increased reactivity, e.g. $O_2$, $H_2O_2$, and OH, are generically termed ROS (Maejima Y, Kuroda J, Matsushima S, Ago T, Sadoshima J. "Regulation of myocardial growth and death by NADPH oxidase," *J. Mol. Cell. Cardiol.* 2011; 50:408-16). While ROS at low doses mediates physiological functions such as growth, differentiation, metabolism (id.), excess ROS damages DNA, protein and lipids, and causes cell death (id.). A wealth of research points to increased OS as a key driver of cardiac remodeling caused by chronic pressure overload, loss of functional myocardium or AF (Kohlhaas M, Maack C. "Interplay of defective excitation-contraction coupling, energy starvation, and oxidative stress in heart failure," *Trends Cardiovasc. Med.* 2011; 21:69-73; Maulik S K, Kumar S. "Oxidative stress and cardiac hypertrophy: a review," *Toxicol. Mech. Methods* 2012; 22:359-66). In addition, chronic ROS elevation activates signaling pathways such as TGF-1, MAP kinase subfamilies (Hori M, Nishida K. "Oxidative stress and left ventricular remodelling after myocardial infarction," *Cardiovas. Res.* 2009; 81:457-64; Tsai K H, Wang W J, Lin C W et al. "NADPH oxidase-derived superoxide anion-induced apoptosis is mediated via the JNK-dependent activation of NF-kappaB in cardiomyocytes exposed to high glucose," *J. Cell. Physiol.* 2012; 227:1347-57) that result in structural changes e.g. fibrosis. Moreover, ROS generation (e.g. by Ang II mediated NOX activation) has been shown to lead to modifications of CaMKII (Erickson J R, He B J, Grumbach I M, Anderson M E. "CaMKII in the cardiovascular system: sensing redox states," *Physiol. Rev.* 2011; 91:889-915), an important serine-threonine kinase involved in a variety of E-C coupling related processes in cardiac myocytes.

ROS are generated by the mitochondrial electron transport chain, the xanthine oxidase/dehydrogenase system, 'uncoupled' NOS, cytochrome P450 and NADPH oxidases. The NADPH oxidase enzyme family are a major source of cardiovascular ROS (Murdoch C E, Zhang M, Cave A C, Shah A M. "NADPH oxidase-dependent redox signalling in cardiac hypertrophy, remodelling and failure," *Cardiovasc. Res.* 2006; 71:208-15; Cave A C, Brewer A C, Narayanapanicker A et al. "NADPH oxidases in cardiovascular health and disease," *Antioxid. Redox. Signal.* 2006; 8:691-728) with NOX2 being the dominant ROS-generating NADPH isoform in HF (Nabeebaccus A, Zhang M, Shah A M. "NADPH oxidases and cardiac remodeling," *Heart Fail. Rev.* 2011; 16:5-12; Maejima Y, Kuroda J, Matsushima S, Ago T, Sadoshima J. "Regulation of myocardial growth and death by NADPH oxidase," *J Mol. Cell. Cardiol.* 2011; Cave A C, Brewer A C, Narayanapanicker A et al. "NADPH oxidases in cardiovascular health and disease," *Antioxid. Redox. Signal.* 2006; 8:691-728; Zhang P, Hou M, Li Y et al. "NADPH oxidase contributes to coronary endothelial dysfunction in the failing heart," *Am. J. Physiol. Heart. Circ. Physiol.* 2009; 296:H840-6; Dworakowski R, Alom-Ruiz S P, Shah A M. "NADPH oxidase-derived reactive oxygen species in the regulation of endothelial phenotype," *Pharmacol. Rep.* 2008; 60:21-8). However, more recent studies indicate that NOX4 in mitochondria plays an essential role in mediating OS during pressure overload-induced cardiac hypertrophy (Nabeebaccus A, Zhang M, Shah A M. "NADPH oxidases and cardiac remodeling," *Heart Fail. Rev.* 2011; 16:5-12; Kuroda J, Ago T, Matsushima S, Zhai P, Schneider M D, Sadoshima J. "NADPH oxidase 4 (Nox4) is a major source of oxidative stress in the failing heart," *Proc. Natl. Acad. Sci. U.S.A.* 2010; 107:15565-70; Zhang M, Brewer A C, Schroder K et al. "NADPH oxidase-4 mediates protection against chronic load-induced stress in mouse hearts by enhancing angiogenesis," *Proc. Natl. Acad. Sci. U.S.A.* 2010; 107:18121-6) NOX4 also appears to contribute significantly to the formation of fibrosis; in addition, it appears to be activated by pro-fibrotic signaling pathways e.g. TGF-β (Yeh Y H, Kuo C T, Chang G J, Qi X Y, Nattel S, Chen W J. "Nicotinamide adenine dinucleotide phosphate oxidase 4 mediates the differential responsiveness of atrial versus ventricular fibroblasts to transforming growth factor-beta," *Circ. Arrhythm. Electrophysiol.* 2013; 6:790-8; Zhang M, Perino A, Ghigo A, Hirsch E, Shah A M. "NADPH oxidases in heart failure: poachers or gamekeepers?" *Antioxid. Redox. Signal.* 2013; 18:1024-41).

Recent evidence indicates that OS also contributes to structural and electrical remodeling in AF. Mihm et al. demonstrated significant oxidative damage in atrial appendages of AF patients undergoing the Maze procedure (Huang C X, Liu Y, Xia W F, Tang Y H, Huang H. Oxidative stress: a possible pathogenesis of atrial fibrillation. Med Hypotheses 2009; 72:466-7). Cames et al. showed that dogs with sustained AF had an increase in protein nitration, suggesting enhanced OS (Carnes C A, Janssen P M, Ruehr M L et al. "Atrial glutathione content, calcium current, and contractility," *J. Biol. Chem.* 2007; 282:28063-73; Cames C A, Chung M K, Nakayama T et al. "Ascorbate attenuates atrial pacing-induced peroxynitrite formation and electrical remodeling and decreases the incidence of postoperative atrial fibrillation," *Circ. Res.* 2001; 89:E32-8). Kim et al. showed that NADPH oxidase (NOX2) was a major source of atrial ROS in patients with AF (Kim Y M, Guzik T J, Zhang Y H et al. "A myocardial Nox2 containing NAD(P)H oxidase contributes to oxidative stress in human atrial fibrillation," *Circ. Res.* 2005; 97:629-36). More recently, Reilly et al. have shown that atrial sources of ROS vary with the duration and substrate of AF, with NADPH oxidase being elevated early in AF (e.g. with post-operative AF) and with mitochondrial oxidases and uncoupled NOS being noted in long standing AF (Reilly S N, Jayaram R, Nahar K et al. "Atrial sources of reactive oxygen species vary with the duration and substrate of atrial fibrillation: implications for the antiarrhythmic effect of statins," *Circulation* 2011; 124:1107-17). More recent data demonstrates that NOX4—which, as mentioned above, appears to contribute to the generation of mitochondrial ROS, specifically $H_2O_2$ (which more explicitly promotes fibrosis (Cucoranu I, Clempus R, Dikalova A et al. "NAD(P)H Oxidase 4 Mediates Transforming Growth Factor-1—Induced Differentiation of Cardiac Fibroblasts Into Myofibroblasts," *Circ. Res.* 2005; 97:900-7))—is also elevated in AF (Joun et al. (2013) supra; Zhang J, Youn J Y, Kim A et al. "NOX4-dependent Hydrogen Peroxide Overproduction in Human Atrial Fibrillation and HL-1 Atrial Cells: Relationship to Hypertension," *Front. Physiol.* 2012; 3)

The detrimental electrical effects of an enhanced, pathological late $I_{Na}$ include the following: (i) diastolic depolarization during phase 4 of the AP that may lead to spontaneous AP firing and abnormal automaticity, (ii) an increase of AP duration, which may lead to EADs and triggered activity, as well as increased spatiotemporal differences of repolarization time, which promote reentrant electrical activity; and (iii) the indirect effects of a late $I_{Na}$-induced increase of $Na^+$ entry to alter $Ca^{2+}$ homeostasis in myocytes, which may lead to $Ca^{2+}$ alternans and DADs. Acquired conditions and drugs that enhance late $I_{Na}$ are associated with atrial tachyarrhythmias, ventricular tachyarrhythmias including torsades de pointes (TdF), afterpotentials (EADs, DADs), and triggered activity (Shryock J C, Song Y, Rajamani S, Antzelevitch C, Belardinelli L. "The arrhythmogenic consequences of increasing late $I_{Na}$ in the cardiomyocyte," *Cardiovasc. Res.* 2013; 99:600-11). Recent investigations implicate a role for abnormal $Ca^{2+}$ handling in the genesis of ventricular and atrial arrhythmias (Aistrup G L, Balke C W, Wasserstrom J A. Arrhythmia triggers in heart failure: the smoking gun of $[Ca^{2+}]_i$ dysregulation," *Heart Rhythm.* 2011; 8:1804-8; Antoons G, Sipido K R. "Targeting calcium handling in arrhythmias," *Europace* 2008; 10:1364-9; Laurita K R, Rosenbaum D S. "Mechanisms and potential therapeutic targets for ventricular arrhythmias associated with impaired cardiac calcium cycling," *J. Mol. Cell. Cardiol.* 2008; 44:31-43). Abnormal $Ca^{2+}$ handling can contribute to arrhythmogenesis directly by triggering abnormal depolarizations and indirectly by modulating action potential time course and duration. DADs are typically result from cellular $Ca^{2+}$ overload, with SCR increasing forward NCX and producing an inward current resulting in DADs (Antoons et al. (2008) supra; Volders P G, Vos M A, Szabo B et al. "Progress in the understanding of cardiac early afterdepolarizations and torsades de pointes: time to revise current concepts," *Cardiovasc. Res.* 2000; 46:376-92). More recent evidence has accumulated for $Ca^{2+}$-mediated EADs (Volders et al. (2000) supra), which could contribute to triggered activity or at least prolong action potential duration. Indeed, abnormal $Ca^{2+}$ cycling and resulting $Ca^{2+}$ transient alternans predisposes to changes in the action potential that set up conditions for reentry (Laurita et al. (2008) supra). Abnormal SR $Ca^{2+}$ release has also been suggested to contribute to reentry in the intact atria, including the PVs (Chou C C, Nihei M, Zhou S et al. "Intracellular calcium dynamics and anisotropic reentry in isolated canine pulmonary veins and left atrium," *Circulation* 2005; 111:

2889-97). In HF, a number of atrial ion-channel and E-C coupling proteins (Li D, Melnyk P, Feng J et al. "Effects of Experimental Heart Failure on Atrial Cellular and Ionic Electrophysiology," *Circulation* 2000; 101:2631-8.61. Yeh Y-H, Wakili R, Qi X-Y et al. "Calcium-Handling Abnormalities Underlying Atrial Arrhythmogenesis and Contractile Dysfunction in Dogs With Congestive Heart Failure," *Circ. Arrhythm. Electrophysiol.* 2008; 1:93-102) can be modulated by ROS (Hool L C. "Reactive Oxygen Species in Cardiac Signalling: From Mitochondria to Plasma Membrane Ion Channels," *Clin. Exp. Pharm. Phys.* 2006; 33:146-51; Zima A V, Blatter L A. "Redox regulation of cardiac calcium channels and transporters," *Cardiovasc. Res.* 2006; 71:310-21; Nediani C, Raimondi L, Borchi E, Cerbai E. "Nitric Oxide/Reactive Oxygen Species Generation and Nitroso/Redox Imbalance in Heart Failure: From Molecular Mechanisms to Therapeutic Implications," *Antioxidants & Redox Signaling* 2011; 14:289-331) at least in part via ROS activation of kinases and inactivation of phosphatases, resulting in aberrant phosphorylation (e.g. of RyR2 and phospholamban). Also, ROS directly decrease SERCA function, but increase NCX function (Koster G M, Lancet S, Zhang J et al. "Redox-mediated reciprocal regulation of SERCA and $Na^+—Ca^{2+}$ exchanger contributes to sarcoplasmic reticulum $Ca^{2+}$ depletion in cardiac myocytes," *Free Rad. Biol. Med.* 2010; 48:1182-7) which parallels the changes in SERCA and NCX in HF. Additionally, ROS increases late/persistent $I_{Na}$($I_{Na}$_late) (Luo A, Ma J, Zhang P, Zhou H, Wang W. "Sodium Channel Gating Modes During Redox Reaction," *Cell. Phys. Bioch.* 2007; 19:9-20), which again parallels that in HF (Valdivia C R, Chu W W, Pu J et al. "Increased late sodium current in myocytes from a canine heart failure model and from failing human heart," *J. Mol. Cell. Cardiol.* 2005; 38:475-83) and $I_{Na}$, late can significantly contribute to the induction of EADs and DADs (Li D, Melnyk P, Feng J et al. "Effects of Experimental Heart Failure on Atrial Cellular and Ionic Electrophysiology," *Circulation* 2000; 101:2631-8; Song Y, Shryock J C, Belardinelli L. "An increase of late sodium current induces delayed afterdepolarizations and sustained triggered activity in atrial myocytes," *Am. J. Physiol.—Heart and Circ. Physiol.* 2008; 294:H2031-H9; Wasserstrom J A, Sharma R, O'Toole M J et al. "Ranolazine Antagonizes the Effects of Increased Late Sodium Current on Intracellular Calcium Cycling in Rat Isolated Intact Heart," *J. Pharm. Exp. Ther.* 2009; Undrovinas N, Maltsev V, Belardinelli L, Sabbah H, Undrovinas A. "Late sodium current contributes to diastolic cell Ca<sup>2+</sup> accumulation in chronic heart failure," *J. Physiol. Sci.* 2010; 60:245-57) both in ventricles and atria. Additional promotion of triggered activity could come from the increased $Ca^{2+}$ sensitivity of hyperphosphorylated RyR2s in HF (Terentyev D, Gyorke I, Belevych A E et al. "Redox Modification of Ryanodine Receptors Contributes to Sarcoplasmic Reticulum $Ca^{2+}$ Leak in Chronic Heart Failure," *Circ. Res.* 2008; 103:1466-72), which together with OS modifications of RyR2 (nitrosylation, oxidation) (Valdivia C R, Chu W W, Pu J et al. "Increased late sodium current in myocytes from a canine heart failure model and from failing human heart," *J. Mol. Cell. Card.* 2005; 38:475-83. 65. Song Y, Shryock J C, Belardinelli L. "An increase of late sodium current induces delayed afterdepolarizations and sustained triggered activity in atrial myocytes," *Am. J. Physiol. Heart Circ. Physiol.* 2008; 294:H2031-H9) in HF lead to leaky ventricular RyR2s (Gonzalez D R, Beigi F, Treuer A V, Hare J M. "Deficient ryanodine receptor 5-nitrosylation increases sarcoplasmic reticulum calcium leak and arrhythmogenesis in cardiomyocytes," *Proc. Natl. Acad. Sci. U.S.A.* 2007; 104:20612-7; Marx S O, Marks A R. "Dysfunctional ryanodine receptors in the heart: new insights into complex cardiovascular diseases," *J. Mol. Cell. Cardiol.* 2013; 58:225-31). The oxidation/nitrosylation state of atrial RyR2s in HF has not been fully scrutinized; however, there appear to be significant differences in atrial versus ventricular E-C coupling, as has previously been suggested by others (Bootman M D, Smymias I, Thul R, Coombes S, Roderick H L. "Atrial cardiomyocyte calcium signaling," *Biochim. Biophys. Acta* 2011; 1813:922-34). The majority of the studies mentioned above have been performed in isolated myocytes; the specific contribution oxidized $I_{Na}$, RyR2 to the electrophysiological characteristics of the intact atrium—and how this contributes to arrhythmogenesis—is not known.

Excessively activated CaMKII is implicated in the genesis of HF and arrhythmias. Recent evidence suggests that both CaMKII and $H_2O_2$ increase RyR2 (Marx S O, Marks A R. "Dysfunctional ryanodine receptors in the heart: new insights into complex cardiovascular diseases," *J. Mol. Cell. Cardiol.* 2013; 58:225-31; Niggli E, Ullrich N D, Gutierrez D, Kyrychenko S, Polakova E, Shirokova N. "Posttranslational modifications of cardiac ryanodine receptors: Ca(2+) signaling and EC-coupling," *Biochim. Biophys. Acta* 2013; 1833:866-75) $P_O$ (Undrovinas N, Maltsev V, Belardinelli L, Sabbah H, Undrovinas A. "Late sodium current contributes to diastolic cell Ca<sup>2+</sup> accumulation in chronic heart failure," *J. Physiol. Sci.* 2010; 60:245-57; Gonzalez D R, Beigi F, Treuer A V, Hare J M. "Deficient ryanodine receptor S-nitrosylation increases sarcoplasmic reticulum calcium leak and arrhythmogenesis in cardiomyocytes," *Proc. Natl. Acad. Sci. U.S.A.* 2007; 104:20612-7; Donoso P, Sanchez G, Bull R, Hidalgo C. "Modulation of cardiac ryanodine receptor activity by ROS and RNS," *Front. Biosci.* (Landmark Ed) 2011; 16:553-67; Terentyev D, Gyorke I, Belevych A E, et al. "Redox modification of ryanodine receptors contributes to sarcoplasmic reticulum $Ca^{2+}$ leak in chronic heart failure," *Circ. Res.* 2008; 103:1466-72), thereby promoting SR $Ca^2$ leak and arrhythmias (Belevych A E, Terentyev D, Terentyeva R et al. "Shortened $Ca^{2+}$ signaling refractoriness underlies cellular arrhythmogenesis in a postinfarction model of sudden cardiac death," *Circ. Res.* 2012; 110:569-77). Since OS-mediated oxidation of Met 281/282 residues in the regulatory domain of CaMKII transforms CaMKII into a constitutively active form (ox-CaMKII), leading to aberrant phosphorylation of multiple E-C coupling proteins (Swaminathan P D, Purohit A, Hund T J, Anderson M E. "Calmodulin-dependent protein kinase II: linking heart failure and arrhythmias," *Circ. Res.* 2012; 110:1661-77; Erickson J R, He B J, Grumbach I M, Anderson M E. "CaMKII in the cardiovascular system: sensing redox states," *Physiol. Rev.* 2011; 91:889-915), OS may affect $RyR_2P_O$ both directly (via ROS) and indirectly (via ox-CaMKII). Indeed, expression of ox-CaMKII has been found to be increased in atria of AF patients, indicating a potential role of ROS induced CaMKII activation in AF (Purohit A, Rokita A G, Guan X et al. "Oxidized Ca2+/Calmodulin-Dependent Protein Kinase II Triggers Atrial Fibrillation," *Circulation* 2013; 128:1748-57). CaMKII has also been shown to modulate the gating of $Na_V1.5$, at least in part by phosphorylation of $Na_V1.5$ at multiple sites (Ashpole N M, Herren A W, Ginsburg K S et al. "Ca2+/calmodulin-dependent protein kinase II (CaMKII) regulates cardiac sodium channel $Na_V1.5$ gating by multiple phosphorylation sites," *J. Biol. Chem.* 2012; 287:19856-69). A recent study demonstrates a fundamental requirement for targeting of CaMKII to a controlling phosphorylation site, 5571, on Na$_v$1.5 (Hund T J, Koval O M, Li J et al. "A beta(IV)-spectrin/CaMKII signaling complex is essential for membrane excitability in mice," *J. Clin. Invest.* 2010; 120:3508-19).

CaMKII phosphorylation of Na$_v$1.5 is thought to decrease transient I$_{Na}$, but increase I$_{Na,late}$, again thereby contributing to the genesis of triggered activity (Hashambhoy Y L, Winslow R L, Greenstein J L. "CaMKII-dependent activation of late INa contributes to cellular arrhythmia in a model of the cardiac myocyte," *Conf. Proc. IEEE Eng. Med. Biol. Soc.* 2011; 2011:4665-8). Modeling studies also suggest that ox-CaMKII may create substrate for reentry by regulating conduction characteristics of the myocardium (Hashambhoy et al. (2011) supra; Christensen M D, Dun W, Boyden P A, Anderson M E, Mohler P J, Hund T J. "Oxidized calmodulin kinase II regulates conduction following myocardial infarction: a computational analysis," *PLoS Comput. Biol.* 2009; 5:e1000583), with this substrate thought to be at least partially mediated by modulation of I$_{Na}$.

A summary of the various mechanisms for reactive oxygen species production, oxidative stress generation, and development of fibrosis and atrial fibrillation is illustrated in FIG. 1.

SUMMARY

In a first respect, a method of inhibiting oxidative stress in a subject having atrial or ventricular arrhythmias, ventricular failure or heart failure is provided. The method includes the step of administering an effective amount of a NOX2 inhibitor agent to the subject, wherein said administering is under conditions such that a level of oxidative stress in myocardial tissue is reduced or eliminated.

In a second respect, a method of treating a subject having atrial or ventricular arrhythmias, ventricular failure or heart failure is provided. The method includes the step of administering an effective amount of a NOX2 inhibitor agent to the subject, wherein said administering is under conditions such that a level of atrial or ventricular arrhythmias is reduced or eliminated.

In a third respect, a pharmaceutical composition for inhibiting oxidative stress in a subject having atrial or ventricular arrhythmias, ventricular failure or heart failure is provided. The pharmaceutical composition includes an isolated nucleic acid encoding a small hairpin RNA against NOX2 mRNA (NOX2 rhRNA).

These and other features, objects and advantages of the present invention will become better understood from the description that follows. In the description, reference is made to the accompanying drawings, which form a part hereof and in which there is shown by way of illustration, not limitation, embodiments of the invention.

DETAILED DESCRIPTION

Figure 1:
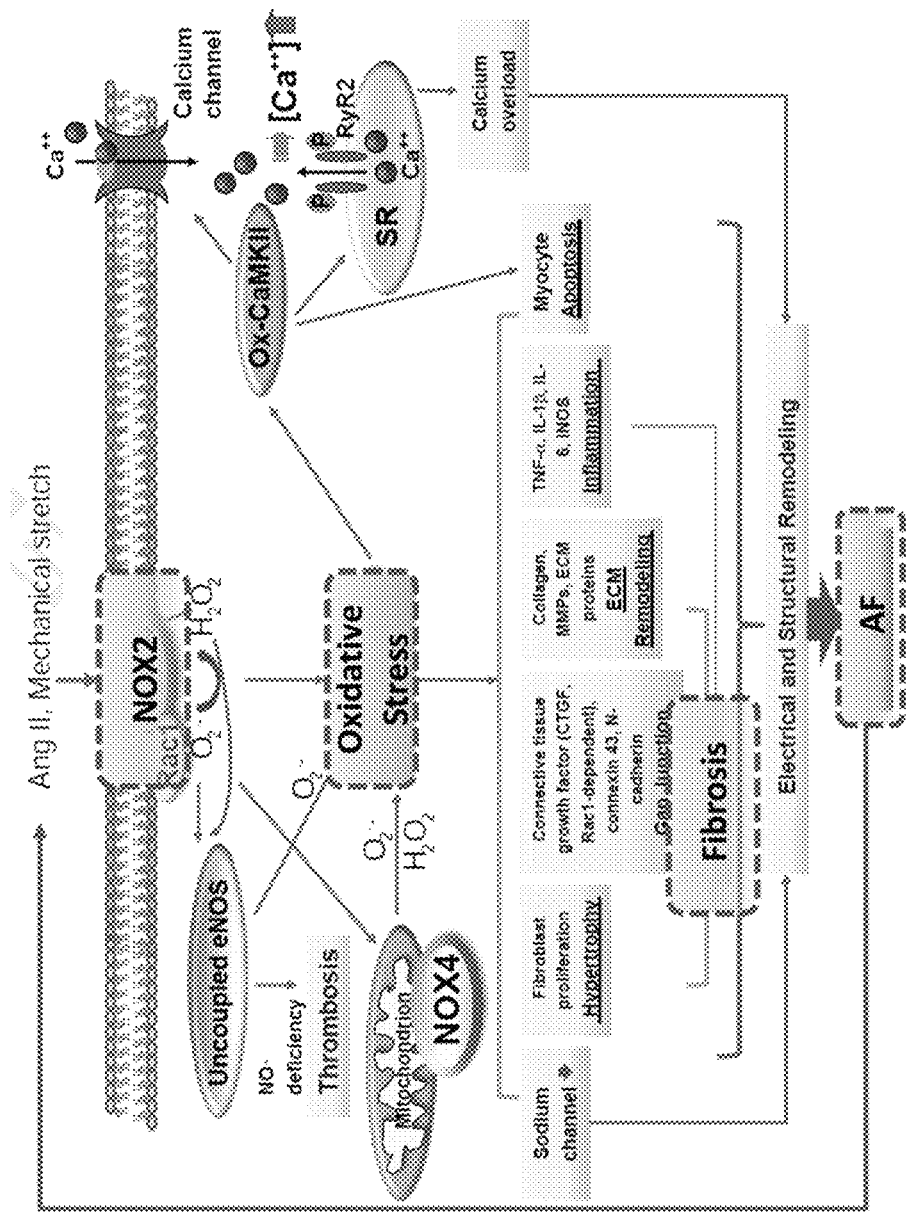
FIG. 1 depicts a scheme showing various mechanisms for reactive oxygen species production, oxidative stress generation, and development of fibrosis and atrial fibrillation.

The present disclosure provides details of the discovery of pharmaceutical compositions and methods for inhibiting oxidative stress in a subject suffering from atrial fibrillation. The method involves targeting reducing reactive oxygen species (ROS) generated through inhibiting the action of NADPH oxidase. The principle is demonstrated using an NOX2 inhibitor based upon RNA interference (RNAi) with small hairpin RNAs directed against the NOX2 mRNA (NOX2 shRNA). Pharmaceutical compositions based upon NOX2 shRNA is shown in the method to inhibit expression of the NOX2 gene, thereby leading to decreased production of NADPH oxidase in cardiac cells containing the injected NOX2 shRNAs. Referring to FIG. 1, lower NADPH oxidase production can lead to lower levels of ROS produced, lower extents of oxidative stress, decreased extents of atrial fibrosis and lower atrial fibrillation (AF). However, one skilled in the art will appreciate that the principle can be readily extended to other NOX2 inhibitors with undue experimentation and have a reasonable expectation of achieving similar results as described herein. Details of the pharmaceutical compositions and methods are presented in greater detail in this disclosure.

Terminology and Definitions

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

Terms used herein are intended as "open" terms (e.g., the term "including" should be interpreted as "including but not limited to," the term "having" should be interpreted as "having at least," the term "includes" should be interpreted as "includes but is not limited to," etc.).

The phrase "such as" should be interpreted as "for example, including."

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The phrase "small hairpin RNA" and the term "shRNA", as used herein, refer to a unimolecular RNA-containing polynucleotide that is capable of performing RNAi and that includes a sense sequence, a loop, and an antisense sequence. The sense and antisense sequences are sometimes referred to herein as the first region and second region. As described herein, the sense and antisense sequences can be in different orientations with respect to one another in an shRNA of the invention (an L or R shRNA). Thus, if the first region of an shRNA is the sense sequence then the second region is the antisense region, and vice versa. Preferably, the sense and antisense sequences are substantially complementary to each other (about 80% complementary). The antisense sequence can be about 16 to about 22 nucleotides in length, e.g., about 16 to 19 nucleotides, and more preferably 18 to 19 nucleotides in length. The sense sequence can be about 11 to about 22 nucleotides in length, and more preferably 17 to 19 nucleotides in length. An shRNA (and other RNAi agents) are "specific" for a target gene when the antisense sequence (of about 16 to 22 nucleotides is substantially complementary to the target gene (or target RNA, e.g., target mRNA). By substantially complementary is meant that the antisense sequence is at least 80% complementary to the target gene (or gene product). Thus, in some embodiments, the antisense sequence that is complementary to the target gene can contain mismatches to the target. The sequence can be varied to target one or more genetic variants or phenotypes of a target, e.g., a viral target, by altering the targeting sequence to be complementary to the sequence of the genetic variant or phenotype. An shRNA may have a loop as long as, for example, 0 to about 24 nucleotides in length, preferably 0 to about 10 nucleotides in length, 0 to 6 nucleotides in length, e.g., 2 nucleotides in length. The sequence of the loop can include nucleotide residues unrelated to the target. In one particularly preferred embodiment, the loop is 5'-UU-3'. In some embodiments it may include non-nucleotide moieties. In yet other embodiments, the loop does not include any non-nucleotides moieties. Optionally, the shRNA can have an overhang region of 2 bases on 3' end of the molecule. The shRNA can also comprise RNAs with stem-loop structures that contain mismatches and/or bulges. The sense sequence that is homologous to the target can differ at about 0 to about 5 sites by having mismatches, insertions, or deletions of from about 1 to about 5 nucleotides, as is the case, for example, with naturally occurring microRNAs. RNAs that comprise any of the above structures can include structures where the loops comprise nucleotides, non-nucleotides, or combinations of nucleotides and non-nucleotides.

Additionally, the phrase "small hairpin RNA" and the term "shRNA" include nucleic acids that also contain moieties other than ribonucleotide moieties, including, but not limited to, modified nucleotides, modified internucleotide linkages, non-nucleotides, deoxynucleotides and analogs of the nucleotides mentioned thereof.

Additionally, the term "L shRNA" refers to an shRNA comprising a sense sequence that is connected through a loop to the 3' end of the antisense.

Additionally, the term "R shRNA" refers to an shRNA molecule comprising an antisense sequence that is connected through a loop to the 3' end of the sense sequence.

The phrase "antisense sequence", as used herein, refers to a polynucleotide or region of a polynucleotide that is substantially complementary (e.g., 80% or more) or 100% complementary to a target nucleic acid of interest. An antisense sequence can be composed of a polynucleotide region that is RNA, DNA or chimeric RNA/DNA. Any nucleotide within an antisense sequence can be modified by including substituents coupled thereto, such as in a 2' modification. The antisense sequence can also be modified with a diverse group of small molecules and/or conjugates. For example, an antisense sequence may be complementary, in whole or in part, to a molecule of messenger RNA, an RNA sequence that is not mRNA (e.g., tRNA, rRNA, hnRNA, negative and positive stranded viral RNA and its complementary RNA) or a sequence of DNA that is either coding or non-coding.

The phrase "sense sequence", as used herein, refers to a polynucleotide or region that has the same nucleotide sequence, in whole or in part, as a target nucleic acid such as a messenger RNA or a sequence of DNA. When a sequence is provided, by convention, unless otherwise indicated, it is the sense sequence (or region), and the presence of the complementary antisense sequence (or region) is implicit.

The term "complementary", as used herein, refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

"Perfect complementarity" or "100% complementarity", as used herein, refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 19-mers, if 17 base pairs on each strand or each region can hydrogen bond with each other, the polynucleotide strands exhibit 89.5% complementarity. Substantial complementarity refers to polynucleotide strands or regions exhibiting about 80% or greater complementarity.

The term "deoxynucleotide", as used herein, refers to a nucleotide or polynucleotide lacking an OH group at the 2' or 3' position of a sugar moiety with appropriate bonding and/or 2',3' terminal dideoxy, instead having a hydrogen bonded to the 2' and/or 3' carbon.

The terms "deoxyribonucleotide" and "DNA", as used herein, refer to a nucleotide or polynucleotide comprising at least one ribosyl moiety that has an H at its 2' position of a ribosyl moiety instead of an OH.

In some embodiments, an shRNA described herein optionally includes at least one conjugate moiety.

The term "alkyl", as used herein, refers to a hydrocarbyl moiety that can be saturated or unsaturated, and substituted or unsubstituted. It may comprise moieties that are linear, branched, cyclic and/or heterocyclic, and contain functional groups such as ethers, ketones, aldehydes, carboxylates, etc. Unless otherwise specified, alkyl groups are not cyclic, heterocyclic, or comprise functional groups.

Exemplary alkyl groups include, but are not limited to, substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicoyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl and alkynyl groups. Unless otherwise specified, alkyl groups are not substituted.

Substitutions within an alkyl group, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The alkyl groups can by way of example also comprise modifications such as azo groups, keto groups, aldehyde groups, carboxyl groups, nitro, nitroso or nitrile groups, heterocycles such as imidazole, hydrazine or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Unless otherwise specified, alkyl groups do not contain hetero substitutions or alkyl rings with one or more heteroatoms (i.e., heterocyclic substitutions).

The preferred alkyl group for a 2' modification is a methyl group with an O-linkage to the 2' carbon of a ribosyl moiety, i.e., a 2' O-alkyl that comprises a 2'-O-methyl group.

The phrase "2'-O-alkyl modified nucleotide", as used herein, refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl.

As used herein, the term "2' carbon modification" refers to a nucleotide unit having a sugar moiety, for example a moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2'-O-isobutyl, 2'-O-ethyl-O-methyl(—OCH$_2$CH$_2$OCH$_3$), and 2'-O-ethyl-OH(—OCH$_2$CH$_2$OH). A "2' carbon sense sequence modification", as used herein, refers to a modification at the 2' carbon position of a nucleotide on the sense sequence. A "2' carbon antisense sequence modification", as used herein, refers to a modification at the 2' carbon position of a nucleotide on the antisense sequence.

The term "nucleotide", as used herein, refers to a ribonucleotide or a deoxyribonucleotide or modified from thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH.sub.2, NHR, NR.sub.2, or CN, wherein R is an alkyl moiety as defined herein. Nucleotide analogs also include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications include nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2'-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosien, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide analog also includes what are known in the art as universal bases. By way of example, universal bases include but are not limited to 3-nitropyrrole, 5-nitroindole, or nebularine.

Further, the term nucleotide analog also includes those species that have a detectable label, such as, for example, a radioactive or fluorescent moiety, or mass label attached to the nucleotide.

The term "overhang", as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' end of the duplex is referred to as an overhang.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The phrase "heating and snap cooling", as used herein, refers to a two-step procedure that involves heat-denaturing nucleic acids in a sample followed by rapid cooling. For example, tubes that contain shRNA solutions are denatured in a 95.degree. C. heat block for 4 to 5 minutes followed by immediately placing the tubes into an ice-water bath for 30 minutes. Such "heating and snap cooling" favors the formation of shRNA monomers over multimers.

As used herein, the term "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion or as described elsewhere throughout the specification.

The phrase "pharmaceutically acceptable carrier", as used herein, means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16.sup.th edition, Osol, A. Ed (1980) (incorporated herein by reference in its entirety).

As used herein, the term "operably-linked" refers to the association of nucleic acid sequences on a polynucleotide so that the function of one of the sequences is affected by another. For example, a regulatory DNA sequence is said to be "operably linked to" a DNA sequence that codes for an RNA ("an RNA coding sequence" or "shRNA encoding sequence") or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. An RNA coding sequence refers to a nucleic acid that can serve as a template for synthesis of an RNA molecule such as an shRNA. Preferably, the RNA coding region is a DNA sequence.

As used herein, the term "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that stimulates promoter activity and may be an innate element of the promoter or a heterologous element inserted to enhance the level or tissue specificity of a promoter. It is capable of operating in both orientations (sense or antisense), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Any promoter known in the art which regulates the expression of the shRNA or RNA coding sequence is envisioned in the practice of the invention.

As used herein, the term "reporter element" or "marker" is meant a polynucleotide that encodes a polypeptide capable of being detected in a screening assay. Examples of polypeptides encoded by reporter elements include, but are not limited to, lacZ, GFP, luciferase, and chloramphenicol acetyltransferase. See, for example, U.S. Pat. No. 7,416,849. Many reporter elements and marker genes are known in the art and envisioned for use in the inventions disclosed herein.

As used herein, the term "RNA transcript" refers to the product resulting from RNA polymerase catalyzed transcription of a DNA sequence. "Messenger RNA transcript (mRNA)" refers to the RNA that is without introns and that can be translated into protein by the cell.

As used herein, the term "shRNA" (small hairpin RNA) refers to an RNA duplex wherein a portion of the RNA is part of a hairpin structure (shRNA). In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some aspects, the overhang is a 3' or a 5' overhang 0, 1, 2, 3, 4 or 5 nucleotides in length. In one aspect of this invention, a nucleotide sequence in the vector serves as a template for the expression of a small hairpin RNA, comprising a sense region, a loop region and an antisense region. Following expression the sense and antisense regions form a duplex. It is this duplex, forming the shRNA, which hybridizes to, for example, the NOX2 mRNA and reduces expression of NADPH oxidase, lowering ROS and oxidative stress levels, fibrosis and AF.

As used herein, the term "knock-down" or "knock-down technology" refers to a technique of gene silencing in which the expression of a target gene or gene of interest is reduced as compared to the gene expression prior to the introduction of the siRNA, which can lead to the inhibition of production of the target gene product. "Double knockdown" is the knockdown of two genes. The term "reduced" is used herein to indicate that the target gene expression is lowered by 0.1-100%. For example, the expression may be reduced 0.5, 1, 5, 10, 15, 20, 25, 30, 35, 40, 45, 50, 55, 60, 65, 70, 75, 80, 85, 90, 95, or even 99%. The expression may be reduced by any amount (%) within those intervals, such as for example, 2-4, 11-14, 16-19, 21-24, 26-29, 31-34, 36-39, 41-44, 46-49, 51-54, 56-59, 61-64, 66-69, 71-74, 76-79, 81-84, 86-89, 91-94, 96, 97, 98 or 99. Knock-down of gene expression can be directed by the use of shRNAs.

As used herein, the term "treating" refers to ameliorating at least one symptom of, curing and/or preventing the development of a disease or disorder such as for example, but not limited to, cardiac fibrosis and AF.

As used herein, the term "vector" refers to any viral or non-viral vector, as well as any plasmid, cosmid, phage or binary vector in double or single stranded linear or circular form that may or may not be self transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Compositions for Inhibiting NOX2 Gene Expression in Posterior Left Atrium (PLA) Tissue In a one aspect, a pharmaceutical composition for treating oxidative stress in atrial fibrillation is provided. The pharmaceutical composition includes a small hairpin RNA (shRNA) directed against a NOX2 gene ("NOX2 shRNA"). The shRNA can be a unimolecular RNA that includes a sense sequence, a loop region, and an antisense sequence (sometimes referred to as first and second regions, as noted above), which together form a hairpin loop structure. Preferably, the antisense and sense sequences are substantially complementary to one other (about 80% complementary or more), where in certain embodiments the antisense and sense sequences are 100% complementary to each other. In certain embodiments, the antisense and sense sequences are too short to be processed by Dicer, and hence act through an alternative pathway to that of longer double-stranded RNAs (e.g., shRNAs having antisense and sense sequences of about 16 to about 22 nucleotides in length, e.g., between 18 and 19 nucleotides in length (e.g., an sshRNA). Additionally, the antisense and sense sequences within a unimolecular RNA of the invention can be the same length, or differ in length by less than about 9 bases. The loop can be any length, with the preferred length being from 0 to 4 nucleotides in length or an equivalent length of non-nucleotidic linker, and more preferably 2 nucleotides or an equivalent length of non-nucleotidic linker (e.g., a non-nucleotide loop having a length equivalent to 2 nucleotides). In one embodiment, the loop is: 5'-UU-3' (rUrU) or 5'-tt-3', where "t" represents deoxythymidine (dTdT). Within any shRNA hairpin, a plurality of the nucleotides are ribonucleotides. In the case of a loop of zero nucleotides, the antisense sequence is linked directly to the sense sequence, with part of one or both strands forming the loop. In a preferred embodiment of a zero-nt loop shRNA, the antisense sequence is about 18 or 19 nt and the sense sequence is shorter than the antisense sequence, so that one end of the antisense sequence forms the loop.

A hairpin of representative shRNA's can be organized in either a left-handed (L) hairpin (i.e., 5'-antisense-loop-sense-3') or a right-handed (R) hairpin (i.e., 5'-sense-loop-antisense-3'). Furthermore, an shRNA may also contain overhangs at either the 5' or 3' end of either the sense sequence or the antisense sequence, depending upon the organization of the hairpin. Preferably, if there are any overhangs, they are on the 3' end of the hairpin and comprise between 1 to 6 bases. The presence of an overhang is preferred for R-type hairpins, in which case a 2-nt overhang is preferred, and a UU or tt overhang is most preferred.

Modifications can be added to enhance shRNA stability, functionality, and/or specificity and to minimize immunostimulatory properties. For example, the overhangs can be unmodified, or can contain one or more specificity or stabilizing modifications, such as a halogen or O-alkyl modification of the 2' position, or internucleotide modifications such as phosphorothioate modification. The overhangs can be ribonucleic acid, deoxyribonucleic acid, or a combination of ribonucleic acid and deoxyribonucleic acid.

In another non-limiting example of modifications that can be applied to left handed hairpins, 2'-O-methyl modifications (or other 2' modifications, including but not limited to other 2'-O-alkyl modifications) can be added to nucleotides at position 15, 17, or 19 from the 5' antisense terminus of the hairpin, or any two of those positions, or all three, as well as to the loop nucleotides and to every other nucleotide of the sense sequence except for nucleotides 9, 10 and 11 from the 5'-most nucleotide of the sense sequence (also called the 9.sup.th, 10.sup.th, and 11.sup.th nucleotides), which should have no modifications that block "slicing" activity. Any single modification or group of modifications described in the preceding sentence can be used alone or in combination with any other modification or group of modifications cited.

Ui-Tei, K. et al. (*Nucl. Acids Res.* (2008) 36 (22): 7100-7109) observed that the specificity of siRNAs can be increased by modifying the seed region of one or both strands. Such modifications are applicable to shRNA's of the present disclosure. In another non-limiting example of modifications that can be applied to hairpins, nt 1-6 of the antisense sequence and nt 14-19 of the sense sequence can be 2'-O-methylated to reduce off-target effects. In a preferred embodiment, only nt 1-6 are modified from 2'-OH to 2'-H or 2'-O-alky.

As the sense sequence of an shRNA can potentially enter RISC and compete with the antisense (targeting) strand, modifications that prevent sense sequence phosphorylation are valuable in minimizing off-target signatures. Thus, desirable chemical modifications that prevent phosphorylation of the 5' carbon of the 5'-most nucleotide of right-handed shRNA of the invention can include, but are not limited to, modifications that: (1) add a blocking group (e.g., a 5'-O-alkyl) to the 5' carbon; or (2) remove the 5'-hydroxyl group (e.g., 5'-deoxy nucleotides) (see, e.g., WO 2005/078094).

In addition to modifications that enhance specificity, modifications that enhance stability can also be added. In one embodiment, modifications comprising 2'-O-alkyl groups (or other 2' modifications) can be added to one or more, and preferably all, pyrimidines (e.g., C and/or U nucleotides) of the sense sequence. Modifications such as 2' F or 2'-O-alkyl of some or all of the Cs and Us of the sense sequence/region, respectively, or the loop structure, can enhance the stability of the shRNA molecules without appreciably altering target specific silencing. It should be noted that while these modifications enhance stability, it may be desirable to avoid the addition of these modification patterns to key positions in the hairpin in order to avoid disruption of RNAi (e.g., that interfere with "slicing" activity).

Additional stabilization modifications to the phosphate backbone may be included in the shRNAs in some embodiments of the present invention. For example, at least one phosphorothioate, phosphordithioate, and/or methylphosphonate may be substituted for the phosphate group at some or all 3' positions of nucleotides in the shRNA backbone, or any particular subset of nucleotides (e.g., any or all pyrimidines in the sense sequence of the oligonucleotide backbone), as well as in any overhangs, and/or loop structures present. These modifications may be used independently or in combination with the other modifications disclosed herein.

Description of modified shRNAs of interest can be found in the following references, both of which are incorporated herein by reference in their entirety: Q. Ge, H. Ilves, A. Dallas, P. Kumar, J. Shorenstein, S. A. Kazakov, and B. H. Johnston (2010) Minimal-length short hairpin RNAs: The Relationship of Structure and RNAi Activity. RNA 16(1): 106-17 (Epub Dec. 1, 2009); and Q. Ge, A. Dallas, H. Ilves, J. Shorenstein, M. A. Behlke, and B. H. Johnston (2010) Effects of Chemical Modification on the Potency, Serum Stability, and Immunostimulatory Properties of Short shRNAs. RNA 16(1):118-30 (Epub Nov. 30, 2009).

Modified shRNAs according to aspects of the present invention may include additional chemical modifications for any of a variety of purposes, including 3' cap structures (e.g., an inverted deoxythymidine), detectable labels conjugated to one or more positions in the shRNA (e.g., fluorescent labels, mass labels, radioactive labels, etc.), or other conjugates that can enhance delivery, detection, function, specificity, or stability (e.g., amino acids, peptides, proteins, sugars, carbohydrates, lipids, polymers, nucleotides, polynucleotides, etc.). Combinations of additional chemical modifications may be employed as desired by the user.

Suitable NOX2 shRNAs include those nucleic acids ranging from about 20 nucleotides to about 80 nucleotides in length, wherein a portion of the nucleic acids have a double-stranded structural domain ranging from about 15 nucleotides to about 25 nucleotides in length. In some aspects, the shRNA can include modified bases or phosphodiester backbones to impart stability of the shRNA inside tissues and cells. An exemplary NOX2 shRNA includes SEQ ID NO:1 presented in Table 1.

TABLE 1

| Exemplary NOX2 shRNA (SEQ ID NO: 1) 5' → 3' Nucleotide Sequence |
| --- |
| TATCCATTTCCAAGTCATAGG | shRNA: Synthesis

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally occurring oligonucleotides, as described herein.

shRNA molecules of the invention can be prepared by any method known in the art for the synthesis of DNA and RNA molecules. These include techniques for chemically synthesizing oligodeoxy-ribonucleotides and oligo-ribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

shRNA molecules can be chemically synthesized using appropriately protected ribonucleoside phosphoramidites and a conventional DNA/RNA synthesizer. Custom shRNA synthesis services are available from commercial vendors such as Ambion (Austin, Tex., USA) and Dharmacon Research (Lafayette, Colo., USA). See, for example, U.S. Pat. No. 7,410,944.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone. An antisense nucleic acid of the invention can be constructed using chemical synthesis or enzymatic ligation reactions using procedures known in the art. An antisense oligonucleotide can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

The shRNA molecules of the invention can be various modified equivalents of the structures of any NOX2 shRNA. A "modified equivalent" means a modified form of a particular shRNA molecule having the same target-specificity (i.e., recognizing the same mRNA molecules that complement the unmodified particular shRNA molecule). Thus, a modified equivalent of an unmodified shRNA molecule can have modified ribonucleotides, that is, ribonucleotides that contain a modification in the chemical structure of an unmodified nucleotide base, sugar and/or phosphate (or phosphodiester linkage). See, for example, U.S. Pat. No. 7,410,944.

Preferably, modified shRNA molecules contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like. See, for example, U.S. Pat. No. 7,410,944.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See, for example, U.S. Pat. No. 7,410,944.

Examples of the non-phosphorous containing backbones described above are known in the art, e.g., U.S. Pat. No. 5,677,439, each of which is herein incorporated by reference. See, for example, U.S. Pat. No. 7,410,944.

Modified forms of shRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxy methyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyl uridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyl adenosine, beta-D-mannosylqueosine, uridine-5-oxyacetic acid, 2-thiocytidine, threonine derivatives, and the like. See, for example, U.S. Pat. No. 7,410,944.

In addition, modified shRNA compounds can also have substituted or modified sugar moieties, e.g., 2'-O-methoxyethyl sugar moieties. See, for example, U.S. Pat. No. 7,410,944.

Preferably, the 3' overhangs of the shRNAs of the present invention are modified to provide resistance to cellular nucleases. In one embodiment the 3' overhangs comprise 2'-deoxyribonucleotides.

Additional shRNA compounds targeted at different sites of the mRNA corresponding to NOX2. Additionally, to assist in the design of shRNAs for the efficient RNA interference (RNAi)-mediated silencing of any target gene, several shRNA supply companies maintain web-based design tools that utilize these general guidelines for "picking" shRNAs when presented with the mRNA or coding DNA sequence of the target gene. Examples of such tools can be found at the web sites of Dharmacon, Inc. (Lafayette, Colo.), Ambion, Inc. (Austin, Tex.). As an example, picking shRNAs involves choosing a site/sequence unique to the target gene (i.e., sequences that share no significant homology with genes other than the one being targeted), so that other genes are not inadvertently targeted by the same shRNA designed for this particular target sequence.

Another criterion to be considered is whether or not the target sequence includes a known polymorphic site. If so, shRNAs designed to target one particular allele may not effectively target another allele, since single base mismatches between the target sequence and its complementary strand in a given shRNA can greatly reduce the effectiveness of RNAi-induced by that shRNA. Given that target sequence and such design tools and design criteria, an ordinarily skilled artisan apprised of the present disclosure should be able to design and synthesized additional sihRNA compounds useful in reducing the mRNA level of NOX2.

shRNA: Administration

The present invention provides a composition of a polymer or excipient and one or more vectors encoding one or more shRNA molecules. The vector can be formulated into a pharmaceutical composition with suitable carriers and administered into a mammal using any suitable route of administration.

Because of this precision, side effects typically associated with traditional drugs can be reduced or eliminated. In addition, shRNA are relatively stable, and like antisense, they can also be modified to achieve improved pharmaceutical characteristics, such as increased stability, deliverability, and ease of manufacture. Moreover, because shRNA molecules take advantage of a natural cellular pathway, i.e., RNA interference, they are highly efficient in destroying targeted mRNA molecules. As a result, it is relatively easy to achieve a therapeutically effective concentration of an shRNA compound in a subject. See, for example, U.S. Pat. No. 7,410,944.

shRNA compounds may be administered to mammals by various methods through different mutes. They can also be delivered directly to a particular organ or tissue by any suitable localized administration methods such as direct injection into a target tissue. Preferably, shRNA compounds can be electroporated into cells following their injection directly into the target tissue. Alternatively, they may be delivered encapsulated in liposomes, by iontophoresis, or by incorporation into other vehicles such as hydrogels, cyclodextrins, biodegradable nanocapsules, and bioadhesive microspheres.

In vivo inhibition of specific gene expression by RNAi injected intravenously has been achieved in various organisms including mammals. See, for example, Song E. et al. "RNA interference targeting Fas protects mice from fulminant hepatitis," Nature Medicine, 9:347-351 (2003). One mute of administration of shRNA molecules of the invention includes direct injection of the vector at a desired tissue site, such as for example, into diseased or non-diseased cardiac tissue, into fibrotic heart tissue, such as fibrotic PLA tissue. Generally, however, NOX2 shRNAs or expression vectors encoding NOX2 shRNAs can be directly injected into any atrial tissue to effectively knock-down NOX2 protein expression, to inhibit NADPH oxidase enzyme activity, to effectively reduce ROS levels and oxidative stress in atrial tissues at the sites of injection, to reduce or altogether eliminate the presence of AF in a subject, or to reduce progression of fibrosis leading to increased AF presentation in a subject.

NAPDH oxidase (NOX2) is significantly elevated in the ventricle of heart failure patients, and is thought be a contributor to the heart failure state. Accordingly, NOX2 shRNAs or expression vectors encoding NOX2 shRNAs can be directly injected into ventricle tissue to effectively knock-down NOX2 protein expression, to inhibit NADPH oxidase enzyme activity, to effectively reduce ROS levels and oxidative stress in ventricle tissues at the sites of injection, to reduce or altogether eliminate progression of ventricle damage leading to increased HF presentation in a subject.

In one aspect of the invention, one or more vectors comprising one or more of shRNA of the invention can be readministered an unlimited number of times after a first administration at any time interval or intervals after the first administration.

shRNA: Pharmaceutical Compositions

The shRNA encoding nucleic acids of the present invention can be formulated in pharmaceutical compositions, which are prepared according to conventional pharmaceutical compounding techniques. See, e.g., Remington's Pharmaceutical Sciences, 18th Ed. (1990, Mack Publishing Co., Easton, Pa.). The pharmaceutical compositions of the invention comprise a therapeutically effective amount of the vector encoding shRNA. These compositions can comprise, in addition to the vector, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intramuscular, subcutaneous, intrathecal, epineural or parenteral.

When the vectors of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation In another aspect of the invention, the vectors of the invention can be suitably formulated and introduced into the environment of the cell by any means that allows for a sufficient portion of the sample to enter the cell to induce gene silencing, if it is to occur. Many formulations for vectors are known in the art and can be used so long as the vectors gain entry to the target cells so that it can act.

For example, the vectors can be formulated in buffer solutions such as phosphate buffered saline solutions comprising liposomes, micellar structures, and capsids. The pharmaceutical formulations of the vectors of the invention can also take the form of an aqueous or anhydrous solution or dispersion, or alternatively the form of an emulsion or suspension. The pharmaceutical formulations of the vectors of the present invention may include, as optional ingredients, solubilizing or emulsifying agents, and salts of the type that are well-known in the art. Specific non-limiting examples of the carriers and/or diluents that are useful in the pharmaceutical formulations of the present invention include water and physiologically acceptable saline solutions. Other pharmaceutically acceptable carriers for preparing a composition for administration to an individual include, for example, solvents or vehicles such as glycols, glycerol, or injectable organic esters. A pharmaceutically acceptable carrier can contain physiologically acceptable compounds that act, for example, to stabilize or to increase the absorption of the shRNA encoding vector. Other physiologically acceptable carriers include, for example, carbohydrates, such as glucose, sucrose or dextrans, antioxidants, such as ascorbic acid or glutathione, chelating agents, low molecular weight proteins or other stabilizers or excipients, saline, dextrose solutions, fructose solutions, ethanol, or oils of animal, vegetative or synthetic origin. The carrier can also contain other ingredients, for example, preservatives.

It will be recognized that the choice of a pharmaceutically acceptable carrier, including a physiologically acceptable compound, depends, for example, on the mute of administration of the composition. The composition containing the vectors can also contain a second reagent such as a diagnostic reagent, nutritional substance, toxin, or additional therapeutic agent. Many agents useful in the treatment of cardiac disease are known in the art and are envisioned for use in conjunction with the vectors of this invention.

Formulations of vectors with cationic lipids can be used to facilitate transfection of the vectors into cells. For example, cationic lipids, such as lipofectin, cationic glycerol derivatives, and polycationic molecules, such as polylysine, can be used. Suitable lipids include, for example, Oligofectamine and Lipofectamine (Life Technologies), which can be used according to the manufacturer's instructions.

Suitable amounts of vector must be introduced and these amounts can be empirically determined using standard methods. Typically, effective concentrations of individual vector species in the environment of a cell will be about 50 nanomolar or less 10 nanomolar or less, or compositions in which concentrations of about 1 nanomolar or less can be used. In other aspects, the methods utilize a concentration of about 200 picomolar or less and even a concentration of about 50 picomolar or less can be used in many circumstances. One of skill in the art can determine the effective concentration for any particular mammalian subject using standard methods.

The shRNA is preferably administered in a therapeutically effective amount. The actual amount administered, and the rate and time-course of administration, will depend on the nature and severity of the condition, disease or disorder being treated. Prescription of treatment, for example, decisions on dosage, timing, etc., is within the responsibility of general practitioners or specialists, and typically takes account of the disorder, condition or disease to be treated, the condition of the individual mammalian subject, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the shRNA encoding vectors more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

shRNA: Gene Therapy shRNA can also be delivered into mammalian cells, particularly human cells, by a gene therapy approach, using a DNA vector from which shRNA compounds in, e.g., small hairpin form (shRNA), can be transcribed directly. Recent studies have demonstrated that while double-stranded shRNAs are very effective at mediating RNAi, short, single-stranded, hairpin-shaped RNAs can also mediate RNAi, presumably because they fold into intramolecular duplexes that are processed into double-stranded shRNAs by cellular enzymes. This discovery has significant and far-reaching implications, since the production of such shRNAs can be readily achieved in vivo by transfecting cells or tissues with DNA vectors bearing short inverted repeats separated by a small number of (e.g., 3, 4, 5, 6, 7, 8, 9) nucleotides that direct the transcription of such small hairpin RNAs. Additionally, if mechanisms are included to direct the integration of the vector or a vector segment into the host-cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice.

Gene therapy is carried out according to generally accepted methods as are known in the art. See, for example, U.S. Pat. Nos. 5,837,492 and 5,800,998 and references cited therein. Vectors in the context of gene therapy are meant to include those polynucleotide sequences containing sequences sufficient to express a polynucleotide encoded therein. If the polynucleotide encodes an shRNA, expression will produce the antisense polynucleotide sequence. Thus, in this context, expression does not require that a protein product be synthesized. In addition to the shRNA encoded in the vector, the vector also contains a promoter functional in eukaryotic cells. The shRNA sequence is under control of this promoter. Suitable eukaryotic promoters include those described elsewhere herein and as are known in the art. The expression vector may also include sequences, such as selectable markers, reporter genes and other regulatory sequences conventionally used.

Figure 4:
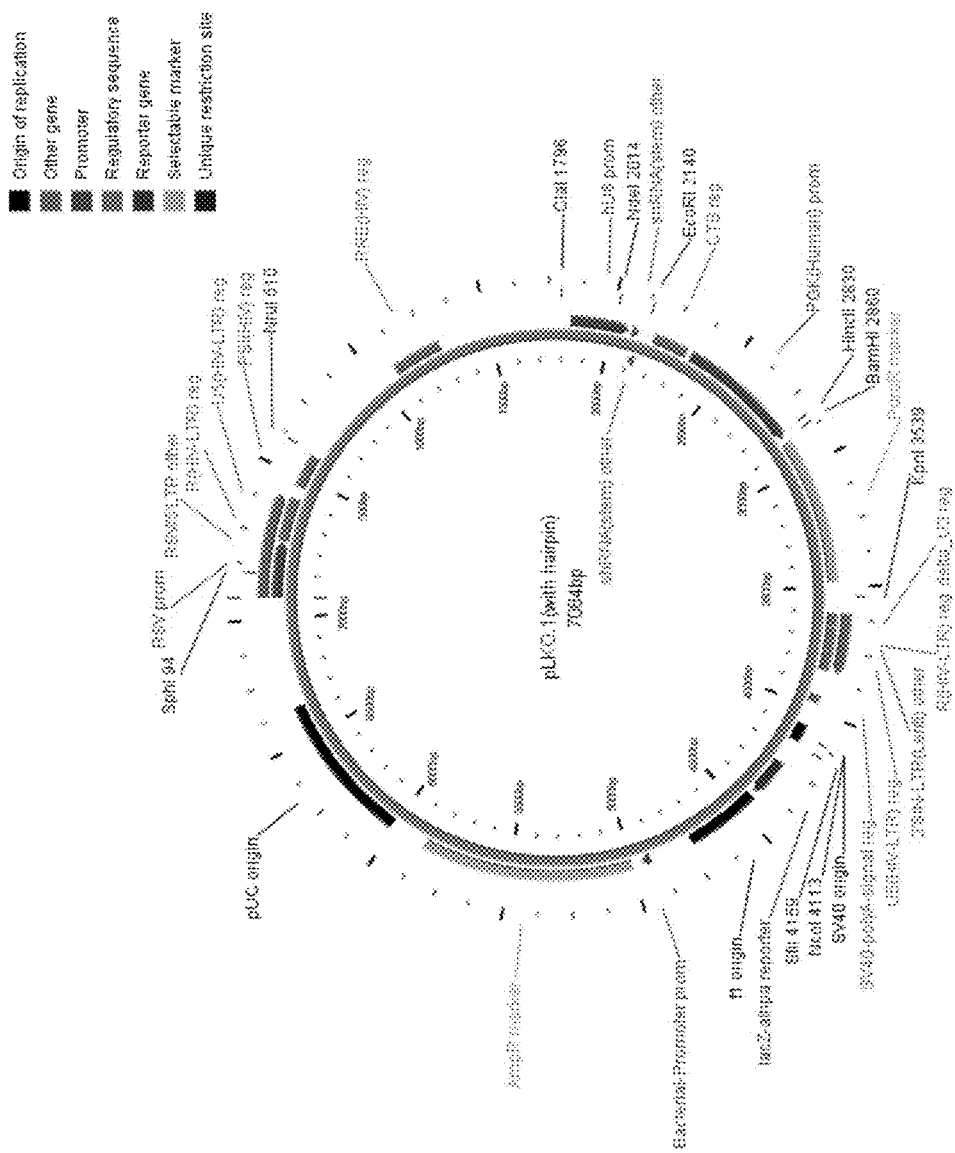
FIG. 4 shows an exemplary expression vector for expression a NOX2 shRNA under the control of a U6 PolIII promoter.

Accordingly, the amount of shRNA generated in situ is regulated by controlling such factors as the nature of the promoter used to direct transcription of the nucleic acid sequence, (i.e., whether the promoter is constitutive or regulatable, strong or weak) and the number of copies of the nucleic acid sequence encoding a shRNA sequence that are in the cell. Exemplary promoters include those recognized by pol I, pol II and pol III. In some aspects, a preferred promoter is a pol III promoter, such as the U6 pol III promoter. An exemplary vector for encoding an NOX2 shRNA is depicted in FIG. 4 and illustrated in Table 2.

TABLE 2

Expression vector encoding a NOX2 shRNA.
5' → 3' (nucleotide sequence) [SEQ ID NO: 2]

aatgtagtcttatgcaatactcttgtagtcttgcaacatggtaacgatgagttagcaacatgccttacaaggagagaaaa agcaccgtgcatgccgattggtggaagtaaggtggtacgatcgtgccttattaggaaggcaacagacgggtctgacatgg attggacgaaccactgaattgccgcattgcagagatattgtatttaagtgcctagctcgatacataaacgggtctctctg gttagaccagatctgagcctgggagctctctggctaactagggaacccactgcttaagcctcaataaagcttgccttgag tgcttcaagtagtgtgtgcccgtctgttgtgtgactctggtaactagagatccctcagaccctttagtcagtgtggaaa atctctagcagtggcgcccgaacagggacttgaaagcgaaagggaaaccagaggagctctctcgacgcaggactcggctt gctgaagcgcgcacggcaagaggcgaggggcggcgactggtgagtacgccaaaaattttgactagcggaggctagaagga gagagatgggtgcgagagcgtcagtattaagcgggggagaattagatcgcgatgggaaaaaattcggttaaggccagggg gaaagaaaaatataaattaaaacatatagtatgggcaagcagggagctagaacgattcgcagttaatcctggcctgtta gaaacatcagaaggctgtagacaaatactgggacagctacaaccatcccttcagacaggatcagaagaacttagatcatt atataatacagtagcaaccctctattgtgtgcatcaaaggatagagataaaagacaccaaggaagctttagacaagatag aggaagagcaaaacaaaagtaagaccaccgcacagcaagcggccgctgatcttcagacctggaggaggagatatgaggga caattggagaagtgaattatataaatataaagtagtaaaaattgaaccattaggagtagcacccaccaaggcaaagagaa gagtggtgcagagagaaaaaagagcagtgggaataggagctttgttccttgggttcttgggagcagcaggaagcactatg ggcgcagcgtcaatgacgctgacggtacaggccagacaattattgtctggtatagtgcagcagcagaacaatttgctgag ggctattgaggcgcaacagcatctgttgcaactcacagtctggggcatcaagcagctccaggcaagaatcctggctgtgg aaagatacctaaaggatcaacagctcctggggatttggggttgctctggaaaactcatttgcaccactgctgtgccttgg aatgctagttggagtaataaatctctggaacagatttggaatcacacgacctggatggagtgggacagagaaattaacaa TABLE 2-continued Expression vector encoding a NOX2 shRNA.
5' → 3' (nucleotide sequence) [SEQ ID NO: 2]

ttacacaagcttaatacactccttaattgaagaatcgcaaaaccagcaagaaaagaatgaacaagaattattggaattag ataaatgggcaagtttgtggaattggtttaacataacaaattggctgtggtatataaaattattcataatgatagtagga ggcttggtaggtttaagaatagtttttgctgtactttctatagtgaatagagttaggcagggatattcaccattatcgtt tgagacccacctcccaaccccgaggggacccgacaggcccgaaggaataagaagaaggtggagagagagacagagaca gatccattcgattagtgaacggatctcgacggtatcgatcacgagactagcctcgagcggccgcccccttcaccgagggc ctatttcccatgattccttcatatttgcatatacgatacaaggctgttagagagataattggaattaatttgactgtaaa cacaaagatattagtacaaaatacgtgacgtagaaagtaataatttcttgggtagtttgcagttttaaaattatgtttta aaatggactatcatatgcttaccgtaacttgaaagtatttcgatttcttggctttatatatcttgtggaaaggacgaaac accggtacaacagccacaacgtctatctcgagatagacgttgtggctgttgtattttttgaattctcgacctcgagacaaa tggcagtattcatccacaattttaaaagaaaaggggggattgggggtacagtgcagggggaaagaatagtagacataata gcaacagacatacaaactaaagaattacaaaaacaaattacaaaaattcaaaattttcgggtttattacagggacagcag agatccactttggccgcggctcgagggggttgggggttgcgccttttccaaggcagccctgggtttgcgcagggacgcggc tgctctgggcgtggttccgggaaacgcagcggcgccgaccctgggtctcgcacattcttcacgtccgttcgcagcgtcac ccggatcttcgccgctaccttgtgggccccccggcgacgcttcctgctccgcccctaagtcgggaaggttccttgcggt tcgcggcgtgccggacgtgacaaacggaagccgcacgtctcactagtaccctcgcagacggacagcgccagggagcaatg gcagcgcgccgaccgcgatgggctgtggccaatagcggctgctcagcagggcgcgccgagagcagcggccgggaaggggc ggtgcgggaggcggggtgtggggcggtagtgtgggccctgttcctgcccgcgcggtgttccgcattctgcaagcctccgg agcgcacgtcggcagtcggctccctcgttgaccgaatcaccgacctctctcccaggggatccaccggagcttaccatg accgagtacaagcccacggtgcgcctcgccacccgcgacgacgtcccagggccgtacgcaccctcgccgccgcgttcgc cgactaccccgccacgcgccacaccgtcgatccggaccgccacatcgagcgggtcaccgagctgcaagaactcttcctca cgcgcgtcgggctcgacatcggcaaggtgtgggtcgcggacgacggcgccggtggcggtctggaccacgccggagagc gtcgaagcgggggcggtgttcgccgagatcggcccgcgcatggccgagttgagcggttcccggctggccgagcagcaaca gatggaaggcctcctggcgccgcaccggcccaaggagcccgcgtggttcctggccaccgtcggcgtctcgcccgaccacc agggcaagggtctgggcagcgccgtcgtgctccccggagtggaggcggccgagcgcgccggggtgcccgccttcctggag acctccgcgccccgcaacctcccccttctacgagcggctcggcttcaccgtcaccgccgacgtcgaggtgcccgaaggacc gcgcacctggtgcatgacccgcaagcccggtgcctgacgcccgccccacgacccgcagcgcccgaccgaaaggagcgcac gaccccatgcatcggtaccttaagaccaatgacttacaaggcagctgtagatcttagccactttttaaaagaaaagggg ggactggaagggctaattcactcccaacgaagacaagatctgcttttttgcttgtactgggtctctctggttagaccagat ctgagcctgggagctctctggctaactagggaacccactgcttaagcctcaataaagcttgccttgagtgcttcaagtag tgtgtgcccgtctgttgtgtgactctggtaactagagatccctcagaccctttagtcagtgtggaaaatctctagcagt agtagttcatgtcatcttattattcagtatttataacttgcaaagaaatgaatatcagagagtgagaggaacttgtttat tgcagcttataatggttacaaataaagcaatagcatcacaaatttcacaaataaagcattttttcactgcattctagtt gtggtttgtccaaactcatcaatgtatcttatcatgtctggctctagctatcccgcccctaactccgcccatcccgcccc taactccgcccagttccgcccattctccgcccatggctgactaattttttttatttatgcagaggccgaggccgcctcg gcctctgagctattccagaagtagtgaggaggctttttggaggcctagggacgtacccaattcgccctatagtgagtcg tattacgcgcgctcactggccgtcgttttacaacgtcgtgactgggaaaaccctggcgttacccaacttaatcgccttgc agcacatccccctttcgccagctggcgtaatagcgaagaggcccgcaccgatcgcccttcccaacagttgcgcagcctga atggcgaatgggacgcgccctgtagcggcgcattaagcgcggcgggtgtggtggttacgcgcagcgtgaccgctacactt TABLE 2-continued Expression vector encoding a NOX2 shRNA.
5' → 3' (nucleotide sequence) [SEQ ID NO: 2]

```
gccagcgccctagcgccgctcctttcgctttcttcccttcctttctcgccacgttcgccggctttccccgtcaagctct
aaatcggggctccctttagggttccgatttagtgctttacggcacctcgaccccaaaaaacttgattagggtgatggtt
cacgtagtgggccatcgccctgatagacggttttcgcccttttgacgttggagtccacgttctttaatagtggactcttg
ttccaaactggaacaacactcaaccctatctcggtctattcttttgattttataagggattttgccgatttcggcctattg
gttaaaaaatgagctgatttaacaaaaatttaacgcgaattttaacaaaatattaacgcttacaatttaggtggcacttt
tcggggaaatgtgcgcggaaccccctatttgtttattttttctaaatacattcaaatatgtatccgctcatgagacaataac
cctgataaatgcttcaataatattgaaaaaggaagagtatgagtattcaacatttccgtgtcgcccttattccctttttt
gcggcattttgccttcctgttttgctcacccagaaacgctggtgaaagtaaaagatgctgaagatcagttgggtgcacg
agtgggttacatcgaactggatctcaacagcggtaagatccttgagagttttcgccccgaagaacgttttccaatgatga
gcacttttaaagttctgctatgtggcgcggtattatcccgtattgacgccgggcaagagcaactcggtcgccgcatacac
tattctcagaatgacttggttgagtactcaccagtcacagaaaagcatcttacggatggcatgacagtaagagaattatg
cagtgctgccataaccatgagtgataacactgcggccaacttacttctgacaacgatcggaggaccgaaggagctaaccg
cttttttgcacaacatgggggatcatgtaactcgccttgatcgttgggaaccggagctgaatgaagccataccaaacgac
gagcgtgacaccacgatgcctgtagcaatggcaacaacggtgcgcaaactattaactggcgaactacttactctagcttc
ccggcaacaattaatagactggatggaggcggataaagttgcaggaccacttctgcgctcggcccttccggctggctggt
ttattgctgataaatctggagccggtgagcgtgggtctcgcggtatcattgcagcactggggccagatggtaagccctcc
cgtatcgtagttatctacacgacggggagtcaggcaactatggatgaacgaaatagacagatcgctgagataggtgcctc
actgattaagcattggtaactgtcagaccaagtttactcatatactttagattgatttaaaacttcatttttaattta
aaaggatctaggtgaagatcctttttgataatctcatgaccaaaatcccttaacgtgagttttcgttccactgagcgtca
gaccccgtagaaaagatcaaaggatcttcttgagatcctttttttctgcgcgtaatctgctgcttgcaaacaaaaaaacc
accgctaccagcggtggtttgtttgccggatcaagagctaccaactcttttccgaaggtaactggcttcagcagagcgc
agataccaaatactgttcttctagtgtagccgtagttaggccaccacttcaagaactctgtagcaccgcctacatacctc
gctctgctaatcctgttaccagtggctgctgcagttggcgataagtcgtgtcttaccgggttggactcaagacgatagtt
accggataaggcgcagcggtcgggctgaacggggggttcgtgcacacagcccagcttggagcgaacgacctacaccgaac
tgagatacctacagcgtgagctatgagaaagcgccacgcttcccgaagggagaaaggcggacaggtatcaggtaagcggc
agggtcggaacaggagagcgcacgagggagcttccaggggggaaacgcctggtatctttatagtcctgtcgggtttcgcca
cctctgacttgagcgtcgatttttgtgatgctcgtcaggggggcggagcctatggaaaaacgccagcaacgcggccttt
tacggttcctggccttttgctggccttttgctcacatgttctttcctgcgttatcccctgattctgtggataaccgtatt
accgcctttgagtgagctgataccgctcgccgcagccgaacgaccgagcgcagcgagtcagtgagcgaggaagcggaaga
gcgcccaatacgcaaaccgcctctccccgcgcgttggccgattcattaatgcagctggcacgacaggtttcccgactgga
aagcgggcagtgagcgcaacgcaattaatgtgagttagctcactcattaggcacccaggctttacactttatgcttccg
gctcgtatgttgtgtggaattgtgagcggataacaatttcacacaggaaacagctatgaccatgattacgccaagcgcgc
aattaaccctcactaaagggaacaaaagctggagctgcaagctt
```

Kits

The subject invention also includes kits for inhibiting expression of a target gene in a cell, the kit including a chemically modified shRNA as described herein. A "kit" refers to any system for delivering materials or reagents for carrying out a method of the invention. In the context of reaction assays, such delivery systems include systems that allow for the storage, transport, or delivery of reaction reagents (e.g., chemically modified shRNA, culture medium, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. Such contents may be delivered to the intended recipient together or separately. For example, a first container may contain a chemically modified shRNA for use in an assay, while a second container contains culture media RNA delivery agents (e.g., transfection reagents).

As noted above, the subject kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control reagents, e.g., non-chemically modified shRNA.

Methods

Figure 2A:
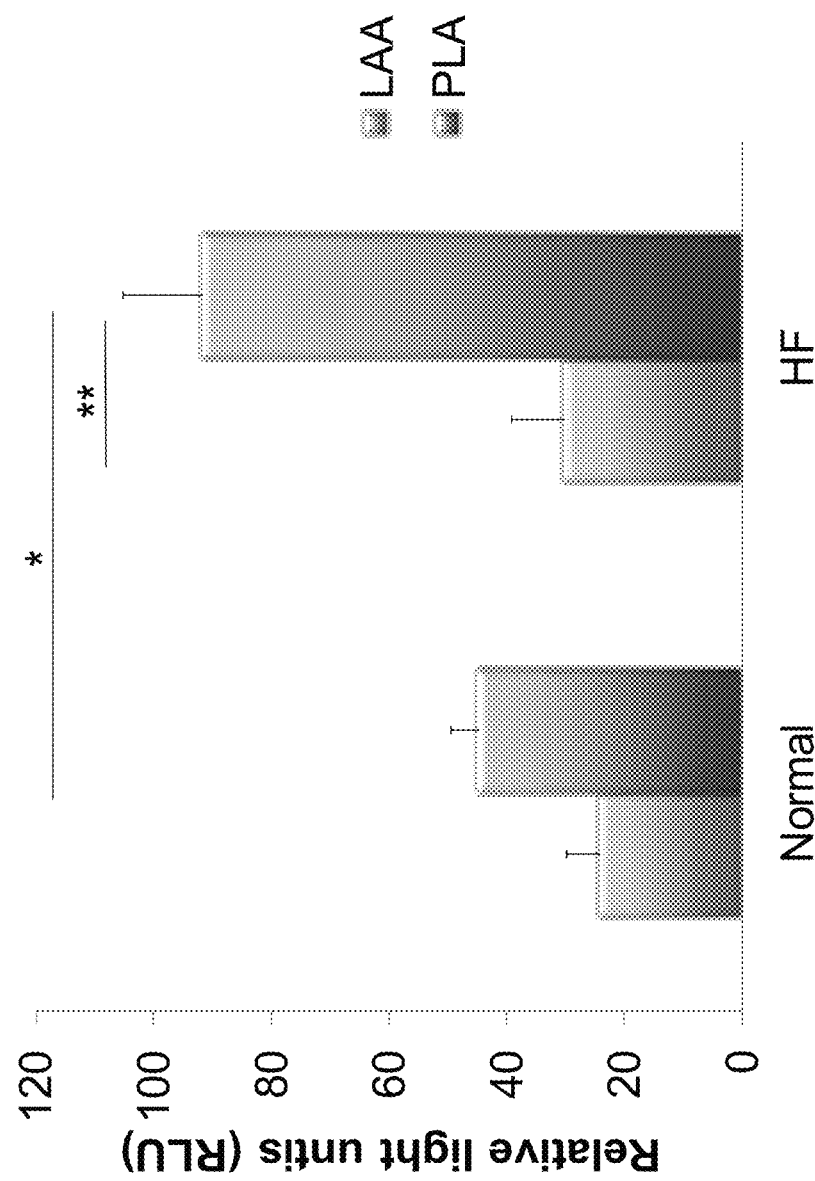
FIG. 2A depicts $O_2^-$ production, as measured by lucigenin enhanced chemiluminescence assay, for left atrial appendage (LAA; light blue bars) and posterior left atrium (PLA; dark blue bars) for normal and HF animals. Statistics key: *, p<0.05; **, p<0.001.
Figure 2B:
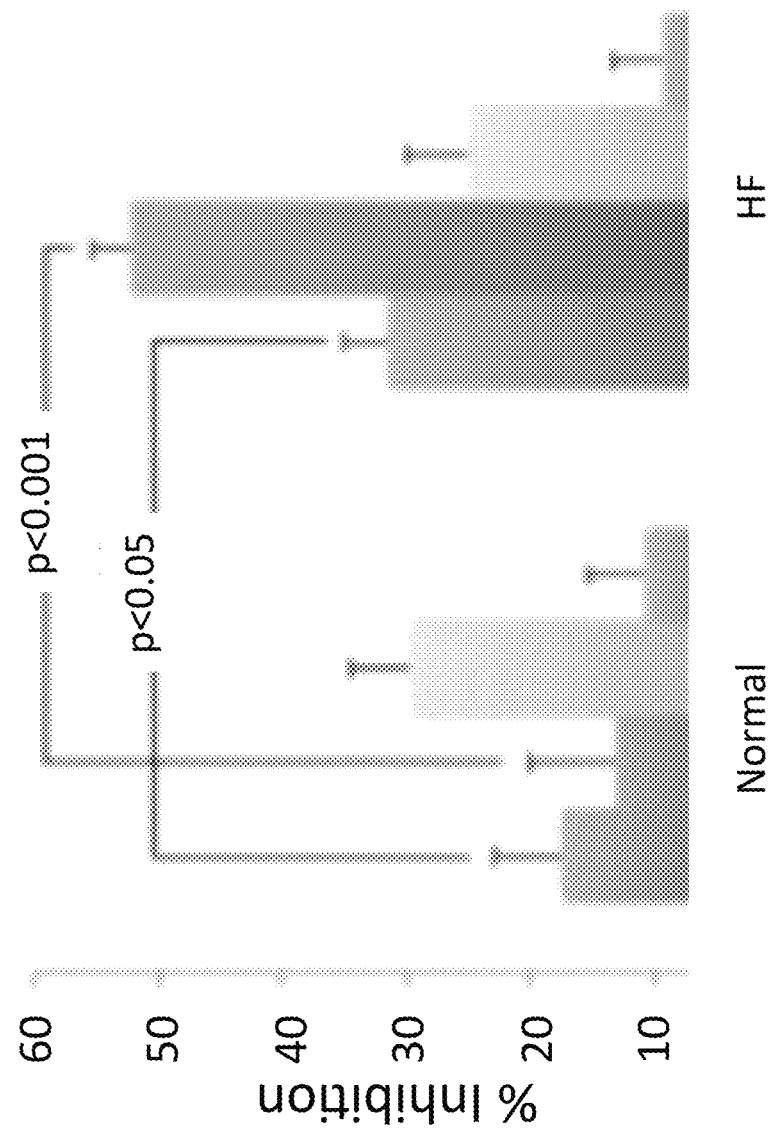
FIG. 2B depicts $O_2^-$ production (as measured by lucigenin enhanced chemiluminescence assay) in PLA for NADPH oxidase (blue bars), Mitochondrial ROS (red bars), NOS (green bars) and Xanthine oxidase (purple bars) from control and HF animals.
Figure 3A:
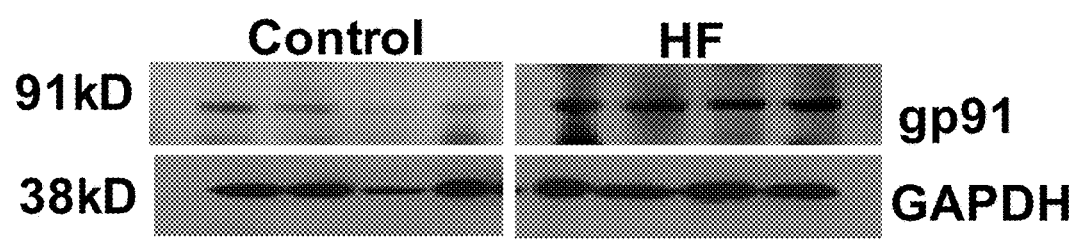
FIG. 3A shows, using western blotting with an anti-gp91 antibody that NOX2 (91-kDa protein subunit) was increased in the HF PLA relative control PLA (GAPDH control protein (38-kDa) is shown for comparison to normalize for loading differences in the gel lanes).

The pharmaceutical compositions have therapeutic efficacy in treating oxidative stress in a subject having atrial or ventricular arrhythmias, ventricular failure or heart failure. A pharmaceutical composition comprising a NOX2 shRNA has demonstrable activity in an art-accepted canine model for human AF. Experiments were performed with normal and HF animals to validate the utility of the canine model to study NOX2 knockdown assays and their effect on NOX2 expression and superoxide production. The HF animals produced superoxide at higher levels in the posterior left atrium (PLA) than in the left atrial appendage (LAA) as compared to normal animals (FIG. 2A). NADPH oxidase is a major source of superoxide generation in PLA from HF animals compared to normal animals (FIG. 2B) depicts contribution of $O_2^-$ production in PLA for NADPH oxidase (blue bars), Mitochondrial ROS (red bars), NOS (green bars) and Xanthine oxidase (purple bars). Furthermore, HF animals display higher levels of NOX2 polypeptide subunit (gp91) as compared to normal animals (FIG. 3A, B).

Figure 5:
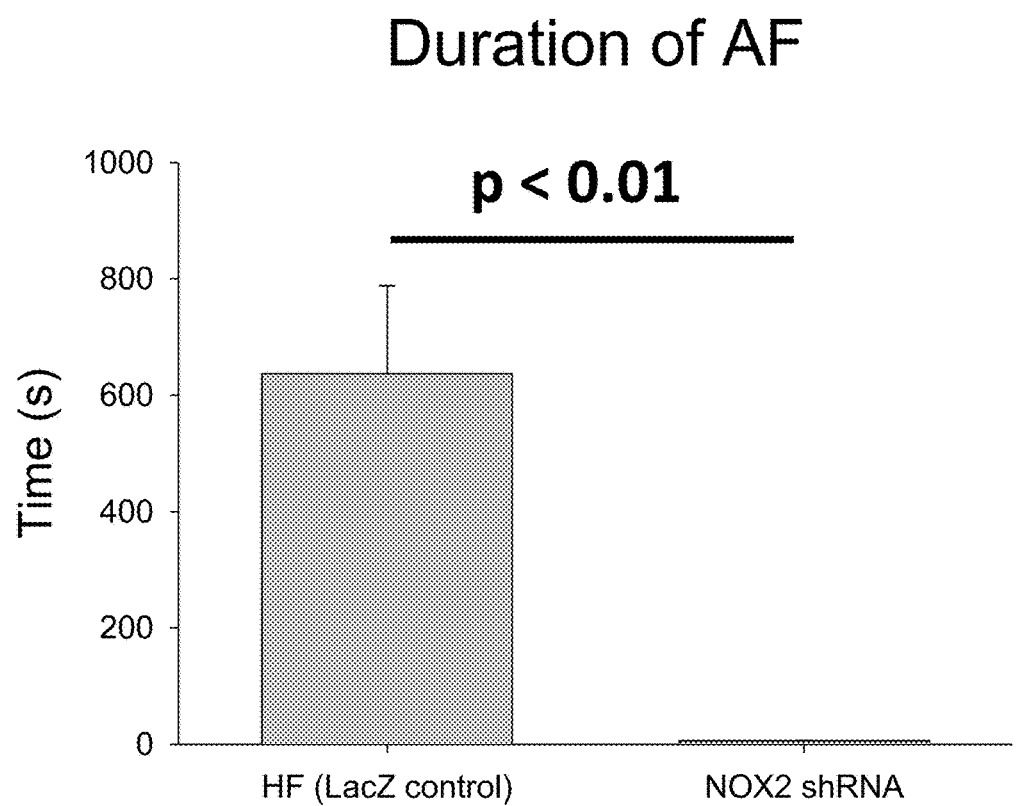
FIG. 5 shows that the duration of AF (seconds) is decreased in plasmid encoding NOX2 shRNA-treated animals ("NOX2 shRNA") compared with lacZ-transfected control animals ("HF(LacZ Control)").

A plasmid encoding either NOX2 shRNA (FIG. 4 and SEQ ID NOs: 1 and 2) or a control RNA (lac Z) was introduced into PLA tissues of HF animals and the effects on AF were evaluated. The duration of AF (seconds) is decreased in plasmid encoding NOX2 shRNA-treated animals ("NOX2 shRNA") compared with lacZ-transfected control animals ("HF(LacZ Control)") (FIG. 5). Moreover, expression of ox-CAMKII in the PLA of HF dogs transfected with NOX2 shRNA (FIG. 6B) is lower than expression of ox-CAMKII in the PLA of HF dogs (FIG. 6A), which is consistent with NOX2 shRNA knocking down NOX2 expression and lowering oxidative stress in atrial tissues.

Figure 7:
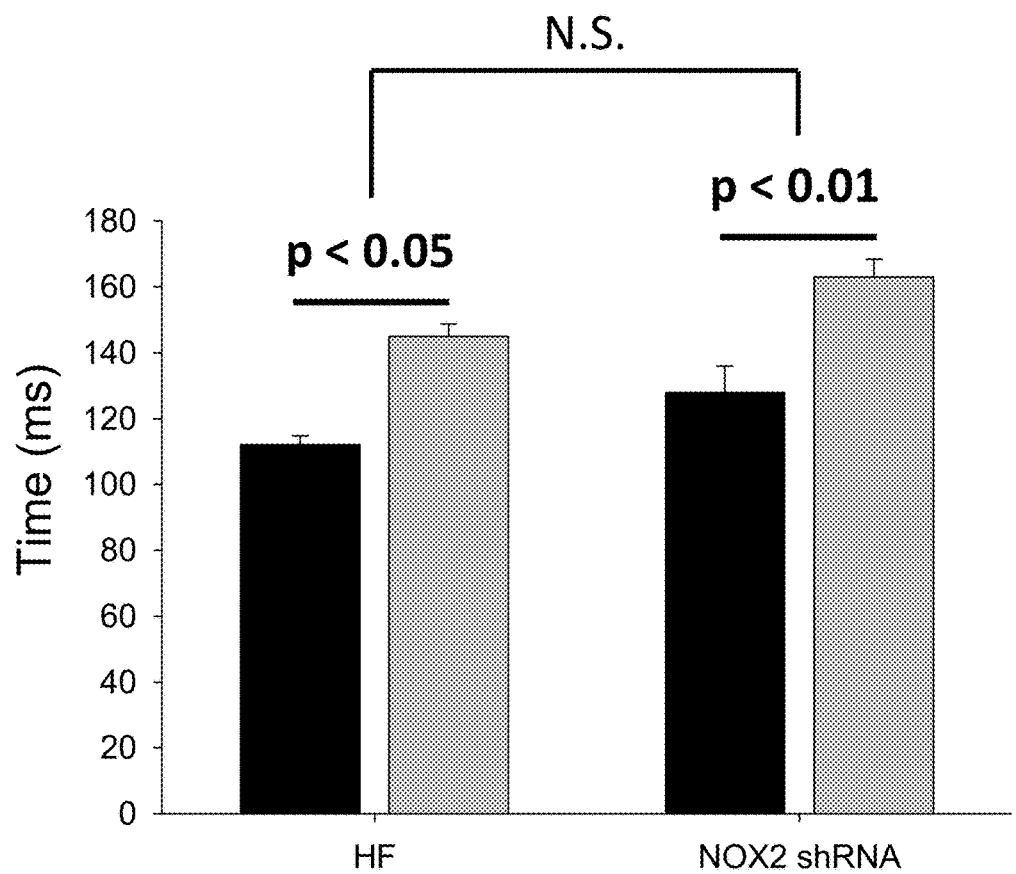
FIG. 7 depicts changes in ERP in plasmid encoding NOX2 shRNA-treated animals (NOX2 shRNA) compared with lacZ-transfected control animals (HF) for baseline (black bars) and post-pacing (grey bars) conditioned animals.
Figure 8A:
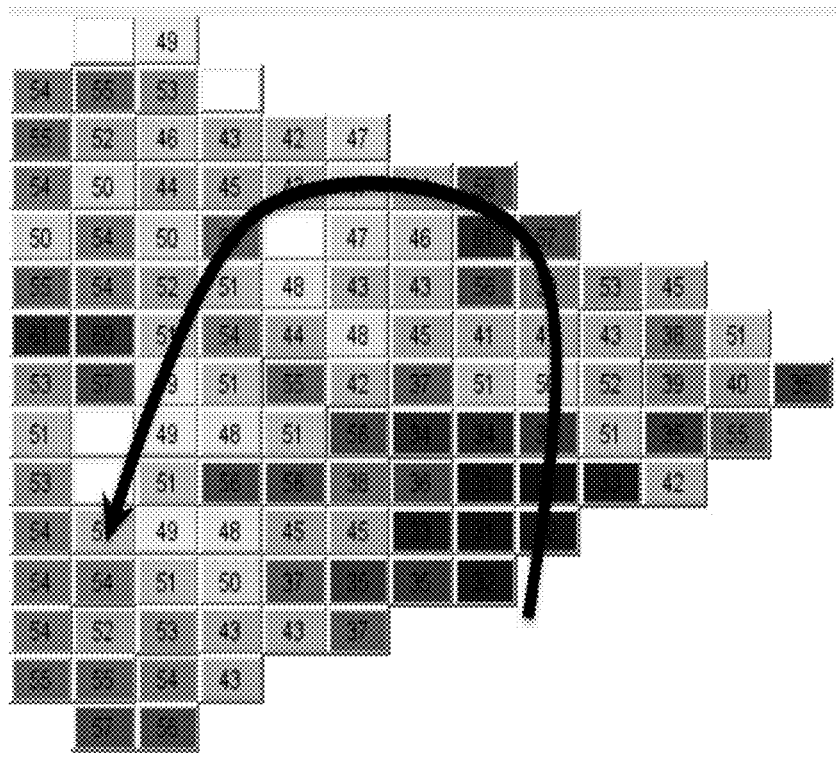
FIG. 8A depicts conduction inhomogeneity index (3.25) for PLA from control HF animals.
Figure 8B:
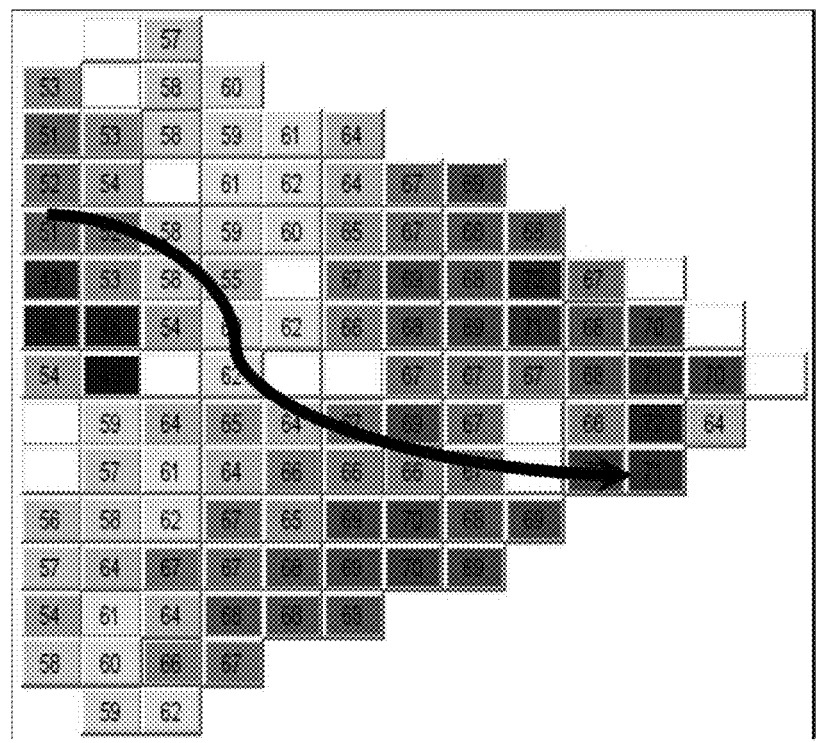
FIG. 8B depicts conduction inhomogeneity index (1.5) for PLA from animals transfected with plasmid encoding NOX2 rhRNA in PLA tissue.
Figure 8C:
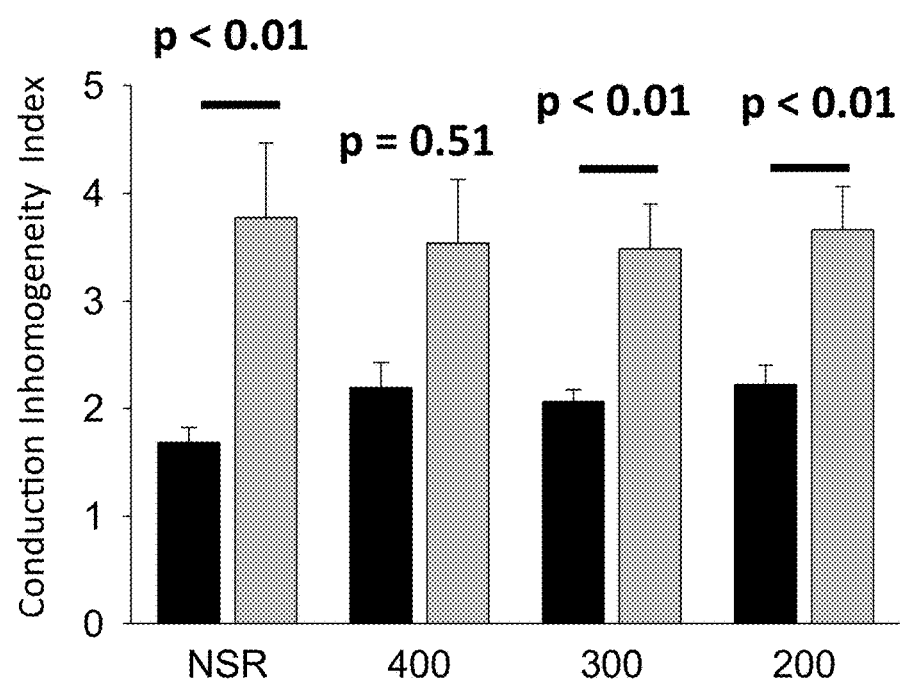
FIG. 8C depicts statistical differences in conduction inhomogeneity indices for PLA from HF animals at day 1 (black bars) and termination (grey bars).
Figure 8D:
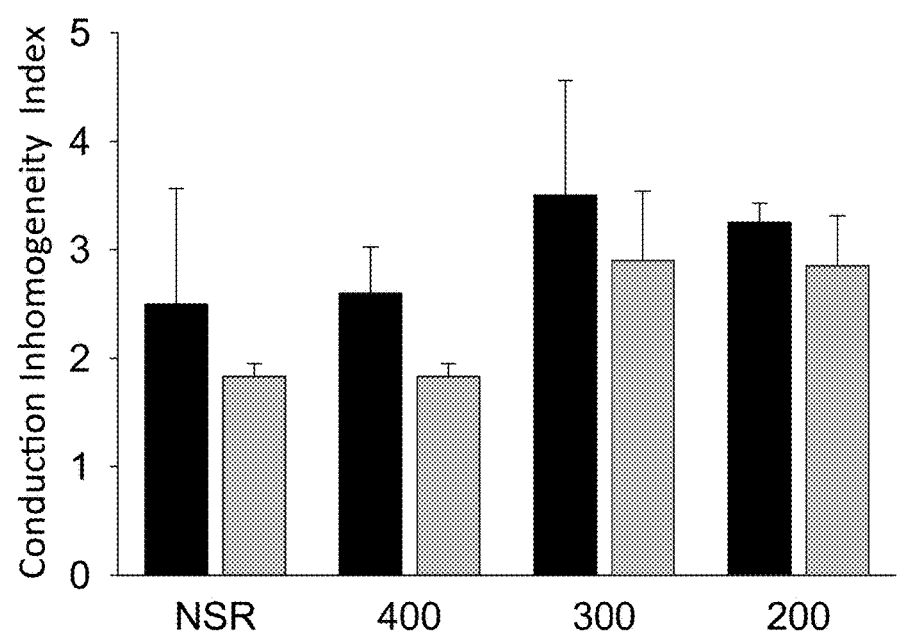
FIG. 8D depicts no statistical difference in conduction inhomogeneity indices for PLA from animals transfected with plasmid encoding NOX2 rhRNA in PLA tissue.

Electrophysiological measurements were recorded for animals following 3 weeks of rapid atrial pacing. Effective Refractory Periods (ERPs) were increased significantly following pacing conditioning; however, ERPs did not change significantly as a function of NOX2 knockdown using NOX2 shRNA (FIG. 7). Conduction was less heterogeneous in PLA transfected with plasmid encoding NOX2 shRNA compared to PLA transfected with control plasmid (FIGS. 8A, B) and NOX2 shRNA abolished significant change noted in the conductive inhomogeneity index (FIG. 8C, D).

Figure 9A:
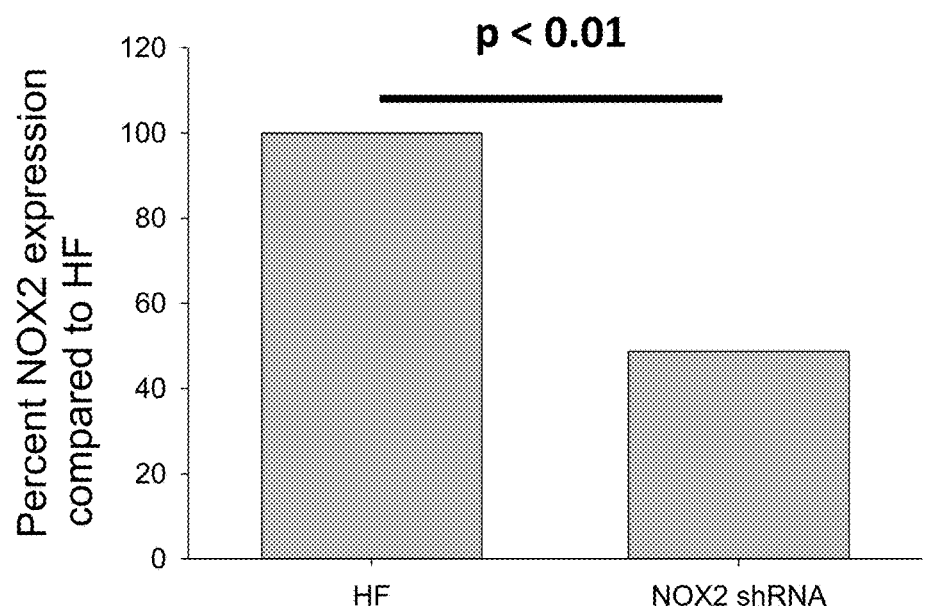
FIG. 9A depicts rtPCR analysis of NOX2 mRNA in PLA from control HF animals as compared to animals with plasmid encoding NOX2 shRNA-transfected PLA.
Figure 10:
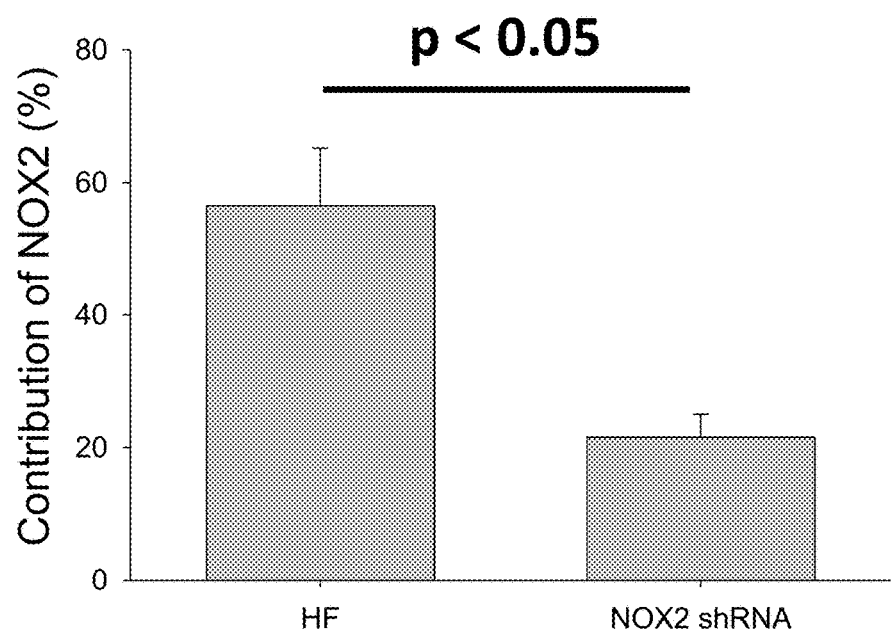
FIG. 10 depicts representative $O_2^-$ levels attributed to NADPH oxidase (NOX2) in PLA from control HF animals as compared to animals with plasmid encoding NOX2 shRNA-transfected PLA.

NOX2 mRNA and protein is reduced in PLA transfected with plasmid encoding NOX2 shRNA compared to PLA transfected with control plasmid (FIG. 9A, B). Similarly, the relative contribution of superoxide production attributed to NADPH oxidase is lower in PLA transfected with plasmid encoding NOX2 shRNA compared to PLA transfected with control plasmid (FIG. 10).

Figure 11A:
FIG. 11A depicts the extent of fibrosis in PLA from control HF animals.
Figure 11B:
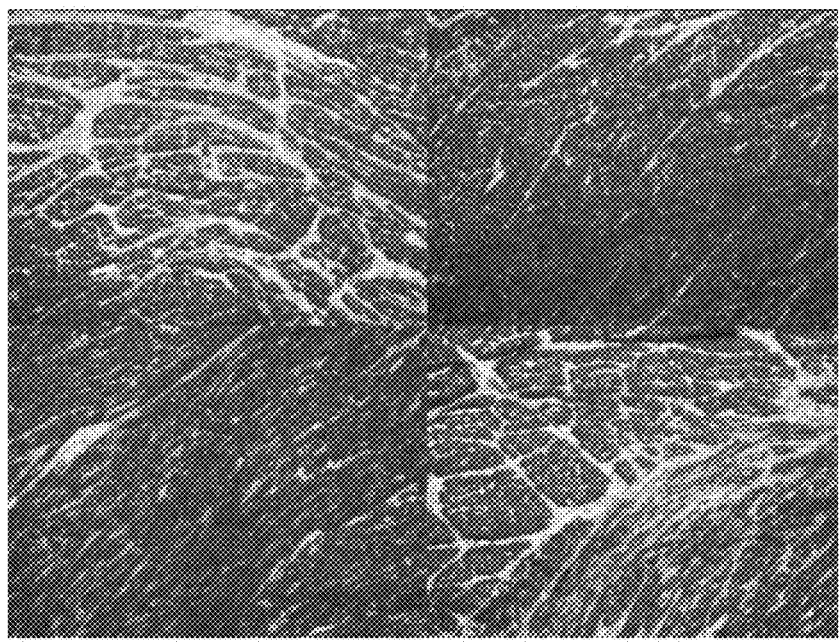
FIG. 11B depicts the extent of fibrosis in PLA from animals with plasmid encoding NOX2 shRNA-transfected PLA.
Figure 11C:
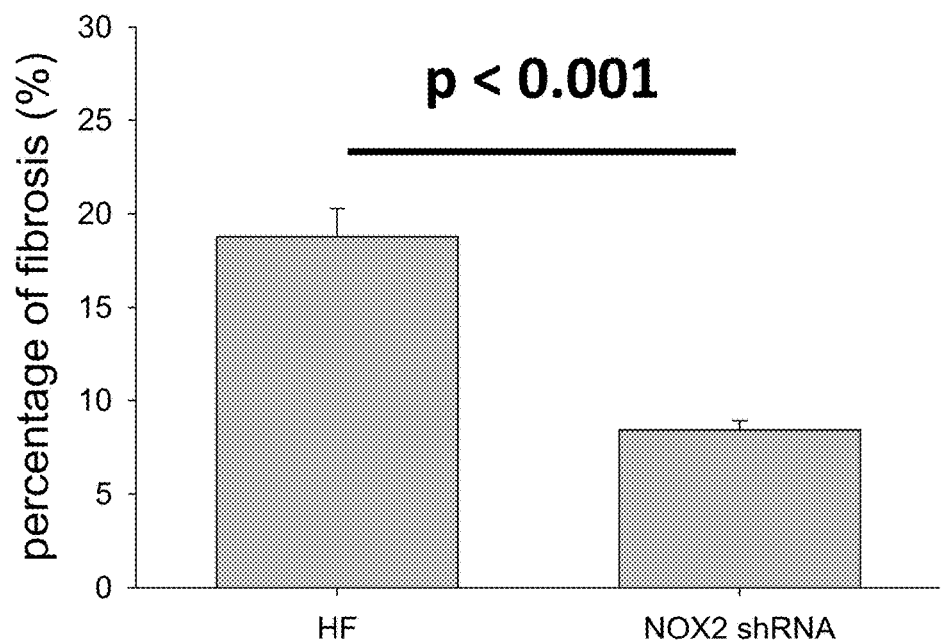
FIG. 11C depicts a quantitative analysis of the percentage of fibrosis in PLA from control HF animals transfected with control plasmid (that is, not encoding NOX2 shRNA).

In addition to using traditional heart monitoring methodologies to detect the presence and absence of AF as a function of NOX2 shRNA therapy, AF EGM characteristics can be systematically assessed to evaluate structural remodeling of atrial tissue in candidate subjects as well as therapeutic efficacy of the pharmaceutical compositions for inhibiting oxidative stress for subjects suffering from chronic AF. Subjects who suffer from chronic AF have structural remodeled atrial tissue with fibrosis. In this regard, fibrosis was reduced in animals whose PLA was transfected with plasmid encoding NOX2 shRNA compared to control animals (FIG. 11A-C).

Application of EGM-guided identification and monitoring of fibrosis-associated structural remodeling of atrial tissue in AF and HF is summarized by related patent application publications by the inventors, such as application entitled "INHIBITION OF FIBROSIS AND AF BY TGF-BETA INHIBITION IN THE POSTERIOR LEFT ATRIUM (PLA)" to Rishi Arora, bearing Ser. No. 13/890,116, filed May 8, 2013, now U.S. Patent Application Publication US 2014-0037545 A1 and application entitled "USING INTRACARDIAC ELECTROGRAMS TO PREDICT LOCATION OF FIBROSIS AND AUTONOMIC NERVES IN THE HEART" to Rishi Arora et al., bearing Ser. No. 13/890,112, filed May 8, 2013, now U.S. Patent Application Publication US 2013-0324869A1.

Figure 12:
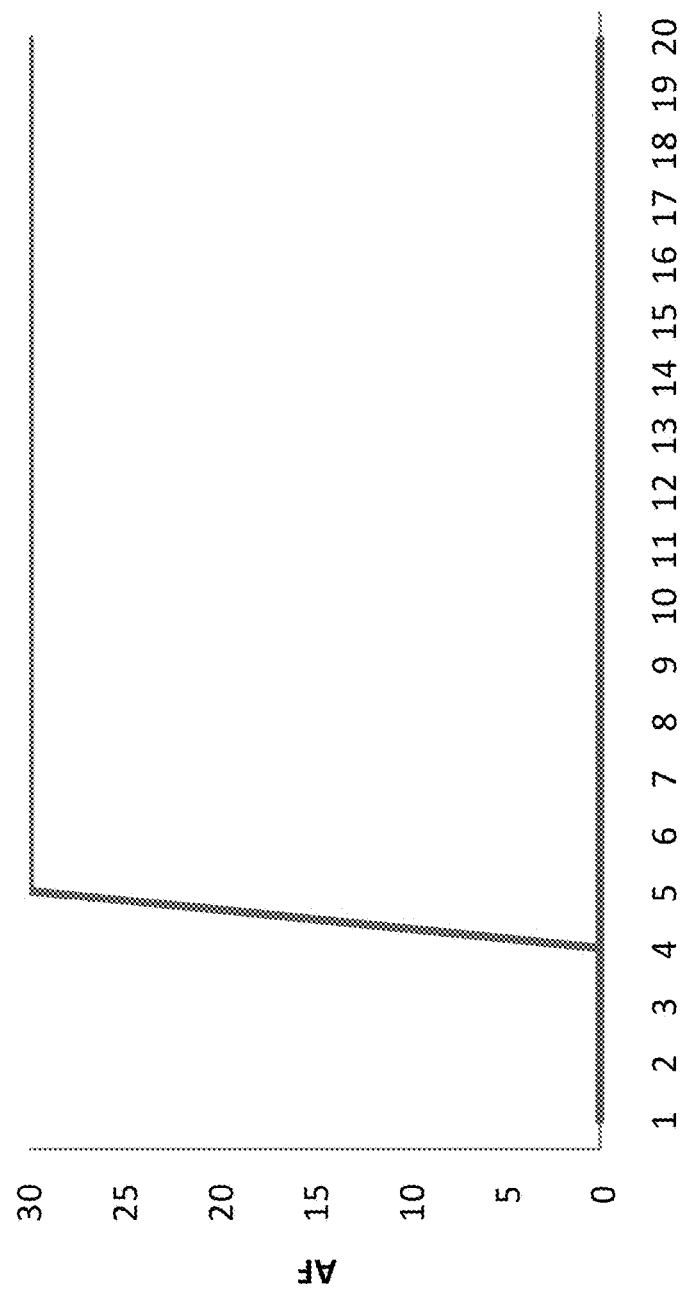
FIG. 12 depicts the onset of AF in a rapid atrial pacing canine model where three control animals experienced sustained AF (blue line) compared with the absence of AF onset in two animals with plasmid encoding NOX2 shRNA-transfected PLA (red line).

In another model, electrical remodeling of atrial tissues can lead to spontaneous AF. Such a model reflects AF in a subject who otherwise might not have significant structural remodeling of atrial tissue due to fibrosis (for example, young subjects). Pacemakers can be used to generate rapid tachypacing in the canine model of electrical remodeling of atrial tissue. Heart monitors (for example, ECG or EKG patterns) can be used to detect AF development as well as the efficacy of NOX2 shRNA treatment efficacy in atrial tissues by measuring the decline or absence of AF following treatment. In this regard, the onset of AF episodes was blocked in animals whose PLA was transfected with plasmid encoding NOX2 shRNA, as compared to normal animals following rapid atrial pacing of the animals (FIG. 12).

Applicability to Other NOX2 Inhibitors.

The results of the NOX2 shRNA studies demonstrate the feasibility of a general strategy to inhibit NADPH oxidase by targeting NOX2 using NOX2 inhibitors. Such inhibitor agents include oligonucleotide-based compounds that target the NOX2 mRNA or protein, such as RNAi molecules and shRNAs directed against NOX2 mRNA and oligonucleotide-based aptamers directed against the NOX2 polypeptide. Furthermore, small molecule organic compounds having anti-NADPH oxidase activity by specifically binding to or otherwise interfering with NOX2 protein functionality can also reduce NADPH oxidase-mediated superoxide production and oxidative stress in AF.

In some embodiments, NOX2 inhibitors comprise any suitable bioactive molecules (e.g. a molecule capable of inhibiting the function of NADPH oxidase). In some embodiments, a NOX2 inhibitor comprises a macromolecule, polymer, a molecular complex, protein, peptide, polypeptide, nucleic acid, carbohydrate, small molecule, etc.

In some embodiments, a NOX2 inhibitor is a NOX2 inhibitory peptide. In some embodiments, the present invention provides peptides of any suitable amino acid sequence capable of inhibiting one or more alleles of NOX2. In some embodiments, peptides provided by or encoded by the compositions of embodiments of the present invention may comprise any arrangement of any standard amino acids (e.g. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) or non-standard amino acids (e.g. D-amino acids, chemically or biologically produced derivatives of common amino acids, selenocysteine, pyrrolysine, lanthionine, 2-aminoisobutyric acid, dehydroalanine, etc.). In some embodiments, NOX2 inhibitory peptides are inhibitors to NOX2.

In some embodiments, NOX2 inhibitory peptides are provided to a subject as isolated or purified peptides. In some embodiments, NOX2 inhibitory peptides are provided to a subject as nucleic acid molecules that encode such peptides. In some embodiments, peptides are optimized to enhance cell penetration (e.g. sequence optimization, sequence tag, tagged with a small molecule, etc.).

In some embodiments, a NOX2 inhibitor is provided from an isolated nucleic acid comprising a minigene, wherein said minigene encodes a modified NOX2 peptide, wherein the peptide blocks the site of interaction between NOX2 and NOX2 binding partners in a cell, such as a human cell. In addition, the minigene can further comprise one or more of a promoter, a ribosomal binding site, a translation initiation codon, and a translation termination codon. In some embodiments, the minigene encodes a modified NOX2. peptide having one of the following general formulas: MGX, MX, and MZX, wherein M is a methionine amino acid residue, wherein G is a glycine amino acid residue, wherein Z is an amino acid residue other than a glycine amino acid residue, and wherein X is a NOX2. peptide which comprises an amino acid sequence from the NOX2. subunit, and has the property of binding a NOX2 binding partner. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous amino acid residues of the NOX2 subunit.

In some embodiments, the NOX2 inhibitor is provided as an isolated or purified polypeptide. In some embodiments, the peptide has a general formula selected from the group consisting of MGX, MX, and MZX, wherein M is a methionine amino acid residue, wherein G is a glycine amino acid residue, wherein Z is an amino acid residue other than a glycine amino acid residue, and wherein X is a NOX2-derived peptide which comprises an amino acid sequence of the NOX2. subunit, and has the property of binding a NOX2 binding partner. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous amino acid residues of the NOX2 subunit.

In some embodiments, the present invention provides methods of inhibiting a NOX2-mediated signaling event in a cell or tissue. These methods comprise administering to a cell or tissue, preferably a human cell or tissue, one of a modified NOX2 peptide and an isolated nucleic acid comprising a minigene which encodes a modified NOX2 peptide, whereby following the administration, the NOX2 peptide inhibits the NOX2-mediated signaling event in the cell or tissue.

In some embodiments, a NOX2 inhibitor comprises a small molecule. In some embodiments, the present invention provides a small molecule inhibitor of NOX2. In some embodiments, the present invention provides a small molecule drug or pharmaceutical compound configured to or capable of inhibiting NOX2 activity, function expression, or the like.

In some embodiments, the present invention provides RNAi molecules (e.g., that alter NOX2 expression) as a NOX2 inhibitor. In some embodiments, the present invention targets the expression of NOX2 genes using nucleic acid based therapies. For example, in some embodiments, the present invention employs compositions comprising oligomeric antisense or RNAi compounds, particularly oligonucleotides, for use in modulating the function of nucleic acid molecules encoding NOX2 genes, ultimately modulating the amount of NOX2 protein expressed. In some embodiments, RNAi is utilized to inhibit NOX2 gene function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

In some embodiments, NOX2 expression is modulated using antisense compounds that specifically hybridize with one or more nucleic acids encoding NOX2. The specific hybridization of an oligomeric compound with its target nucleic acid interferes with the normal function of the nucleic acid. This modulation of function of a target nucleic acid by compounds that specifically hybridize to it is generally referred to as "antisense."

In some embodiments, the present invention contemplates the use of any genetic manipulation for use in modulating the expression of NOX2 genes. Examples of genetic manipulation include, but are not limited to, gene knockout (e.g., removing the NOX2 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter.

In some embodiments, the present invention provides antibodies that target NOX2 protein. Any suitable antibody (e.g., monoclonal, polyclonal, or synthetic) may be utilized in the therapeutic methods disclosed herein. In preferred embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the present invention provides methods of enhancing entry of a NOX2 inhibitor into cells or tissue. In some embodiments, the present invention provides administering a NOX2 inhibitor in conjunction with electroporation, electropermeabilization, or sonoporation. In some embodiments, the present invention provides administering a NOX2 inhibitor in conjunction with electroporation. In some embodiments, the present invention provides co-injection/electroporation of the tissue of a subject. In some embodiments, the present invention provides administering a NOX2 inhibitor prior to, simultaneously with, and/or following electroporation. In some embodiments, electroporation provides a method of delivering pharmaceuticals or nucleic acids (e.g. DNA) into cells. In some embodiments, tissue electrically stimulated at the same time or shortly after pharmaceutical or DNA is applied (e.g. NOX2 inhibitor). In some embodiments, electroporation increases cell permeability. The permeability or the pores are large enough to allow the pharmaceuticals and/or DNA to gain access to the cells. In some embodiments, the pores in the cell membrane close and the cell once again becomes impermeable or less permeable. Devices for co-injection/electroporation are known in the art (U.S. Pat. No. 7,328,064, herein incorporated by reference in its entirety).

Furthermore, though the canine model utilized PLA as model atrial tissue, the approach is applicable to all atrial tissues. In some embodiments, the present invention provides compositions and methods to treat or prevent conditions and/or diseases of the heart (e.g. rhythm disturbances (e.g. atrial fibrillation)). In some embodiments, the present invention provides treatment or prevention of a heart disease or condition selected from the list of aortic dissection, cardiac arrhythmia (e.g. atrial cardiac arrhythmia (e.g. premature atrial contractions, wandering atrial pacemaker, multifocal atrial tachycardia, atrial flutter, atrial fibrillation, etc.), junctional arrhythmias (e.g. supraventricular tachycardia, AV nodal reentrant tachycardia, paroxysmal supraventricular tachycardia, junctional rhythm, junctional tachycardia, premature junctional complex, etc.), atrio-ventricular arrhythmias, ventricular arrhythmias (e.g. premature ventricular contractions, accelerated idioventricular rhythm, monomorphic ventricular tachycardia, polymorphic ventricular tachycardia, ventricular fibrillation, etc.), etc.), congenital heart disease, myocardial infarction, dilated cardiomyopathy, hypertrophic cardiomyopathy, aortic regurgitation, aortic stenosis, mitral regurgitation, mitral stenosis, Ellis-van Creveld syndrome, familial hypertrophic cardiomyopathy, Holt-Orams Syndrome, Marfan Syndrome, Ward-Romano Syndrome, and/or similar diseases and conditions.

In some embodiments, the present invention provides compositions and methods to treat atrial fibrillation. Atrial fibrillation is the commonest rhythm disturbance of the heart. The posterior left atrium and pulmonary veins have been shown to play an important role in the genesis of atrial fibrillation. More recent studies demonstrate a role for the autonomic nervous system, especially the parasympathetic nervous system, in the genesis of atrial fibrillation from the posterior left atrium. Current therapies to manage atrial fibrillation remain ineffective, while novel links, including autonomic activity described here, provide for beneficial treatment options. Work conducted during the development of embodiments of the present invention shows that selective disruption of autonomic pathways in the posterior left atrium can significantly modify the ability to the heart to sustain atrial fibrillation. In particular, embodiments of the present invention treat atrial fibrillation by administration of NOX2 inhibitors. An understanding of the mechanism of action is not necessary to practice the present invention and the present invention is not limited to any particular mechanism of action. The present invention also provides compositions and methods for researching atrial fibrillation, including screening for compounds useful in treating, prevent, or reducing signs or symptoms associate with atrial fibrillation.

EXAMPLES

The invention will be more fully understood upon consideration of the following non-limiting examples, which are offered for purposes of illustration, not limitation.

Example 1

HF Canine Model of Structural Remodeling and AF

Dog Protocols.

Purpose-bred hound dogs (weight range: 25-35 kg; age rage: 1-3 years) used in this study were maintained in accordance to the Guide for the Care and Use of Laboratory Animals published by the U.S. National Institutes of Health (NIH Publication No. 85-23, revised 1996) as approved by the Animal Care and Use Committee of Northwestern University. Before undergoing the procedures listed below, all animals were sedated with diazepam 0.22 mg/kg IM and were induced with propofol (3-7 mg/kg IV). After animals were unresponsive, they were intubated and positive-pressure ventilated, and anesthesia was maintained with isoflurane 0.5-1.5%. The surgical field was scrubbed with chlorhexidine and isopropyl alcohol, sprayed with betadine solution, and draped with sterile towels and sheets. The chest was then opened via a left lateral thoracotomy.

Eleven hounds were randomized into 2 groups: 1) control (n=7) expressing LacZ and 2) gene therapy with a plasmid expressing NOX2 shRNA (n=4). During an initial procedure, a left lateral thoracotomy was performed and the pericardium was incised; animals underwent invasive electrophysiology study (EPS), gene injection, echocardiogram and epicardial implantation of a left ventricular pacemaker. After animals were allowed to recover for 3-5 days, ventricular tachypacing was initiated at 240 bpm. Clinical status assessment and pacing was verified daily. Three weeks after the initial procedure, animals underwent terminal echocardiogram, EPS and cardiac extraction for histology and molecular studies.

Initial Open Chest Electrophysiological Mapping

Effective Refractory Periods (ERPs).

ERPs were obtained using two rectangular plaques epicaridally positioned on the PLA and LAA. Each plaque had 21 electrodes each (7×3 electrodes, inter-electrode distance=5 mm). A Bloom stimulator interfaced with a GE Prucka Cardiolab system (GE Healthcare, Waukesha, Wis.) were used to perform programmed stimulation. ERPs were measured by delivering an 8 pulse drive train at 400 ms coupled to a premature stimulus. The coupling interval of the premature stimulus was decreased in 10 ms increments, and the ERP was defined as the longest coupling interval that fails to conduct. ERPs were obtained from five distributed sites in the both the PLA and LAA. FIG. 7 depicts changes in ERP in plasmid encoding NOX2 shRNA-treated animals (NOX2 shRNA) compared with lacZ-transfected control animals (HF) for baseline (black bars) and post-pacing (grey bars) conditioned animals.

AF Induciblility.

AF was induced with burst pacing at maximum output using cycle lengths of 180 ms to 100 ms with 10 ms decrements for 10 seconds for each cycle length. Current was set at four times threshold for capture. AF induction was defined as episodes lasting more than 30 seconds.

Activation Mapping.

High density activation mapping was performed using a UNEMAP mapping system (Univ. of Auckland, Auckland, New Zealand). A triangular plaque containing 130 electrodes (inter-electrode distance of 2.5 mm) were used to record 117 bipolar EGMs at a 1 kHz sampling rate. Mapping was performed sequentially in the LAA and in two adjacent sites in the PLA. At each site, 10 second recordings were made during sinus rhythm and pacing with cycle lengths of 400, 300, and 200 ms. Pacing was performed in LAA when recording from the PLA and vice versa.

Data Analysis with Conduction Inhomogeneity.

MATLAB (Mathworks, Natick, Mass.) was used for all offline signal analysis in this study. Conduction inhomogeneity analysis was performed using the high density UNEMAP recordings obtained during sinus rhythm and pacing. The bipolar electrograms were highpass filtered at 30 Hz, rectified, and then lowpass filtered at 20 Hz. The times of the filtering peaks were considered the activation time for that activation. Conduction inhomogeneity was calculated as described by Lammers W J, Schalij M J, Kirchhof C J, Allessie M A. Quantification of spatial inhomogeneity in conduction and initiation of reentrant atrial arrhythmias. Am J Physiol 1990; 259:H1254-63. Total activation time measuring the amount of time to activate the entire area of the plaque was also measured. Total activation time measuring the amount of time to activate the entire area of the plaque was also measured. Exemplary results of these studies are shown in FIG. 8A-D.

Gene Injection/Transfer.

After the completion of the initial EPS, 10 mg of plasmid DNA [control plasmid (pUBc-lacZ) or NOX2 shRNA-encoded plasmid expression vector under the control of the U6 pol III promoter (FIG. 4)] (0.1 mg/each site) was directly injected transmurally in the PLA with a 27-gauge needle. Electric pulses were delivered to the myocardium through the electrodes spaced 1 cm apart (Genetrodes, BTX). Immediately after the injection, 8 electrical pulses (amplitude, 200 V; duration, 10 ms; intervals, 1 sec) were delivered with a square-wave electroporation generator (ECM 830, BTX, Harvard Apparatus).

HF Induction.

In 11 dogs, HF was induced by 3 to 4 weeks of right ventricular tachypacing (240 beats per minute) by an implanted pacemaker. In all dogs, a pacemaker was placed on the ventricle via an epicardial approach (that is, via a left lateral thoracotomy). Left ventricular function was assessed during pacing by serial echocardiograms (data not shown). HF was confirmed after 3 to 4 weeks of pacing.

Terminal Surgery and Open Chest Electrophysiology Mapping.

At the terminal study, a left lateral thoracotomy was performed. Low density and high density mapping protocols were used. With low density mapping, the posterior left atrium (PLA), left superior pulmonary vein (PV), and left atrial appendage could be mapped simultaneously. The PLA and LAA were mapped using two rectangular plaques containing 21 electrodes each (7×3 electrodes, inter-electrode distance=5 mm) from which 18 bipolar EGMs were recorded. FIG. 3A shows the schematics of the plaques. The signals from the low density plaques were recorded and stored at a 977 Hz sampling rate with the GE Prucka Cardiolab system (GE Healthcare, Waukesha, Wis.).

High density mapping was performed in all dogs for more detailed electrophysiological analysis, including assess of conduction heterogeneity (inhomogeneity). Mapping was performed sequentially in the PLA and LAA with a triangular plaque containing 130 electrodes (inter-electrode distance of 2.5 mm) from which 117 bipolar electrograms (EGMs) were recorded. The UNEMAP mapping system (Univ. of Auckland, Auckland, New Zealand) was used for recording and storing the EGMs at a 1 kHz sampling rate. Even though we did not separately map the PVs during high-density mapping (owing to the relatively large surface area of the high density plaques, it was technically challenging to cover the PVs, which have a circular and uneven surface), the high-density plaque did straddle the proximal PVs during PLA mapping.

Example 2

Rapid Atrial Pacing (RAP) Canine Model of Electrical Remodeling and Spontaneous AF A transvenous pacemaker was placed in the right atrium (RA) via a jugular venous approach. One week later, the animal underwent a left lateral thoracotomy. Open chest electrophysiological mapping was performed as follows:

Initial Open Chest Electrophysiological Mapping

Effective Refractory Periods (ERPs).

ERPs were obtained using two rectangular, 21-electrode plaques epicardially positioned on the PLA and LAA. ERPs were obtained from five evenly distributed sites in the both the PLA and LAA.

AF Induciblility.

AF was induced with burst pacing. AF was defined as episodes lasting more than 3 seconds. Sustained AF was defined as AF>60 seconds.

Activation Mapping.

High density activation mapping was performed using the UNEMAP mapping system (Univ. of Auckland, Auckland, New Zealand). A triangular plaque containing 130 electrodes (inter-electrode distance of 2.5 mm) were used to record 117 bipolar EGMs at a 1 kHz sampling rate. Mapping was performed sequentially in the LAA and in two adjacent sites in the PLA. At each site, 10 second recordings were made during sinus rhythm and pacing with cycle lengths of 400, 300, and 200 ms.

Gene Injection/Transfer.

After the completion of the initial electrophysiological study, 10 mg of plasmid [control plasmid (pUBc-lacZ) or NOX2 shRNA-encoded plasmid expression vector under the control of the U6 pol III promoter (FIG. 4)] (diluted in 5 ml sterile saline) was injected sub-epicardially in the PLA with a 27-gauge needle; 5-6 injections (approximately 1 ml each) were used to cover the entire PLA. After gene injection, electroporation was performed at each site of gene injection (200 V; duration, 10 ms; intervals, 1 sec).

Rapid Atrial Pacing.

After the initial open-chest mapping study and gene injection, the chest was closed and the animal allowed to recover for 1 week. Rapid atrial pacing (at 600 beats/min) was then started, and continued for the next 3 weeks. FIG. 12 illustrates that dog recipients of NOX2 shRNA-encoded plasmid expression vector injected into PLA tissue did not develop spontaneous AF following rapid atrial pacing.

Serial Testing for Sustained AF.

Every 24-48 hours, pacing was stopped for 30-60 minutes, in order to assess for onset of AF and for duration of the induced AF.

Terminal Surgery and Open Chest Electrophysiology Mapping.

After 3 weeks of rapid atrial pacing (RAP), repeat open chest electrophysiological mapping was performed. If the animal reverted to sinus rhythm, atrial effective refractory periods were assessed. AF electrograms were also recorded.

After the electrophysiological study was completed, the heart was removed and the atria snap frozen. The atria was subjected to further analysis to assess for gene expression, expression of key signaling molecules etc.

Example 3

Histology and Tissue Analysis

The histologic analysis described below was performed on atrial tissues from untreated and treated dogs receiving plasmids expressing NOX2 shRNA or an inactive control RNA (lac Z) were analyzed.

Tissue Sample Preparation.

In the animals undergoing high density mapping, immediately following the in vivo electrophysiological study, the heart was promptly excised out of the chest and immersed in ice-cold cardioplegia as previously described by us. After marking the exact orientation of the high density plaques, tissue samples were taken from the PLA and LAA regions of the left atrium and snap frozen in liquid nitrogen. Samples were saved in the exact orientation in which high density mapping had been performed. All samples were initially saved at −80° C. The oriented tissue samples were frozen in Tissue-Tek OCT (Optimal Cutting Temperature) compound at −80° C.

For paraffinization, the tissue as thawed and a quick wash given to clean off all the OCT. Using a PCF LEICA 1050 Tissue Processor, the tissue was embedded in paraffin. The tissue processor uses 10% NBF (Neutral Buffered Formalin) for fixing and the tissue dehydration is performed with incremental concentrations of Ethanol (ETOH). ETOH is exchanged with xylene and finally xylene is exchanged with paraffin at 58° C. Then tissue is embedded in a paraffin block.

Masson's Trichrome Staining.

Tissue sections were cut 4 μm apart. Paraffin was removed by placing the tissue section in histology grade xylene for two minutes and the process was repeated four times changing xylene solution after every two minutes. Finally, the xylene was washed away with ETOH for one minute in absolute ETOH, then again for one more minute with fresh absolute ETOH, followed by wash in 95% ETOH for 30 seconds, and subsequently in 70% ETOH for 45 seconds. ETOH was then washed with water for one minute. The tissue section was then ready for staining. The section was treated with Bouin's mordant at nom temperature overnight. The following day the tissue section was rinsed in running water to remove excess yellow. The tissue section was stained in Weigert's Solution for 7 minutes. Next, it was dipped once in 1% acid alcohol and immediately rinsed. The section was then stained in Beibrich Scarlet-Acid fuchsin for 2 minutes, followed by a rinse in distilled water. Subsequently, the tissue section was stained in phosphomolybdic-phosphotungstic acid solution for 6 minutes, followed by another rinse in distilled water. The issue section was then stained in Aniline Blue solution for 5 minutes, followed by another rinse in distilled water. Immediately, the tissue was dipped once in 1% Glacial acetic acid and quickly rinsed. The tissue section was then dehydrated in twice in each concentration of 95% and 100% of ETOH, which was later exchanged with xylene. A coverslip was finally placed on the tissue section for microscope examination. Examples of results of such assays are illustrated in FIG. 11A-C.

ox-CAMKII Immunofluorescence.

Figure 6A:
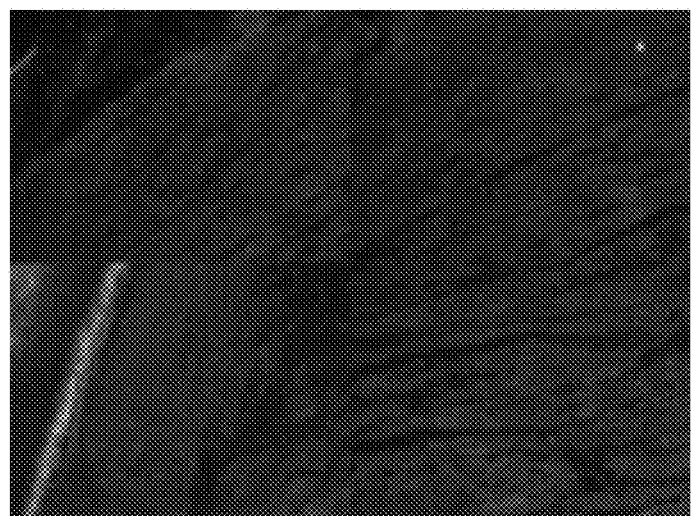
FIG. 6a shows increased expression of ox-CAMKII in PLA of control HF dogs (green fluorescence represents ox-CAMKII).
Figure 6B:
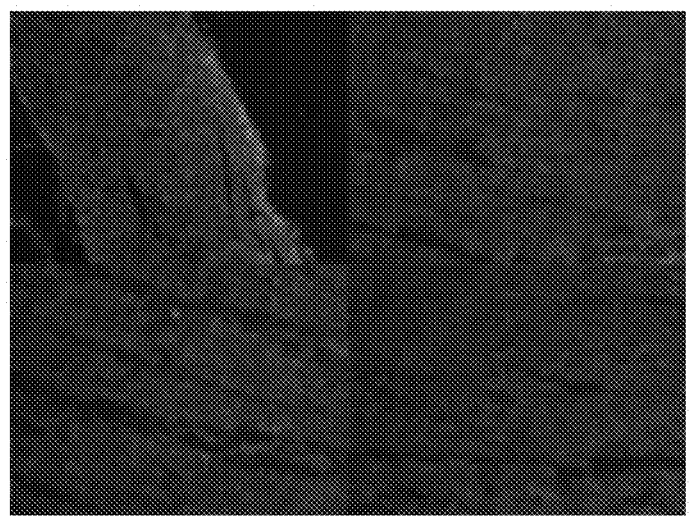
FIG. 6B shows decreased expression of ox-CAMKII in the PLA of HF dogs transfected with NOX2 shRNA (green fluorescence represents ox-CAM KU).

Tissue samples were fixed and stained with anti-ox-CAMKII antibody. Exemplary results of such assays are illustrated in FIG. 6A, B.

Real-Time PCR.

Frozen tissue samples were frozen crushed and homogenized. Total RNA was isolated using Trizol Reagent (Life Technologies, 15596-026). Contaminating DNA was removed using DNA-free DNA Removal Kit (Life Technologies, AM1906). cDNA was synthesized from 0.5 μg of total RNA with TaqMan reverse transcription reagents SuperScript VILO (Life Technologies, #11755050) and mixed with TaqMan Fast Advanced Master Mix (Life Technologies, #4444965). Quantitative real-time PCR (qRT-PCR) was carried out using Applied Biosystems® 7500 Fast Real-Time PCR System (Life Technologies). Relative mRNA levels were calculated by the (type of software) after normalization of each experimental sample to GAPDH levels. An example of results of such assays is illustrated in FIG. 9A.

Western Blot Analysis.

Figure 3B:
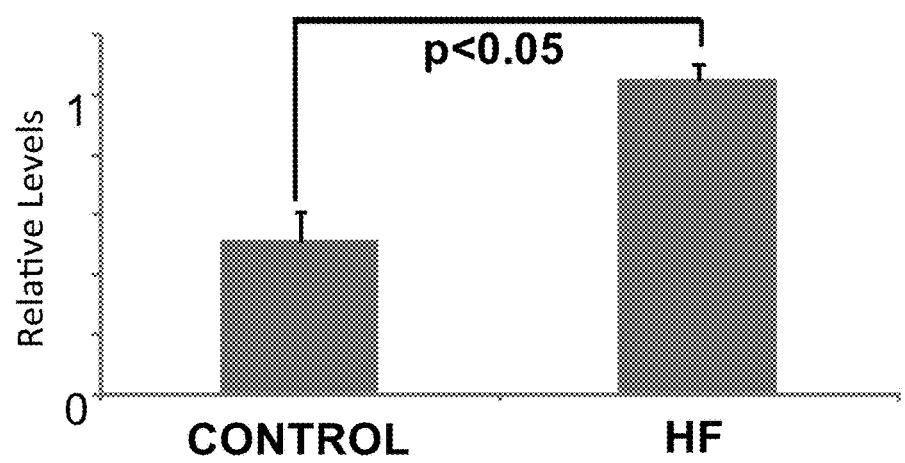
FIG. 3B depicts quantitative results of anti-gp91 antibody (NOX2) data of FIG. 3A.
Figure 9B:
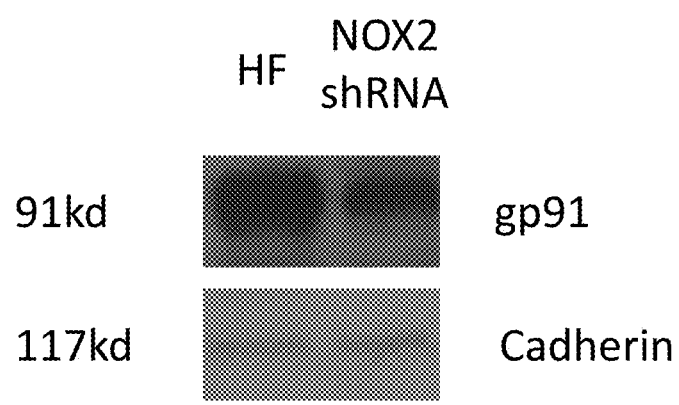
FIG. 9B depicts representative NOX2 protein levels in PLA from control HF animals as compared to animals with plasmid encoding NOX2 shRNA-transfected PLA (cadherin used as a control protein).

The atrial tissue was snap frozen in liquid nitrogen, homogenized, and separated into membrane and cytosolic fractions according to the procedures of the Mem-Per Plus Membrane Protein Extraction Kit (Thermo-Scientific, #89842) or T-Per Tissue Protein Extraction Reagent (Thermo-Scientific, 78510) for total protein. We added Halt Protease & Phosphatase Inhibitor Cocktail (Thermo-Scientific, #78446) to all buffers. Protein concentrations were determined using Pierce BCA Protein Assay Kit (Thermo-Scientific, #23227). Proteins were fractionated by SDS-PAGE, transferred to polyvinyl difluoride (PVDF) membrane, blocked with 5% BSA, and blotted with the appropriate primary and secondary antibodies. Examples of results of such assays are illustrated in FIG. 3 and FIG. 9B.

Measurement of NADPH-Dependent Superoxide Production by Chemiluminescence.

100 mg frozen tissue samples were crushed and rotor homogenized (Biospec Products Inc, Tissue-Tearor) with protease inhibitor (Halt protease and phosphatase inhibitor cocktail, Thermo-Scientific, #1861282). Protein concentrations were determined using Pierce BCA Protein Assay Kit (Thermo-Scientific, #23227). Lucigenin (5 µmol/L) (Enzo Life Sciences, ALX-620-061-M050) and NADPH (100 µmol/L) (Calbiochem, #481973) were each added in the presence and absence of apocynin (Santa Cruz Biotechnology, #sc-203321) (an inhibitor of NADPH oxidase) and mito-TEMPO (Santa Cruz Biotechnology, #sc-221945) (a mitochondrial ROS inhibitor), and the photon outputs were measured using a luminometer (Berthold Technologies, LUMAT LB 9507). An example of this assay is described for PLA and LLA tissue samples from normal and HF dogs in FIG. 2A, B.

REFERENCES

1. Aistrup G C I, Ng J, Gordon D, Koduri H, Browne S, Arapi D, Segon Y, Goldstein J, Angulo A, Wasserstrom J A, Goldberger J, Kadish A, Arora R. Non-viral Gene-based Inhibition of Gi/o-mediated Vagal Signaling in the Posterior Left Atrium Decreases Vagal Induced AF. Heart Rhythm 2011; 8:1722-9.
2. Benjamin E J, Levy D, Vaziri S M, D'Agostino R B, Belanger A J, Wolf P A. Independent risk factors for atrial fibrillation in a population-based cohort. The Framingham Heart Study. JAMA 1994; 271:840-4.
3. Gerstenfeld E P, Sauer W, Callans D J, et al. Predictors of success after selective pulmonary vein isolation of arrhythmogenic pulmonary veins for treatment of atrial fibrillation. Heart Rhythm 2006; 3:165-70.
4. Pappone C, Oral H, Santinelli V, et al. Atrio-esophageal fistula as a complication of percutaneous transcatheter ablation of atrial fibrillation. Circulation 2004; 109:2724-6.
5. Verma A, Patel D, Famy T, et al. Efficacy of adjuvant anterior left atrial ablation during intracardiac echocardiography-guided pulmonary vein antrum isolation for atrial fibrillation. J Cardiovasc Electrophysiol 2007; 18:151-6.
6. Rodrigues A C, Scannavacca M I, Caldas M A, et al. Left atrial function after ablation for paroxysmal atrial fibrillation. American Journal of Cardiology 2009; 103:395-8.
7. Aldhoon B, Melenovsky V, Peichl P, Kautzner J. New insights into mechanisms of atrial fibrillation. Physiological research/Academia Scientiarum Bohemoslovaca 2010; 59:1-12.
8. Jeong E-M, Liu M, Sturdy M, et al. Metabolic stress, reactive oxygen species, and arrhythmia. Journal of Molecular and Cellular Cardiology 2012; 52:454-63.
9. Hool L C. Reactive Oxygen Species in Cardiac Signalling: From Mitochondria to Plasma Membrane Ion Channels. Clinical and Experimental Pharmacology and Physiology 2006; 33:146-51.
10. Zima A V, Blatter L A. Redox regulation of cardiac calcium channels and transporters. Cardiovascular Research 2006; 71:310-21.
11. Nediani C, Raimondi L, Borchi E, Cerbai E. Nitric Oxide/Reactive Oxygen Species Generation and Nitroso/Redox Imbalance in Heart Failure: From Molecular Mechanisms to Therapeutic Implications. Antioxidants & Redox Signaling 2011; 14:289-331.
12. Lijnen P J, van Pelt J F, Fagard R H. Stimulation of reactive oxygen species and collagen synthesis by angiotensin II in cardiac fibroblasts. Cardiovascular therapeutics 2012; 30:e1-8.
13. Nabeebaccus A, Zhang M, Shah A M. NADPH oxidases and cardiac remodelling Heart Fail Rev 2011; 16:5-12.
14. Erickson J R, Joiner M L, Guan X, et al. A dynamic pathway for calcium-independent activation of CaMKII by methionine oxidation. Cell 2008; 133:462-74.
15. Youn J-Y, Zhang J, Zhang Y, et al. Oxidative stress in atrial fibrillation: An emerging role of NADPH oxidase. Journal of Molecular and Cellular Cardiology 2013; 62:72-9.
16. Murdoch C E, Zhang M, Cave A C, Shah A M. NADPH oxidase-dependent redox signalling in cardiac hypertrophy, remodelling and failure. Cardiovasc Res 2006; 71:208-15.
17. Kuroda J, Ago T, Matsushima S, Zhai P, Schneider M D, Sadoshima J. NADPH oxidase 4 (Nox4) is a major source of oxidative stress in the failing heart. Proc Natl Acad Sci USA 2010; 107:15565-70.
18. Yeh Y H, Kuo C T, Chang G J, Qi X Y, Nattel S, Chen W J. Nicotinamide adenine dinucleotide phosphate oxidase 4 mediates the differential responsiveness of atrial versus ventricular fibroblasts to transforming growth factor-beta. Circ Arrhythm Electrophysiol 2013; 6:790-8.
19. Zhang M, Perino A, Ghigo A, Hirsch E, Shah A M. NADPH oxidases in heart failure: poachers or gamekeepers? Antioxid Redox Signal 2013; 18:1024-41.
20. Reilly S N, Jayaram R, Nahar K, et al. Atrial sources of reactive oxygen species vary with the duration and substrate of atrial fibrillation: implications for the antiarrhythmic effect of statins. Circulation 2011; 124:1107-17.
21. Ciaccio E J, Biviano A B, Whang W, Gambhir A, Garan H. Different characteristics of complex fractionated atrial electrograms in acute paroxysmal versus long-standing persistent atrial fibrillation. Heart Rhythm 2010; 7:1207-15.
22. Ciaccio E J, Biviano A B, Whang W, et al. Differences in repeating patterns of complex fractionated left atrial electrograms in longstanding persistent atrial fibrillation as compared with paroxysmal atrial fibrillation. Circ Arrhythm Electrophysiol 2011; 4:470-7.
23. Aistrup G L, Cokic I, Ng J, et al. Targeted nonviral gene-based inhibition of Galpha(i/o)-mediated vagal signaling in the posterior left atrium decreases vagal-induced atrial fibrillation. Heart Rhythm 2011; 8:1722-9.
24. Aistrup G L, Villuendas R, Ng J, et al. Targeted G-protein inhibition as a novel approach to decrease vagal atrial fibrillation by selective parasympathetic attenuation. Cardiovasc Res 2009; 83:481-92.
25. Balasubramaniam R, Kistler P M. AF and Heart failure: the chicken or the egg?. Heart 2009; 95:535-9.
26. Lakshminarayan K, Anderson D C, Herzog C A, Qureshi A I. Clinical epidemiology of atrial fibrillation and related cerebrovascular events in the United States. Neurologist 2008; 14:143-50.
27. Lip G Y, Kakar P, Watson T. Atrial fibrillation—the growing epidemic.[comment]. Heart 2007; 93:542-3.
28. Nademanee K, McKenzie J, Kosar E, et al. A new approach for catheter ablation of atrial fibrillation: mapping of the electrophysiologic substrate. [see comment]. Journal of the American College of Cardiology 2004; 43:2044-53.
29. Nademanee K, Schwab M C, Kosar E M, et al. Clinical outcomes of catheter substrate ablation for high-risk patients with atrial fibrillation. Journal of the American College of Cardiology 2008; 51:843-9.
30. Taylor G W, Kay G N, Zheng X, Bishop S, Ideker R E. Pathological effects of extensive radiofrequency energy applications in the pulmonary veins in dogs. Circulation 2000; 101:1736-42.
31. Estner H L, Hessling G, Ndrepepa G, et al. Electrogram-guided substrate ablation with or without pulmonary vein isolation in patients with persistent atrial fibrillation. Europace 2008; 10:1281-7.
32. Weerasooriya R, Khairy P, Litalien J, et al. Catheter ablation for atrial fibrillation: are results maintained at 5 years of follow-up? J Am Coll Cardiol 2011; 57:160-6.
33. Ben Morrison T, Jared Bunch T, Gersh B J. Pathophysiology of concomitant atrial fibrillation and heart failure: implications for management. Nat Cliin Pract Cardiovasc Med 2009; 6:46-56.
34. Nattel S. From guidelines to bench: implications of unresolved clinical issues for basic investigations of atrial fibrillation mechanisms. Can J Cardiol 2011; 27:19-26.
35. Nattel S, Burstein B, Dobrev D. Atrial remodeling and atrial fibrillation: mechanisms and implications. Circ Arrhythm Electrophysiol 2008; 1:62-73.
36. Youn J Y, Zhang J, Zhang Y, et al. Oxidative stress in atrial fibrillation: an emerging role of NADPH oxidase. J Mol Cell Cardiol 2013; 62:72-9.
37. Maejima Y, Kuroda J, Matsushima S, Ago T, Sadoshima J. Regulation of myocardial growth and death by NADPH oxidase. J Mol Cell Cardiol 2011.
38. Kohlhaas M, Maack C. Interplay of defective excitation-contraction coupling, energy starvation, and oxidative stress in heart failure. Trends Cardiovasc Med 2011; 21:69-73.
39. Maulik S K, Kumar S. Oxidative stress and cardiac hypertrophy: a review. Toxicol Mech Methods 2012; 22:359-66.
40. Hori M, Nishida K. Oxidative stress and left ventricular remodelling after myocardial infarction. Cardiovascular Research 2009; 81:457-64.
41. Tsai K H, Wang W J, Lin C W, et al. NADPH oxidase-derived superoxide anion-induced apoptosis is mediated via the JNK-dependent activation of NF-kappaB in cardiomyocytes exposed to high glucose. J Cell Physiol 2012; 227:1347-57.
42. Erickson J R, He B J, Grumbach I M, Anderson M E. CaMKII in the cardiovascular system: sensing redox states. Physiol Rev 2011; 91:889-915.43. Cave A C, Brewer A C, Narayanapanicker A, et al. NADPH oxidases in cardiovascular health and disease. Antioxid Redox Signal 2006; 8:691-728.
44. Zhang P, Hou M, Li Y, et al. NADPH oxidase contributes to coronary endothelial dysfunction in the failing heart. Am J Physiol Heart Circ Physiol 2009; 296:H840-6.
45. Dworakowski R, Alom-Ruiz S P, Shah A M. NADPH oxidase-derived reactive oxygen species in the regulation of endothelial phenotype. Pharmacol Rep 2008; 60:21-8.
46. Zhang M, Brewer A C, Schroder K, et al. NADPH oxidase-4 mediates protection against chronic load-induced stress in mouse hearts by enhancing angiogenesis. Proc Natl Acad Sci USA 2010; 107:18121-6.
47. Huang C X, Liu Y, Xia W F, Tang Y H, Huang H. Oxidative stress: a possible pathogenesis of atrial fibrillation. Med Hypotheses 2009; 72:466-7.
48. Carnes C A, Janssen P M, Ruehr M L, et al. Atrial glutathione content, calcium current, and contractility. J Biol Chem 2007; 282:28063-73.
49. Carnes C A, Chung M K, Nakayama T, et al. Ascorbate attenuates atrial pacing-induced peroxynitrite formation and electrical remodeling and decreases the incidence of postoperative atrial fibrillation. Circ Res 2001; 89:E32-8.
50. Kim Y M, Guzik T J, Zhang Y H, et al. A myocardial Nox2 containing NAD(P)H oxidase contributes to oxidative stress in human atrial fibrillation. Circ Res 2005; 97:629-36.
51. Cucoranu I, Clempus R, Dikalova A, et al. NAD(P)H Oxidase 4 Mediates Transforming Growth Factor-1—Induced Differentiation of Cardiac Fibroblasts Into Myofibroblasts. Circulation Research 2005; 97:900-7.
52. Zhang J, Youn J Y, Kim A, et al. NOX4-dependent Hydrogen Peroxide Overproduction in Human Atrial Fibrillation and HL-1 Atrial Cells: Relationship to Hypertension. Frontiers in Physiology 2012; 3.
53. Shryock J C, Song Y, Rajamani S, Antzelevitch C, Belardinelli L. The arrhythmogenic consequences of increasing late INa in the cardiomyocyte. Cardiovasc Res 2013; 99:600-11.
54. Aistrup G L, Balke C W, Wasserstrom J A. Arrhythmia triggers in heart failure: the smoking gun of [Ca2+]i dysregulation. Heart Rhythm 2011; 8:1804-8.
55. Antoons G, Sipido K R. Targeting calcium handling in arrhythmias. Europace 2008; 10:1364-9.
56. Laurita K R, Rosenbaum D S. Mechanisms and potential therapeutic targets for ventricular arrhythmias associated with impaired cardiac calcium cycling J Mol Cell Cardiol 2008; 44:31-43.
57. Volders P G, Vos M A, Szabo B, et al. Progress in the understanding of cardiac early afterdepolarizations and torsades de pointes: time to revise current concepts. Cardiovasc Res 2000; 46:376-92.
58. Laurita K R, Rosenbaum D S. Cellular mechanisms of arrhythmogenic cardiac alternans. Prog Biophys Mol Biol 2008; 97:332-47.
59. Chou C C, Nihei M, Zhou S, et al. Intracellular calcium dynamics and anisotropic reentry in isolated canine pulmonary veins and left atrium. Circulation 2005; 111: 2889-97.
60. Li D, Melnyk P, Feng J, et al. Effects of Experimental Heart Failure on Atrial Cellular and Ionic Electrophysiology. Circulation 2000; 101:2631-8.
61. Yeh Y-H, Wakili R, Qi X-Y, et al. Calcium-Handling Abnormalities Underlying Atrial Arrhythmogenesis and Contractile Dysfunction in Dogs With Congestive Heart Failure. Circ Arrhythm Electrophysiol 2008; 1:93-102.
62. Kuster G M, Lancel S, Zhang J, et al. Redox-mediated reciprocal regulation of SERCA and Na+—Ca2+ exchanger contributes to sarcoplasmic reticulum Ca2+ depletion in cardiac myocytes. Free Radical Biology and Medicine 2010; 48:1182-7.
63. Luo A, Ma J, Zhang P, Zhou H, Wang W. Sodium Channel Gating Modes During Redox Reaction. Cellular Physiology and Biochemistry 2007; 19:9-20.
64. Valdivia C R, Chu W W, Pu J, et al. Increased late sodium current in myocytes from a canine heart failure model and from failing human heart. Journal of Molecular and Cellular Cardiology 2005; 38:475-83.
65. Song Y, Shryock J C, Belardinelli L. An increase of late sodium current induces delayed afterdepolarizations and sustained triggered activity in atrial myocytes. American Journal of Physiology—Heart and Circulatory Physiology 2008; 294:H2031-H9.
66. Wasserstrom J A, Sharma R, O'Toole M J, et al. Ranolazine Antagonizes the Effects of Increased Late Sodium Current on Intracellular Calcium Cycling in Rat Isolated Intact Heart. Journal of Pharmacology and Experimental Therapeutics 2009.
67. Undrovinas N, Maltsev V, Belardinelli L, Sabbah H, Undrovinas A. Late sodium current contributes to diastolic cell $Ca^{2+}$ accumulation in chronic heart failure. The Journal of Physiological Sciences 2010; 60:245-57.
68. Terentyev D, Gyorke I, Belevych A E, et al. Redox Modification of Ryanodine Receptors Contributes to Sarcoplasmic Reticulum Ca2+ Leak in Chronic Heart Failure. Circulation Research 2008; 103:1466-72.
69. Gonzalez D R, Beigi F, Treuer A V, Hare J M. Deficient ryanodine receptor S-nitrosylation increases sarcoplasmic reticulum calcium leak and arrhythmogenesis in cardiomyocytes. Proc Natl Acad Sci USA 2007; 104:20612-7.
70. Marx S O, Marks A R. Dysfunctional ryanodine receptors in the heart: new insights into complex cardiovascular diseases. J Mol Cell Cardiol 2013; 58:225-31.
71. Bootman M D, Smymias I, Thul R, Coombes S, Roderick H L. Atrial cardiomyocyte calcium signalling. Biochim Biophys Acta 2011; 1813:922-34.
72. Niggli E, Ullrich N D, Gutierrez D, Kyrychenko S, Polakova E, Shirokova N. Posttranslational modifications of cardiac ryanodine receptors: Ca(2+) signaling and EC-coupling Biochim Biophys Acta 2013; 1833:866-75.
73. Donoso P, Sanchez G, Bull R, Hidalgo C. Modulation of cardiac ryanodine receptor activity by ROS and RNS. Front Biosci (Landmark Ed) 2011; 16:553-67.
74. Terentyev D, Gyorke I, Belevych A E, et al. Redox modification of ryanodine receptors contributes to sarcoplasmic reticulum Ca2+ leak in chronic heart failure. Circ Res 2008; 103:1466-72.
75. Belevych A E, Terentyev D, Terentyeva R, et al. Shortened Ca2+ signaling refractoriness underlies cellular arrhythmogenesis in a postinfarction model of sudden cardiac death. Circ Res 2012; 110:569-77.
76. Swaminathan P D, Purohit A, Hund T J, Anderson M E. Calmodulin-dependent protein kinase II: linking heart failure and arrhythmias. Circ Res 2012; 110:1661-77.
77. Purohit A, Rokita A G, Guan X, et al. Oxidized Ca2+/Calmodulin-Dependent Protein Kinase II Triggers Atrial Fibrillation. Circulation 2013; 128:1748-57.
78. Ashpole N M, Herren A W, Ginsburg K S, et al. Ca2+/calmodulin-dependent protein kinase II (CaMKII) regulates cardiac sodium channel NaV1.5 gating by multiple phosphorylation sites. J Biol Chem 2012; 287:19856-69.
79. Hund T J, Koval O M, Li J, et al. A beta(IV)-spectrin/CaMKII signaling complex is essential for membrane excitability in mice. J Clin Invest 2010; 120:3508-19.
80. Hashambhoy Y L, Winslow R L, Greenstein J L. CaMKII-dependent activation of late INa contributes to cellular arrhythmia in a model of the cardiac myocyte. Conf Proc IEEE Eng Med Biol Soc 2011; 2011:4665-8.
81. Christensen M D, Dun W, Boyden P A, Anderson M E, Mohler P J, Hund T J. Oxidized calmodulin kinase II regulates conduction following myocardial infarction: a computational analysis. PLoS Comput Biol 2009; 5:e1000583.
82. Arora R. Recent insights into the role of the autonomic nervous system in the creation of substrate for atrial fibrillation: implications for therapies targeting the atrial autonomic nervous system. Circ Arrhythm Electrophysiol 2012; 5:850-9.
83. Kong M H, Piccini J P, Bahnson T D. Efficacy of adjunctive ablation of complex fractionated atrial electrograms and pulmonary vein isolation for the treatment of atrial fibrillation: a meta-analysis of randomized controlled trials. Europace 2011; 13:193-204.
84. Kabra R, Singh J P. Catheter ablation targeting complex fractionated atrial electrograms for the control of atrial fibrillation. Curr Opin Cardiol 2012; 27:49-54.
85. Li D, Fareh S, Leung T K, Nattel S. Promotion of atrial fibrillation by heart failure in dogs: atrial remodeling of a different sort. Circulation 1999; 100:87-95.
86. Koduri H, Ng J, Cokic I, et al. Contribution of fibrosis and the autonomic nervous system to atrial fibrillation electrograms in heart failure. Circ Arrhythm Electrophysiol 2012; 5:640-9.
87. Yeh Y H, Kuo C T, Chan T H, et al. Transforming growth factor-beta and oxidative stress mediate tachycardia-induced cellular remodelling in cultured atrial-derived myocytes. Cardiovasc Res 2011; 91:62-70.
88. Zhang J, Youn J Y, Kim A Y, et al. NOX4-Dependent Hydrogen Peroxide Overproduction in Human Atrial Fibrillation and HL-1 Atrial Cells: Relationship to Hypertension. Front Physiol 2012; 3:140.
89. Vescovo G, Ravara B, Dalla Libera L. Skeletal muscle myofibrillar protein oxidation and exercise capacity in heart failure. Basic Res Cardiol 2008; 103:285-90.
90. Wasserstrom J A, Sharma R, Kapur S, et al. Multiple defects in intracellular calcium cycling in whole failing rat heart. Circ Heart Fail 2009; 2:223-32.
91. Shinagawa K, Derakhchan K, Nattel S. Pharmacological prevention of atrial tachycardia induced atrial remodeling as a potential therapeutic strategy. Pacing Clin Electrophysiol 2003; 26:752-64.
92. Schotten U, Verheule S, Kirchhof P, Goette A. Pathophysiological mechanisms of atrial fibrillation: a translational appraisal. Physiol Rev 2011; 91:265-325.
93. Arora R, Ng J, Ulphani J, et al. Unique autonomic profile of the pulmonary veins and posterior left atrium. J Am Coll Cardiol 2007; 49:1340-8.
94. Arora R, Ulphani J S, Villuendas R, et al. Neural substrate for atrial fibrillation: implications for targeted parasympathetic blockade in the posterior left atrium. Am J Physiol Heart Circ Physiol 2008; 294:H134-44.
95. Ng J, Villuendas R, Cokic I, et al. Autonomic remodeling in the left atrium and pulmonary veins in heart failure: creation of a dynamic substrate for atrial fibrillation. Circ Arrhythm Electrophysiol 2011; 4:388-96.
96. Arora R, Verheule S, Scott L, et al. Arrhythmogenic substrate of the pulmonary veins assessed by high-resolution optical mapping. Circulation 2003; 107:1816-21.
97. Wasserstrom J A, Shiferaw Y, Chen W, et al. Variability in timing of spontaneous calcium release in the intact rat heart is determined by the time course of sarcoplasmic reticulum calcium load. Circ Res 2010; 107:1117-26.
98. Efimov I R, Nikolski V P, Salama G. Optical imaging of the heart. Circ Res 2004; 95:21-33.
99. Kong W, Ideker R E, Fast V G. Intramural optical mapping of V(m) and Ca(i)2+ during long-duration ventricular fibrillation in canine hearts. Am J Physiol Heart Circ Physiol 2012; 302:H1294-305.
100. Cutler M J, Plummer B N, Wan X, et al. Aberrant S-nitrosylation mediates calcium-triggered ventricular arrhythmia in the intact heart. Proc Natl Acad Sci USA 2012; 109:18186-91.
101. Gonzalez D R, Treuer A V, Castellanos J, Dulce R A, Hare J M. Impaired S-nitrosylation of the ryanodine receptor caused by xanthine oxidase activity contributes to calcium leak in heart failure. J Biol Chem 2010; 285:28938-45.

102. Katra R P, Laurita K R. Cellular mechanism of calcium-mediated triggered activity in the heart. Circ Res 2005; 96:535-42.
103. Sridhar A, Nishijima Y, Terentyev D, et al. Chronic heart failure and the substrate for atrial fibrillation. Cardiovascular Research 2009; 84:227-36.
104. Dean D A. Nonviral gene transfer to skeletal, smooth, and cardiac muscle in living animals. American journal of physiology 2005; 289:C233-45.
105. Nattel S, Shiroshita-Takeshita A, Brundel B J, Rivard L. Mechanisms of atrial fibrillation: lessons from animal models. Progress in Cardiovascular Diseases 2005; 48:9-28. 106. Bovo E, Lipsius S L, Zima A V. Reactive oxygen species contribute to the development of arrhythmogenic $Ca(2)(+)$ waves during beta-adrenergic receptor stimulation in rabbit cardiomyocytes. J Physiol 2012; 590:3291-304.
107. Ng J, Goldberger J J. Understanding and interpreting dominant frequency analysis of AF electrograms. J Cardiovasc Electrophysiol 2007; 18:680-5. 108. Everett T H 4th M J, Kok L C, Akar J G, Haines D E. Assessment of global atrial fibrillation organization to optimize timing of atrial defibrillation. Circulation 2001; 103:2857-61.
109. Lin Y J, Tai C T, Kao T, et al. Consistency of complex fractionated atrial electrograms during atrial fibrillation. Heart Rhythm 2008; 5:406-12.
110. Ng J, Borodyanskiy A I, Chang E T, et al. Measuring the Complexity of Atrial Fibrillation Electrograms. Journal of Cardiovascular Electrophysiology 2010; 21:649-55.
111. Po S S, Scherlag B J, Yamanashi W S, et al. Experimental model for paroxysmal atrial fibrillation arising at the pulmonary vein-atrial junctions. [see comment]. Heart Rhythm 2006; 3:201-8. 112. Ng J, Kadish A H, Goldberger J J. Technical considerations for dominant frequency analysis. J Cardiovasc Electrophysiol 2007; 18:757-64.
113. Dibs S R, Ng J, Arora R, Passman R S, Kadish A H, Goldberger J J. Spatiotemporal characterization of atrial activation in persistent human atrial fibrillation: multisite electrogram analysis and surface electrocardiographic correlations—a pilot study. Heart Rhythm 2008; 5:686-93.
114. Scherr D, Dalal D, Cheema A, et al. Long- and short-term temporal stability of complex fractionated atrial electrograms in human left atrium during atrial fibrillation. J Cardiovasc Electrophysiol 2009; 20:13-21.
115. Lau D H, Maesen B, Zeemering S, Verheule S, Crijns H J, Schotten U. Stability of complex fractionated atrial electrograms: a systematic review. J Cardiovasc Electrophysiol 2012; 23:980-7.
116. Lammers W J, Schalij M J, Kirchhof C J, Allessie M A. Quantification of spatial inhomogeneity in conduction and initiation of reentrant atrial arrhythmias. Am J Physiol 1990; 259:H1254-63.
117. Koduri H, Ng J, Cokic I, et al. Contribution of fibrosis and the autonomic nervous system to atrial fibrillation electrograms in heart failure. Circ Arrhythm Electrophysiol 2012; 5:640-9.
118. Ng J, Borodyanskiy A I, Chang E T, et al. Measuring the complexity of atrial fibrillation electrograms. J Cardiovasc Electrophysiol 2010; 21:649-55.

All patents, patent applications, patent application publications, and other publications cited herein are hereby incorporated by reference as if set forth in their entirety.

It should be understood that the methods, procedures, operations, composition, and systems illustrated in figures may be modified without departing from the spirit of the present disclosure. For example, these methods, procedures, operations, devices and systems may comprise more or fewer steps or components than appear herein, and these steps or components may be combined with one another, in part or in whole.

Furthermore, the present disclosure is not to be limited in terms of the particular embodiments described in this application, which are intended as illustrations of various embodiments. Many modifications and variations can be made without departing from its scope and spirit. Functionally equivalent methods and apparatuses within the scope of the disclosure, in addition to those enumerated herein, will be apparent to those skilled in the art from the foregoing descriptions.

The invention claimed is:

1. A method of inhibiting oxidative stress in a subject having atrial fibrillation (AF), comprising administering directly in atrial myocardial tissue of the subject having atrial fibrillation (AF) an effective amount of a NADPH oxidase 2 (NOX2) inhibitor agent, wherein the NOX2 inhibitor agent comprises a NOX2 shRNA and wherein said administering is under conditions such that a level of oxidative stress in atrial myocardial tissue of the subject is reduced or eliminated.

2. The method of claim 1, wherein the NOX2 shRNA is SEQ ID NO: 1.

3. The method of claim 1, wherein administering directly in atrial myocardial tissue of the subject having atrial fibrillation (AF) an effective amount of a NADPH oxidase 2 (NOX2) inhibitor agent comprises:
    (a) providing an isolated therapeutic DNA comprising an small hairpin RNA (shRNA) against NOX2 mRNA (NOX2 shRNA) expression vector that encodes and expresses NOX2 shRNA in vivo; and
    (b) administering directly the isolated therapeutic DNA in atrial myocardial tissue of the subject.

4. The method of claim 3, wherein administering directly the isolated therapeutic DNA in atrial myocardial tissue of the subject comprises injecting the isolated therapeutic DNA.

5. The method of claim 1, further comprising assessing a parameter of atrial tissue status in the subject.

6. The method of claim 5, wherein assessing a parameter of atrial tissue status in the subject comprises monitoring an electrophysiological measurement associated with atrial fibrillation (AF) or assessing fibrosis status for a region of the myocardial tissue after administering NOX2 inhibitor agent to the subject.

7. The method of claim 5, wherein assessing a parameter of atrial tissue status in the subject comprises monitoring an electrophysiological measurement associated with atrial fibrillation (AF) selected from AF onset, AF duration, conductivity and conductive inhomogeneity index.

8. The method of claim 3, further comprising assessing an atrial fibrillation (AF) characteristic following administering directly the isolated therapeutic DNA.

9. The method of claim 8, wherein the atrial fibrillation (AF) characteristic comprises at least one member selected from the group consisting of AF duration, AF episode inducibility, effective refractory periods and conduction inhomogeneity index.

10. The method of claim 1, further comprising assessing at least one member selected from the group consisting of NOX2 nucleic acid, NOX2 polypeptide, superoxide production and fibrosis.

11. A method of treating a subject having atrial fibrillation (AF), comprising administering directly in atrial myocardial tissue of the subject having atrial fibrillation (AF) an effective amount of a NADPH oxidase 2 (NOX2) inhibitor agent, wherein the NOX2 inhibitor agent comprises a NOX2 shRNA and wherein said administering is under conditions such that a level of atrial fibrillation (AF) is reduced or eliminated.

12. The method of claim 11, wherein administering directly in atrial myocardial tissue of the subject having atrial fibrillation (AF) an effective amount of a NADPH oxidase 2 (NOX2) inhibitor agent to the subject comprises:
    (a) providing an isolated therapeutic nucleic acid comprising a small hairpin RNA against NOX2 mRNA (NOX2 shRNA) in vivo; and
    (b) administering directly in atrial myocardial tissue of the subject having atrial fibrillation (AF) the isolated therapeutic nucleic acid.

13. The method of claim 12, further comprising: (c) assessing atrial fibrillation (AF) status for the atrial myocardial tissue after administration of the therapeutic nucleic acid.

14. The method of claim 13, wherein the atrial fibrillation (AF) status comprises at least one member selected from the group consisting of AF duration, AF episode inducibility, effective refractory periods and conduction inhomogeneity index.

15. The method of claim 11, further comprising assessing at least one member selected from the group consisting of NOX2 nucleic acid, NOX2 polypeptide, superoxide production and fibrosis.

16. The method of claim 12, wherein the isolated therapeutic nucleic acid is expressed from an expression vector encoding a NOX2 shRNA.

* * * * *